US007595430B2

(12) United States Patent
Jayakrishna

(10) Patent No.: US 7,595,430 B2
(45) Date of Patent: Sep. 29, 2009

(54) METHODS AND ANIMAL MODEL FOR ANALYZING AGE-RELATED MACULAR DEGENERATION

(75) Inventor: Ambati Jayakrishna, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 785 days.

(21) Appl. No.: 10/685,705

(22) Filed: Oct. 16, 2003

(65) Prior Publication Data

US 2004/0177387 A1 Sep. 9, 2004

Related U.S. Application Data

(60) Provisional application No. 60/422,096, filed on Oct. 30, 2002.

(51) Int. Cl.
*G01N 33/00* (2006.01)
*A01K 67/027* (2006.01)

(52) U.S. Cl. .......................................... 800/3; 800/18

(58) Field of Classification Search .................... 800/3, 800/18

See application file for complete search history.

(56) References Cited

OTHER PUBLICATIONS

Doetschman, T. (1999) Interpretation of phenotype in genetically engineered mice. Laboratory Animal Science 49(2): 137-143.*

Donehower et al. (1995) Effects of genetic background on tumorigenesis in p53-deficient mice. Molecular Carcinogenesis 14: 16-22.*

Jacks et al. (1992) Effects of an Rb mutation in the mouse. Nature 359: 295-300.*

Jaenisch et al. (1988) Transgenic Animals. Science 240: 1468-1474.*

Kuehn et al. (1987) A potential animal model for Lesch-Nyhan syndrome through introduction of HPRT mutations into mice. Nature 326: 295-298.*

Moens et al. (1993) Defects in heart and lung development in compound heterozygotes for two different targeted mutations at the N-myc locus. Development 119: 485-499.*

Petridou et al. (2003) Heterogeneous inducible mammary-specific expression of JAB/SOCS1 in lactating transgenic mice is associated with no obvious phenotype, even at the cellular level. Transgenic Research 12: 693-706.*

Sigmund, CD (2000) Viewpoint: Are studies in genetically altered mice out of control? Arterioscler. Thromb. Vasc. Biol. 20: 1425-1429.*

Lu, Bao., et al, "Abnormalities in Monocyte Recruitment and Cytokine Expression in Monocyte Chemoattractant Protein 1-deficient Mice." J. Exp. Med, Feb. 16, 1998, vol. 187(4), pp. 601-608, ISSN 0022-1007.

Kuziel, William, A.., et al. "Severe reduction in leukocyte adhesion and monocyte extravasation in mice deficient in CC Chemokine receptor 2." Proceeding of the National Academy of the Sciences, USA, vol. 94, No. 22, Oct. 1997, pp. 12053-12058.

Raisler, Brian J., et al. "Adeno-associated virus type-2 expression of pigmented epithelium-derived factor or Kringles 1-3 of angiostatin reduce retinal neovascularization." PNAS, Jun. 25, 2002, vol. 99, No. 13, pp. 8909-8914.

Acland, Gregory, M., et al. "Gene therapy restores vision in canine model of childhood blindness." Nature Genetics, vol. 28, May 2001, pp. 92-95.

Elner, Victor, M., et al. "Cell-Associated Human Retinal Pigment Epithelium Interleukin-8 and Monocyte Chemotactic Protein-1: Immunochemical and In-situ Hybridization Analyses." Experimental Eye Research, Dec. 1997, vol. 65, No. 6, pp. 781-789.

Ambati, J. et al. "An animal model of age-related macular degeneration in senescent macrophage recruitment impaired mice." Association for Research in Vision Opthalmology Annual Meeting Abstract Search and Program Planner, 2003.

Grossniklaus, H. et al. "Macrophage and retinal pigment epithelium expression of angiogenic cytokines in choroidal neovascularization." Molecular Vision, 2002, vol. 8, pp. 119-126.

* cited by examiner

*Primary Examiner*—Anne-Marie Falk
(74) *Attorney, Agent, or Firm*—McDermott Will & Emery LLP

(57) ABSTRACT

Methods for testing candidate drugs for treatment of age-related macular degeneration are provided. Ccl2-deficient, and Ccr2-deficient mice are used to determine the effect of candidate drugs and treatments on development of age-related macular degeneration. Also provided is a Ccl2-deficient, Ccr2-deficient dual knockout mouse, which is a useful animal model for age-related macular degeneration.

27 Claims, 23 Drawing Sheets
(6 of 23 Drawing Sheet(s) Filed in Color)

BM
CH
NPP
A2E
592.5
Relative intensity

CC
CC
CC
CC

PR
R

F
F
E migrated macrophages per mm2
PBS
BSA
C5a
IgG
CCL2

% adherent macrophages
BSA
C5a
μg/spot

Relative C5-positive RPE and choroidal area
Mφ
CCL2
CCR2

Relative IgG-positive RPE and choroidal area
Mφ
CCL2
CCR2

Figure 7A
SEQ ID NO 1: Human Ccl2 gene:
Sequence 1:

```
1   ggaaccgaga ggctgagact aacccagaaa catccaattc tcaaactgaa gctcgcactc
61  tcgcctccag catgaaagtc tctgccgccc ttctgtgcct gctgctcata gcagccacct
121 tcattcccca agggctcgct cagccagatg caatcaatgc cccagtcacc tgctgttata
181 acttcaccaa taggaagatc tcagtgcaga ggctcgcgag ctatagaaga atcaccagca
241 gcaagtgtcc caaagaagct gtgatcttca agaccattgt ggccaaggag atctgtgctg
301 accccaagca gaagtgggtt caggattcca tggaccacct ggacaagcaa acccaaactc
361 cgaagacttg aacactcact ccacaaccca agaatctgca gctaacttat ttcccctag
421 ctttccccag acaccctgtt ttattttatt ataatgaatt ttgtttgttg atgtgaaaca
481 ttatgcctta agtaatgtta attcttattt aagttattga tgttttaagt ttatctttca
541 tggtactagt gtttttaga tacagagact tggggaaatt gcttttcctc ttgaaccaca
601 gttctacccc tgggatgttt tgagggtctt tgcaagaatc attaatacaa agaattttt
661 ttaacattcc aatgcattgc taaaatatta ttgtggaaat gaatattttg taactattac
721 accaaataaa tatattttg tacaaaaaaa aaaaaaa
```

Figure 7B
SEQ ID NO. 2: Human Ccl2 gene variant
Sequence 2:

```
1   agactaaccc agaaacatcc aattctcaaa ctgaagctcg cactctcgcc tccagcatga
61  aagtctctgc cgcccttctg tgcctgctgc tcatagcagc caccttcatt ccccaagggc
121 tcgctcagcc agatgcaatc aatgccccag tcacctgctg ttataacttc accaatagga
181 agatctcagt gcagaggctc gcgagctata gaagaatcac cagcagcaag tgtcccaaag
241 aagctgtgat cttcaagacc attgtggcca aggagatctg tgctgacccc aagcagaagt
301 gggttcagga ttccatggac cacctggaca agcaaaccca aactccgaag acttgaacac
361 tcactccaca acccaagaat ctgcagctaa cttatttcc cctagctttc cccagacacc
421 ctgttttatt ttattataat gaattttgtt tgttgatgtg aaacattatg ccttaagtaa
481 tgttaattct tatttaagtt attgatgttt taagtttatc tttcatggta ctagtgtttt
541 ttagatacag agacttgggg aaattgcttt tcctcttgaa ccacagttct acccctggga
601 tgttttgagg gtctttgcaa gaatcattaa tacaaagaat ttttttaac attccaatgc
661 attgctaaaa tattattgtg gaaatgaata ttttgtaact attacaccaa ataaatatat
721 ttttgtacaa aaaaaaaaa aaa
```

Figure 7C
SEQ ID NO. 3: Human Ccl2 promoter region:

```
1   ccgagatgtt cccagcacag ccccatgtga gagctccctg gctccgggcc cagtatctgg
61  aatgcaggct ccagccaaat gcattctctt ctacgggatc tgggaacttc caaagctgcc
121 tcctcagagt gggaatttcc actcacttct ctcacgccag cactgacctc ccagcggggg
181 agggcatctt ttcttgacag agcagaagtg ggaggcagac agctgtcact ttccagaaga
241 ctttcttttc tgattcatac ccttcacctt ccctgtgttt actgtctgat atatgcaaag
301 gccaagtcac tttccagaga tgacaactcc ttcctgaagt agagacatgc ttccaacact
361 cagaagccta tgtgaacact cagccagcaa agctgggaag tttttctctg tgaccatggg
421 ctaattggtc tccttctctg gattgtggct ttatcagata aaaacaagtg gtcatgccac
481 aggatgtcta taagcccatt gattctggga ttctatgagt gatgctgata tgactaagcc
541 aggagagact tatttaaaga tctcagcatc tttcagcttg ttaacctaga gaaaacccga
601 agcatgactg gattataaag ggaaattgaa tgcggtccac caagttcatg gtaaaggatg
661 cactaacaga ttagagagag gtttcccctg atatgaggaa aacttcttgg aagatgaggt
721 gagatggcct aggaagaaat tcctacacaa aattgcacag tctctagtcc tggaaacatt
781 ttattcattg gataagaatg gattgaggca tgagcagagg actgagacaa acacagagaa
841 gtttcaacac tggttgggga gaaaaggagt aactagtgag attcaggcag aacaagaata
```

901 aggctcctca agaggcacaa gcaaagcagg gctcgagttg atttgttctc tcttcatcct
961 gctttttgta attccaccag agtctgaaat gaccactcca tagagtctct gctctgggat
1021 tctccaggaa accaatatcc atcatgagac atcaagtcta gtcccaggaa gaagagattc
1081 tggaatggaa acatcctggg tgggagtctc agcacatcta ctattctgtc tgagttactg
1141 gacaaataac ttcagtttta acctaacgaa agctgggttg gttggaggac tgggcaggca
1201 gcgctggaaa gtatgtcagc accatacctg actccctgaa tgcactcaac aatgccatta
1261 ctgaccactt actagaaata aaacagtcat ttgttgaata caacccgttt ctttttacaa
1321 gtgtagtgaa aagtgttttc tttcaagaaa ccccatgcat ttatagacat tgcctcagtg
1381 accctttatg aaagaagtca ctagtctttg tatgcccatt gggcaagggc accgcaaggc
1441 tcagaaggag gaggcagtgg gctaggagaa tggagagatc agaattttaa actcagccca
1501 gccattaaca tgcctcaagt actcctatca tatttgtaag agacaacagt tcactgaaat
1561 gaattctaag gtctttgggt ttttatcagt gtgcttctgt agtttctgag gaaatctaag
1621 gcacaactga ggaatgaagt caggctttcc aattcccgaa atactcctcc actgcttact
1681 catgtccctt ggaaattaag aaggaagcca ggagaatagc tgccataacc agggatgaac
1741 ttcttgtcca ctgctgcctg ctatgctagc aacagcctcc taactcataa tgacttagcc
1801 atgaggaatg tttctagatt ctcctttagc tgtctgccca tttggaagat gctgaggaca
1861 gagagaggac ccaagcaggc aactagttgg aggacttgta cacgtttcct tccagcagta
1921 tgtcagagag gtgagcagcc cactggggac agggctgcct gggttctgtg ctcgagggga
1981 ccttgagcag gctatttaac ccttctgtgc ctcagttgcc tgatctataa catgaaaatt
2041 agcaatccct actagataaa gttggggaat ttacagagtt aatatttgta aaggtctgag
2101 aatattcctg gcagagtaag cactctgtga gtatgacact ggcatttctt ctgcagcact
2161 acatgctgtc tatgcctttg tccaagtctg aaaccctaga actcttagaa ttcagttcaa
2221 tgtttacaca atcctacagt tctgctaggc ttctatgatg ctactattct gcatttgaat
2281 gagcaaatgg atttaatgca ttgtcaggga gccggccaaa gcttgagagc tccttcctgg
2341 ctgggaggcc ccttggaatg tggcctgaag gtaagctggc agcgagcctg acatgctttc
2401 atctagtttc ctcgcttcct tccttttctg cagttttcgc ttcacagaaa gcagaatcct
2461 taaaaataac cctcttagtt cacatctgtg gtcagtctgg gcttaatggc accccatcct
2521 ccccatttgc tcatttggtc tcagcagtga atggaaaaag tgtctcgtcc tgaccccctg
2581 cttccctttc ctacttcctg gaaatccaca ggatgctgca tttgctcagc agatttaaca
2641 gcccacttat cactcatgga agatccctcc tcctgcttga ctccgccctc tctccctctg
2701 cccgctttca ataagaggca gagacagcag ccagaggaac cgagaggctg agactaaccc
2761 agaaacatcc aattctcaaa ctgaagctcg cactctcgcc tccagcatga aagtctctgc
2821 cgccccttctg tgcctgctgc tcatagcagc caccttcatt ccccaagggc tcgctcagcc
2881 aggtaaggcc ccctcttctt ctccttgaac cacattgtct tctctctgag ttatcatgga
2941 ccatccaagc agacgtggta cccacagtct tgctttaacg ctacttttcc aagataaggt
3001 gactcagaaa aggacaaggg gtgagcccaa ccacacagct gctgctcggc agagcctgaa
3061 ctagaattcc agctgtgaac cccaaatcca gctccttcca ggattccagc tctgggaaca
3121 cactcagcgc agttactccc ccagctgctt ccagcagagt ttggggatca gggtaatcaa
3181 agagagggtg ggtgtgtagg ctgtttccag acacgctgga g Figure 7D
SEQ ID NO. 4: .Human Ccl2 gene and enhancer region:

1 ggtacctcct ccagccttgg ccacagtgtc atccttgggc cccctaggtt tcagcctctt
61 gagtttgcac ttgcaggttt ggctgttgct ctcaaagcag gactattgca tcaacatggc
121 aggtgcagag gtcttcccgc ctcaatcgtc acccactgat ttctctgcca tggccttgaa
181 ctcaggcgac caatccagtt ggaacctccc cacactctcc gtggctaata attttggact
241 cagaagaaaa agcctcaatt tctctcctct caggaggtct cttggtcctt gagcaaatgt
301 atccatttct tctcctatct ccagtctttg ggcccccaaa ggtttttttc tccctttctc
361 caggacaatg agtgcctatt tacaagtgcc tgtttctact tgaataaggt ttctataaac
421 taagaagtgt tccttaggga cacaagtaac tggcactcct gttggaaaat gctaagatct
481 aggtcacgcg cacttccccc aacagacaca tacacacatt cacacacaca cacacacaca
541 cacacacaca cacacacaca cacacataca gcttgtctgc actctagcac tggcactgac
601 gctaacgcta taatcctggg caactttatt tccccatctt acattaagca gtggtgcagg
661 gattttcaac tctgggatct ctatcacacc tcccagctct gattgcttcc taatttacat
721 atttattgag catctgatgc taggtcctca tgctggtgat gcaggagtaa actagacaga 781 caaaagtccg tgccccacat tgtctgacac ctacacacct gctgttcgga ctccattaca
841 aacagctcca aggggaacag tgcacttgta aagtttctct cattaccatg gccacatccg
901 tgagcaataa ataagttgca tagttgaatt atttgataat gctttgtttt taactccctg
961 cacttaagtc agagatgtgt gtgctttgga aaactatttc tcctgactca ttagacaaat
1021 actatttgca tttttattca gcttccttcc tcagactcta atttacagta aaggcaagag
1081 gatttttgaa tggagccagt gctttgcaat gtggggctcc accagctagc cgactgaaat
1141 cattaataaa gaagcctttt taagtggctg aagtttcccc tttttggcat gcaacatttt
1201 gcaaccaagc ggaagaaaca tcatccgcaa agaagaatcc atgtggcccc tgaaaatcac
1261 tctctctgct acaggctccc cactccccag tgctcccctt agccctgcca ctatctctcc
1321 tccagatgga aaaagtgagg aactcaggga accaaaagtc ttgcttcttt actaatttcc
1381 ctgtctgaca ttaaatcatc ctacagttca gatatctggg ggaagtgact agagattctt
1441 gaactgttaa taattaattt aaatgatatt tgttaagaac ctacgacatg gaagatactg
1501 taccaggtgc tggggtccag catgggcaaa ggcctcaagg tggaatggag ctatggtgtg
1561 ttctggaagc agagagtggg gctgagggtg acatgaggtg aggagacagg agagggcctg
1621 gcagggtggg accttctggt gagagctggc tgctgtgtga ggagctgagg ccctggcttg
1681 attctggggt tacttctttg accttcagct tttgtcatgg ggcagacaga atggggatga
1741 aaaaaagctt aggaaatgga aacctcccta tgcattatat aataaaaatg gccaacacat
1801 tttcatagca agaaatcaca gcagaagctt gtactgggca tcaggactgt aggcatccaa
1861 tgcccagaaa ctggcatgtg ccctgggaca tcccctgaga aggcatgcca cgagccctca
1921 gactgacaca gctctttaca agttgcttac agagcactct tggtttatta attcatacaa
1981 gtctcatgac aatgtcagaa gcagctgtct tactaatccc ctttgacaga agaggcccag
2041 agaggtcaag ggacttgctc aaggccacac agctagaaag aggcagagcc aggcctttgg
2101 ccctggtgtt ctgacaccac ctggggctcc ttctgttatt ccatgctacc tcttctttct
2161 cttccgtatt cccttctcgt tcccttcctt cttgtgtctt gcttcttatc tgcctgtact
2221 tattcctgtt ggtgcctccc agctcagcca gcatagctct gtcttcaaat accccatgct
2281 tcattctggg gtcccataca cagtctgaca atcatctgag gggctgtgg gaggacatag
2341 aaaaaataca gctttacata gaaaaaaatg caaattgtag ccaggcgcag tggctcatgc
2401 ctgtaacccc agcactttgg gaggccgagg caggtggatc acctgaggtc aggagtctga
2461 gaccagcctg gccaatgtag taaaactcct tctctactaa aaatataaaa attagccagg
2521 cgtgatgtca tgtgcctgta gtcccagcta ctcgggaggc tgaggcagga gaacctcttg
2581 aatccaggag gcgcaggttg cagtgagcag agatagtgcc actgcactcc agcctgggtg
2641 acagagtgag actctgtctc aaaaaaataa aataaaataa aaaatgcaga ctgtgattca
2701 gcaggtctgg gttgaagccc agaactctct gataaattca atggcactta actacttgga
2761 ggtcatggat gcctttgcta atctaataga agctactgac cctctctcca gaaaaatgca
2821 caaaaacata aatgtggaag acaactcctg atggatctgg gagcctatcc aagggccaca
2881 gacaagagtc ctggtctgga caaaatgagc tgctcagtat tttcccacct ggccagcatt
2941 tcctatccaa agacaaatgt taaagttgtt ctagcagagc catgcaccag cagcagtatc
3001 atcacctggg aaccggttag caatgcagaa ccgcaggccc accccaaacc tacagtcaga
3061 atctctactt tagcaagatc ctaaggagat gggtaagcac attacaattt gcaacctttg
3121 taagtttgcc caaaatgtga cccctccttc acccaccgat cgccaaggtt caaaaatctg
3181 cccaaccctt gagcccatct taaatgtacc atcacgagcc ttccctgggc ccctcagctg
3241 ggactctcac cgctctgtat ctttctggtt aatgcaatta ttctgttccc ttagatgacc
3301 ccagcacagg tgctaaagga gtcaacaaaa ggctattgtc aaaaaagtgt ttctgtctcc
3361 actccatctg atctctgttt ccctaagacc tgcccatccc cctctcccag ttcggcacct
3421 tgaccccctc atcacactgc tcaggccacc ttgtacaatg caagccccaa atgaggaaag
3481 cattttctcc cccaatgtgt aacacgaaag tgctgtagag tggctcacgc tgcctttagc
3541 ctaagaattt atttaactct tacccccaac ccacatcagt ctcctccctc tagggctcag
3601 gtgctaatct gtgagggctg gctcagaaga caatctaaag aacaagcctc ttgcttcctc
3661 aggcatcact actcctcacc accatcaccc ccacccacca actcaggcca ctactctttc
3721 tgttctcata tgctatgccc atcgccaccc ctattcccat gctcaggagt attcttggct
3781 actgcatgca attagacctg gggcagatcc aatccagaaa gcaagaaatc ttagatgctg
3841 gaagcttggg gtaagtactg atcagattta ttcctaaatt cagtcctact ttccatggat
3901 tcttacttta gcatctcttc tgaaaaggaa gcatcatgtc taattcactt ctccctccct
3961 gtgcagtcct ctacctggtg ctctgcacag ggtatgtgct aattgtatga atgttataat
4021 aaagagatag tgcagtagat gacaaagggc actacattga gagcccagaa ataagcaaac
4081 cagcacaaat gtagccattc gtcttctatc tcaccttgag cctgtcacta acctgttcat
4141 ggcctcagtc tccccatcag agaaacaggt agatggtctc taaggtctcg ttcattttct

```
4201 gacattctgt gaaaaattaa ggaaagattt tcatccttga caggaaaggg attgcagagt
4261 agcggccctg ggaaaatggg ctctattcta cctggagcta gcctggagga gaggccttga
4321 gtgggggttg tctagaaagg acatggtgag tgcagagcta cggtgcatct ctcttgaagg
4381 ctgagtgaag ggagcaccag caagggagcc tgcactaggt ggggagggac aagtgaaccg
4441 cagaagttgg tgggagccca ggcagtggct tcagatcttt ccagagagct cacttttact
4501 tcctcttttt ttcacccctg acactgagtg ggagtctgca gcgatgacca aggttcatgc
4561 agaggatctt agtggtgggg tcagaccccg ggaggaatga agaaagcatt attcaccaag
4621 aggagctttt ccattcttta tctatgagtt gatagagagg aggccccggg gtaactgagg
4681 attctggaca gcatcagagc attgaccctc atttccccca tagcccctct gggggccttt
4741 cccttgtgtg tccccaagcg agagtccaac caaggtttgt gccagagcct aacccaggct
4801 tgtgccgaga tgttcccagc acagccccat gtgagagctc cctggctccg ggcccagtat
4861 ctggaatgca ggctccagcc aaatgcattc tcttctacgg gatctgggaa cttccaaagc
4921 tgcctcctca gagtgggaat ttccactcac ttctctcacg ccagcactga cctcccagcg
4981 ggggagggca tcttttcttg acagagcaga agtgggaggc agacagctgt cactttccag
5041 aagactttct tttctgattc ataccettca ccttccctgt gtttactgtc tgatatatgc
5101 aaaggccaag tcactttcca gagatgacaa ctccttcctg aagtagagac atgcttccaa
5161 cactcagaag cctatgtgaa cactcagcca gcaaagctgg gaagtttttc tctgtgacca
5221 tgggctaatt ggtctccttc tctggattgt ggctttatca gataaaaaca agtggtcatg
5281 ccacaggatg tctataagcc cattgattct gggattctat gagtgatgct gatatgacta
5341 agccaggaga gacttattta aagatctcag catctttcag cttgttaacc tagagaaaac
5401 ccgaagcatg actggattat aaagggaaat tgaatgcggt ccaccaagtt catggtaaag
5461 gatgcactaa cagattagag agaggtttcc cctgatatga ggaaaacttc ttggaagatg
5521 aggtgagatg gcctaggaag aaattcctac acaaagttgc acagtctcta gtcctggaaa
5581 cattttattc attggataag aatggattga ggcatgagca gaggactgag acaaacacag
5641 agaagtttca acactggttg gggagaaaag gagtaactag tgagattcag gcagaacaag
5701 aataaggctc ctcaagaggc acaagcaaag cagggctcga gttgatttgt tctctcttca
5761 tcctgctttt tgtaattcca ccagagtctg aaatggccac tccatagagt ctctgctctg
5821 ggattctcca ggaaaccaat atccatcatg agacatcaag tctagtccca ggaagaagag
5881 attctggaat ggaaacatcc tgggtgggag tctcagcaca tctactattc tgtctgagtt
5941 actggacaaa taacttcagt tttaacctaa cgaaagctgg gttggttgga ggactgggca
6001 ggcagcgctg gaaagtatgt cagcaccata cctgactccc tgaatgcact caacaatgcc
6061 attactgacc acttactaga aataaaacag tcatttgttg aatacaaccc gtttcttttt
6121 acaagtgtag tgaaaagtgt tttctttcaa gaaaccccat gcatttatag acattgcctc
6181 agtgaccctt tatgaaagaa gtcactagtc tttgtatgcc cattgggcaa gggcaccgca
6241 aggctcagaa ggaggaggca gtgggctagg agaatcgaga gatcagaatt ttaaactcag
6301 cccagccatt aacatgcctc aagtactcct atcatatttg taagagacaa cagttcactg
6361 aaatgaattc taaggtcttt gggtttttat cagtgtgctt ctgtagtttc tgaggaaatc
6421 taaggcacaa ctgaggaatg aagtcaggct ttccaattcc cgaaatactc ctccactgct
6481 tactcatgtc ccatggaaat taagaaggaa gccaggagaa tagctgccat aaccagggat
6541 gaacttcttg tccactgctg cctgctatgc tagcaacagc ctcctaactc ataatgactt
6601 agccatgagg aatgtttcta gattctcctt tagctgtctg cccatttgga agatgctgag
6661 gacagagaga ggacccaagc aggcaactag ttggaggact tgtacacgtt tccttccagc
6721 agtatgtcag agaggtggca gcccactggg gacagggctg cctgggttct gtgctcgagg
6781 ggaccttgag caggctattt aaccccttctg tgcctcagtt gcctgatcta taacatgaaa
6841 attagcaatc cctactagat aaagttgggg aatttacaga gttaatattt gtaaaggtct
6901 gagaatattc ctggcagagt aagcactctg tgagtatgac actggcattt cttctgcagc
6961 actacatgct gtctatgcct ttgtccaagt ctgaaaccct agaactctta gaattcagtt
7021 caatgtttac acaatcctac agttctgcta ggcttctatg atgctactat tctgcatttg
7081 aatgagcaaa tggatttaat gcattgtcag ggagccggcc aaagcttgag agctccttcc
7141 tggctgggag gccccttgga atgtggcctg aaggtaagct ggcagcgagc ctgacatgct
7201 ttcatctagt ttcctcgctt ccttcctttt ctgcagtttt cgcttcacag aaagcagaat
7261 ccttaaaaat aaccctctta gttcacatct gtggtcagtc tgggcttaat ggcaccccat
7321 cctccccatt tgctcatttg gtctcagcag tgaatggaaa aagtgtctcg tcctgacccc
7381 ctgcttccct ttcctacttc ctggaaatcc acaggatgct gcatttgctc agcagattta
7441 acagcccact tatcactcat ggaagatccc tcctcctgct tgactccgcc ctctctccct
7501 ctgcccgctt tcaataagag gcagagacag cagccagagg aaccgagagg ctgagactaa
7561 cccagaaaca tccaattctc aaactgaagc tcgcactctc gcctccagca tgaaagtctc
```

```
7621 tgccgccctt ctgtgcctgc tgctcatagc agccaccttc attccccaag ggctcgctca
7681 gccaggtaag gccccctctt cttctccttg aaccacattg tcttctctct gagttatcat
7741 ggaccatcca agcagacgtg gtacccacag tcttgcttta acgctacttt tccaagataa
7801 ggtgactcag aaaaggacaa ggggtgagcc caaccacaca gctgctgctc ggcagagcct
7861 gaactagaat tccagctgtg aaccccaaat ccagctcctt ccaggattcc agctctggga
7921 acacactcag cgcagttact cccccagctg cttccagcag agtttgggga tcagggtaat
7981 caaagagagg gtgggtgtgt aggctgtttc cagacacgct ggagacccag aatctggtct
8041 gtgcttcatt caccttagct tccagagacg gtgactctgc agaggtaatg agtatcaggg
8101 aaactcatga ccaggcatag cctattcaga gtctaaaagg aggctcatag tggggctccc
8161 cagctgatct tccctggtgc tgatcatctg gattattggt ccgtcttaat gacacttgta
8221 ggcattatct agctttaact ctgtccatta tcaatgttat atacccattt tacagcatag
8281 gaaactgagt cattgggtca aagatcacat tctagctctg aggtataggc agaagcactg
8341 ggatttaatg agctctttct cttctcctgc ctgccttttg cttttcctc atgactcttt
8401 tctgctctta agatcagaat aatccagttc atcctaaaat gctttttctt tgtggtttat
8461 tttccagatg caatcaatgc cccagtcacc tgctgctata acttcaccaa taggaagatc
8521 tcagtgcaga ggctcgcgag ctatagaaga atcaccagca gcaagtgtcc caaagaagct
8581 gtgatgtgag ttcagcacac caaccttccc tggcctgaag ttcttccttg tggagcaagg
8641 gacaagcctc ataaacctag agtcagagag tgcactattt aacttaatgt acaaaggttc
8701 ccaatgggaa aactgaggca ccaagggaaa aagtgaaccc caacatcact ctccacctgg
8761 gtgcctattc agaacacccc aatttcttta gcttgaagtc aggatggctc cacctggaca
8821 cctataggag cagtttgccc tgggttccct ccttccacct gcgttcctcc tctagctccc
8881 atggcagccc tttggtgcag aatgggctgc acttctagac caaaactgca aaggaacttc
8941 atctaactct gtcctccctc cccacagctt caagaccatt gtggccaagg agatctgtgc
9001 tgaccccaag cagaagtggg ttcaggattc catggaccac ctggacaagc aaacccaaac
9061 tccgaagact tgaacactca ctccacaacc caagaatctg cagctaactt attttcccct
9121 agctttcccc agacaccttg ttttatttta ttataatgaa ttttgtttgt tgatgtgaaa
9181 cattatgcct taagtaatgt taattcttat ttaagttatt gatgttttaa gtttatcttt
9241 catggtacta gtgtttttta gatacagaga cttggggaaa ttgcttttcc tcttgaacca
9301 cagttctacc cctgggatgt tttgagggtc tttgcaagaa tcattaatac aaagaatttt
9361 ttttaacatt ccaatgcatt gctaaaatat tattgtggaa atgaatattt tgtaactatt
9421 acaccaaata aatatatttt tgtacaaaac ctgacttcca gtgttttctt gaaggaaatt
9481 acaaagctga gagtatgagc ttggtggtga caaaggaaca tgatttcaga gggtggggct
9541 tacattttga aggaatggga aagtggattg gccccggtct tctccactgg gtggtctcct
9601 ctgagtctcc gtagaagaat ctttatggca ggccagttag gcattaaagc accacccttc
9661 cagtcttcaa cataagcagc ccagagtcca atgaccctgg tcacccattt agcaagagcc
9721 caaccccat tccttttctc acagaccctg acccctgcat gcaattcttc ccttaacata
9781 ttgcaactgc cccctaactg ggctacccac cccccaatct gtacctctcc aattaatacc
9841 ccaacctgga gtaatacaga cactgccagt attagcaaat aaggaaagag ttaatcacca
9901 tagataagat gattagattg aagtttcata gagatgatga gacctgaact tattatttat
9961 gaatgaagaa ggcttttcta ggaaaattat aggatcatta agaaaggaga aggaagagtg
10021 ggagcaaata cctggaggta gaaatggtga tgatgtgtac atcaagcagg gagaaaacca
10081 atgaaccaga tgcgaattcg ggcccacacc aatgtcaagg gatgacaatt agaaaggaag
10141 gttgagtcaa gggatttgaa tgttagggtg aaaagttact actcaactct gtaggttaaa
10201 aggaaacgtt gagaatcttc agtccaatga ggagggatgt gccatgttta gagattcaga
10261 gataagtttc aggaaatgta acttatagat tttatacata cacagagaaa tacggactag
10321 tgagaagcta ttgccatggt ccaagcaaga gatgatgaag gcctaaatat ggagccaaag
10381 aggcagcaat gaagaatgag ccatgcaggg tgaaatgctg catgttgtaa atggaggaga
10441 aagacctgtg acttcagata tgaaaacctc atcttcaacc cacattttaa gggggcagct
10501 tccctgaaac cagaatgtgt ttccctccat tactataccc ccatcccaat ctcaggcacc
10561 tggaatcatc catttaaaca gatgagcctt ctattcctaa atagccacct gaagtgtgta
10621 ttcctttgca tgatatttgt cccacctaaa gcattcgacc tgcctgggca cccacaccac
10681 gccaacactc aggaaagcag atgtcttgct ctgttgaata aactgcatgg ttcttaactt
10741 cccagtctgg tggggaaatg accactgtgt caacctagag caggcagtgc ttttggcagc
10801 atgaggtgct ggggacaact ttgactggca agaagcacac tcaggttctc accccgcatc
10861 cagcgctgac tcgctttgtc agtcaagaca ggtcagatat tctgagccta catcgatcat
10921 acaggtatga taatgtgtta caaataggaa cccagaggaa aggttcccttt tcggatctgg
10981 gagcacatct gttggaaaac ttccatttct actaactgga gttgcagagg gagagaaggg
```

```
11041 attctgcttc tacattcctg agccagtcca gggtccctga atcagactac cgaatccctt
11101 caaagctcca agtaccctga tatatcagtc agcagacaat ttattgacag ctatttagaa
11161 aactcactga ccctcactcc aggtcaagca gcgtcccctg cctctcctct acccctacat
11221 tccctggcct tgatcaccag tcaggagtga aatctcaaat tgcagtagat gccaagaggc
11281 aaaaagagaa tagaatgcaa acaaatgaga cctcatcata tggcttccga gcagcaacct
11341 tttgacgcca ggcagatttg aggcagacag tctgggagga gaggaggcag agaaaggggg
11401 gatccacatg ctcaaacccc aaattaatct gcttacattc cccttgcagg ccacatctct
11461 tcattttcag gaagtcttga ctccatactg ttttccaccc aagcatggaa ttcctttcat
11521 gatgaaactg aacacagggc attggcagtg gtgagactct gttttagaag aaagtgccaa
11581 gtgcaatgca ttcatttcct gttgctgcca acaatcagtt ccaggaaatc taggcttttt
11641 atgtcatgct caaaattctt ccagcctatg ctcattattc aaatccaaag ccacatccac
11701 atctgtaggt gttagttaca gaagcaccat atttccaggt accaaaatct gtattagttt
11761 cttattgtta ctgtaacaaa ttcccataag ctt
```

Figure 8A
SEQ ID NO. 5: Human Ccr2 geneVariant A

```
   1 caggactgcc tgagacaagc cacaagctga acagagaaag tggattgaac aaggacgcat
  61 ttccccagta catccacaac atgctgtcca catctcgttc tcggtttatc agaaatacca
 121 acgagagcgg tgaagaagtc accacctttt ttgattatga ttacggtgct ccctgtcata
 181 aatttgacgt gaagcaaatt ggggcccaac tcctgcctcc gctctactcg ctggtgttca
 241 tctttggttt tgtgggcaac atgctggtcg tcctcatctt aataaactgc aaaaagctga
 301 agtgcttgac tgacatttac ctgctcaacc tggccatctc tgatctgctt tttcttatta
 361 ctctcccatt gtgggctcac tctgctgcaa atgagtgggt ctttgggaat gcaatgtgca
 421 aattattcac agggctgtat cacatcggtt attttggcgg aatcttcttc atcatcctcc
 481 tgacaatcga tagatacctg gctattgtcc atgctgtgtt tgctttaaaa gccaggacgg
 541 tcacctttgg ggtggtgaca agtgtgatca cctggttggt ggctgtgttt gcttctgtcc
 601 caggaatcat ctttactaaa tgccagaaag aagattctgt ttatgtctgt ggcccttatt
 661 ttccacgagg atggaataat ttccacacaa taatgaggaa cattttgggg ctggtcctgc
 721 cgctgctcat catggtcatc tgctactcgg gaatcctgaa aaccctgctt cggtgtcgaa
 781 acgagaagaa gaggcatagg gcagtgagag tcatcttcac catcatgatt gtttactttc
 841 tcttctggac tccctataac attgtcattc tcctgaacac cttccaggaa ttcttcggcc
 901 tgagtaactg tgaaagcacc agtcaactgg accaagccac gcaggtgaca gagactcttg
 961 ggatgactca ctgctgcatc aatcccatca tctatgcctt cgttggggag aagttcagaa
1021 gcctttttca catagctctt ggctgtagga ttgccccact ccaaaaacca gtgtgtggag
1081 gtccaggagt gagaccagga aagaatgtga aagtgactac acaaggactc ctcgatggtc
1141 gtggaaaagg aaagtcaatt ggcagagccc ctgaagccag tcttcaggac aaagaaggag
1201 cctagagaca gaaatgacag atctctgctt tggaaatcac acgtctggct tcacagatgt
1261 gtgattcaca gtgtgaatct tggtgtctac gttaccaggc aggaaggctg agaggagaga
1321 gactccagct gggttggaaa acagtatttt ccaaactacc ttccagttcc tcatttttga
1381 atacaggcat agagttcaga ctttttttaa atagtaaaaa taaaattaaa gctgaaaact
1441 gcaacttgta aatgtggtaa agagttagtt tgagttgcta tcatgtcaaa cgtgaaaatg
1501 ctgtattagt cacagagata attctagctt tgagcttaag aattttgagc aggtggtatg
1561 tttgggagac tgctgagtca acccaatagt tgttgattgg caggagttgg aagtgtgtga
1621 tctgtgggca cattagccta tgtgcatgca gcatctaagt aatgatgtcg tttgaatcac
1681 agtatacgct ccatcgctgt catctcagct ggatctccat tctctcaggc ttgctgccaa
1741 aagccttttg tgttttgttt tgtatcatta tgaagtcatg cgtttaatca cattcgagtg
1801 tttcagtgct tcgcagatgt ccttgatgct catattgttc cctaatttgc cagtgggaac
1861 tcctaaatca aattggcttc taatcaaagc ttttaaaccc tattggtaaa gaatggaagg
1921 tggagaagct ccctgaagta agcaaagact ttcctcttag tcgagccaag ttaagaatgt
1981 tcttatgttg cccagtgtgt ttctgatctg atgcaagcaa gaaacactgg gcttctagaa
2041 ccaggcaact tgggaactag actcccaagc tggactatgg ctctactttc aggccacatg
2101 gctaaagaag gtttcagaaa gaagtgggga cagagcagaa ctttcacctt catatatttg
2161 tatgatccta atgaatgcat aaaatgttaa gttgatggtg atgaaatgta aatactgttt
2221 ttaacaacta tgatttggaa aataaatcaa tgctataact atgttgataa aag
```

Figure 8B
SEQ ID NO. 6: Human Ccr2 gene – Variant B

```
   1 caggactgcc tgagacaagc cacaagctga acagagaaag tggattgaac aaggacgcat
  61 ttccccagta catccacaac atgctgtcca catctcgttc tcggtttatc agaaatacca
 121 acgagagcgg tgaagaagtc accacctttt ttgattatga ttacggtgct ccctgtcata
 181 aatttgacgt gaagcaaatt ggggcccaac tcctgcctcc gctctactcg ctggtgttca
 241 tctttggttt tgtgggcaac atgctggtcg tcctcatctt aataaactgc aaaaagctga
 301 agtgcttgac tgacatttac ctgctcaacc tggccatctc tgatctgctt tttcttatta
 361 ctctcccatt gtgggctcac tctgctgcaa atgagtgggt ctttgggaat gcaatgtgca
 421 aattattcac agggctgtat cacatcggtt attttggcgg aatcttcttc atcatcctcc
 481 tgacaatcga tagatacctg gctattgtcc atgctgtgtt tgctttaaaa gccaggacgg
 541 tcacctttgg ggtggtgaca agtgtgatca cctggttggt ggctgtgttt gcttctgtcc
```

```
 601 caggaatcat ctttactaaa tgccagaaag aagattctgt ttatgtctgt ggcccttatt
 661 ttccacgagg atggaataat ttccacacaa taatgaggaa cattttgggg ctggtcctgc
 721 cgctgctcat catggtcatc tgctactcgg gaatcctgaa aaccctgctt cggtgtcgaa
 781 acgagaagaa gaggcatagg gcagtgagag tcatcttcac catcatgatt gtttactttc
 841 tcttctggac tccctataac attgtcattc tcctgaacac cttccaggaa ttcttcggcc
 901 tgagtaactg tgaaagcacc agtcaactgg accaagccac gcaggtgaca gagactcttg
 961 ggatgactca ctgctgcatc aatcccatca tctatgcctt cgttggggag aagttcagaa
1021 ggtatctctc ggtgttcttc cgaaagcaca tcaccaagcg cttctgcaaa caatgtccag
1081 ttttctacag ggagacagtg gatggagtga cttcaacaaa cacgccttcc actggggagc
1141 aggaagtctc ggctggttta taaaacgagg agcagtttga ttgttgttta taaagggaga
1201 taacaatctg tatataacaa caaacttcaa gggtttgttg aacaatagaa acctgtaaag
1261 caggtgccca ggaacctcag ggctgtgtgt actaatacag actatgtcac ccaatgcata
1321 tccaacatgt gctcagggaa taatccagaa aaactgtggg tagagacttt gactctccag
1381 aaagctcatc tcagctcctg aaaaatgcct cattaccttg tgctaatcct ctttttctag
1441 tcttcataat ttcttcactc aatctctgat tctgtcaatg tcttgaaatc aagggccagc
1501 tggaggtgaa gaagagaatg tgacaggcac agatgaatgg gagtgaggga tagtggggtc
1561 agggctgaga ggagaaggag ggagacatga gcatggctga gcctggacaa agacaaaggt
1621 gagcaaaggg ctcacgcatt cagccaggag atgatactgg tccttagccc catctgccac
1681 gtgtatttaa ccttgaaggg ttcaccaggt cagggagagt ttgggaactg caataacctg
1741 ggagttttgg tggagtccga tgattctctt ttgcataagt gcatgacata tttttgcttt
1801 attacagttt atctatggca cccatgcacc ttacatttga aatctatgaa atatcatgct
1861 ccattgttca gatgcttctt aggccacatc cccctgtcta aaaattcaga aaatttttgt
1921 ttataaaaga tgcattatct atgatatgct aatatatgta tatgcaatat aaaatttag
```

Figure 8C

SEQ ID NO. 7: Human Ccr2 gene isoform A:

```
   1 gtttatgaaa ttacagggct ggagacaaag atcacaatgt gaagacaaaa ttggagagcg
  61 gtcctaatca gccagagcaa aatttctggc tcttgctctt ccccatcctg ggttgaatca
 121 taggaacagg tggcaagatg ccagggtcag gagattccag aagtggcagc aagctcagtg
 181 ttaccaggtc agggatgacc tgtcttatta ttgaaatctc agagatatgc tccaattccg
 241 gcccagagac acattgagag acaactgggg aacttgctat gttcctgaac aggcaatgag
 301 ctgtcttcca agaaaaaacc tgagaccctt caagtctcag gtcttactta gcacatatac
 361 caggtcttac acaggacaca tggttacaac tgactgaaat ctgggctggg tgtaggagct
 421 cacacctgta atcccagccc ttcaggaggc tgaggcaggc agattgcctg agcccaggag
 481 ttcgagacca gcccgggcaa catgacaaaa ccccatctct acaaaaaata gtcaggcatg
 541 gtggcatgca cctgtagtct cagctacttg ggaggctgag atgagaggat tgcttgaggt
 601 tgagactgca gtgaagcatg atcatgccac cgcactccag cctaggcaac agagcaagat
 661 cttgtcgcaa aagaaagcaa aaacacaaca taacacaaca acaacaacaa caacaacaac
 721 agcaaaaaag ccaacttctt gaaatctgga aaggacacct ggactgccct gagcatttga
 781 ttgttgttgg ctctagcagt ggatgcatcc ttcaacctct ggcactctgc agggctcaga
 841 ctgttctgtt ctgtttgtta cctgtggagt gcctgccaga ccctgctcta gctgctttag
 901 gtccatttac cctcatagac ccccagtctt gttattcata tttcatattt gggaaatgga
 961 aacttagaaa cttgccaagt ccacagcatg agatcctgcc tccggtgtct gctggattcc
1021 agaaagtgcc aggggccaac ttagatgaca ccatgttctc tgcacaatct taggaatgct
1081 cctagtctga tgtccccatt gcaaaattta cattatcttt taacaaaacg tctttccaag
1141 gaggggcatt taaaataact gaggttcttc ttgctaagga agttcctgac acaagagata
1201 atttagcatt tccttttcat taaaaagttt gaaatcctgt aatttgtgat aatgtggatg
1261 aacctagagg atgttaagtg aaataagcca cacacagata gacaaatacc acgtgatctc
1321 actcttatgt ggaatttttt tttaaataag ttgcttagcc gggcatgatg gcacacacct
1381 gtaatcctag ctactcagga ggctgaggtg ggaggatggc ttgaactcag aaggtggagg
1441 ttgcagtgag ctgagactgt gccagtgcac tccggtctgg gtgacagaat gaaacccaat
1501 ttaaaaaaaa aaaaaaagtt gctatcttag aaaaagacag tagagcagtg gttaccagag
1561 actggggagg aaagagagga ggtgagaatg ggcagcagtt gatcaacggg tacaaagtta
1621 ccatgagata ggagaaacaa gtgctggtgc tctgctccaa gtagggtgac ggtagttaat
1681 aatgaattct gtatatataa atagctagaa gagagggttt tcaatatcat tattatttca
```

1741 aaagaaatga taaatgtttc agaggatgga tatgtaatta ccctgatttg atcattgcac
1801 aatgtataca tgtagcaaaa catcacattg tgtcccataa atatatacaa ttattatgtg
1861 aattaaataa aaaaaaattt taaagtctta tctaaatgaa atttctaacc agattctgaa
1921 tccatgatac cactgaaacc agcacacatg atcgcagtaa aacctcatta tacttcctcc
1981 actatcacca ataccctta ttctctggaa catgaaacat tctgttgtgc tcatatcatg
2041 caaattatca ctagtaggag agcagagagt ggaaatgttc caggtataaa gacccacaag
2101 ataaagaagc tcagagtcgt tagaaacagg agcagatgta cagggtttgc ctgactcaca
2161 ctcaaggttg cataagcaag atttcaaaat taatcctatt ctggagacct caacccaatg
2221 tacaatgttc ctgactggaa aagaagaact atatttttct gatttttttt tttcaaatct
2281 ttaccattag ttgccctgta tctccgcctt cactttctgc aggaaacttt atttcctact
2341 tctgcatacc aagtttctac ctctagatct gtttggttca gttgctgaga agcctgacat
2401 accaggactg cctgagacaa gccacaagct ggtgagttgt aggcattttt tccattactt
2461 tctgattcat aggctcaacg cacctcaaag ctggaaatgc cgggtctggg tacaccctgg
2521 ggaactgcaa agcctgcaca cttgggggga atgatcaaga tgagaggcag ggtggggat
2581 ggcatgtgca ccaggagatg ttagagaaac cctgaggaag agcagcgtgc agcaggtgat
2641 gggggagagt gggcagcaag cgaggccagg acagccactc tgctcagtca ccagtccaca
2701 cacccagggg ctcactctgc ccctctgagc acccaaggac gttaaagagc tggaactgtt
2761 agtctaaata taggaccatc caagctctga accaaaatgt gtcccttgcc tcaactcagg
2821 agatccacag aggcagaagt aaggaattta ttttctgaaa gatagatttc tatcagttct
2881 gggtgacatg ttctgacact tgaaatgaca cctaggacag cacatttcag gcatcttgct
2941 cattgttcac tgtagtagaa gctacatgct agccagttgt aaaaatgaaa ttaagtaatg
3001 tgtgcacagc atttaacata gcatctgagc ttcaggagca ctcaattaat gaccacagtt
3061 gtgattcttt aggcagatgc attttttcc aactttgatc agaggtctta tttagcttct
3121 ccagatttca agaatctggc tcagtgatat gaaatacaag acttgtgaaa agtgtcaatt
3181 gcaagagaaa tggaaggata aagtatacag gtgggtggaa aagaaattca cagtcactgc
3241 cagaaaaaaa attcttgaga atcaagtcct gatgatgtta gggcttatag ttcttattat
3301 aaagagtttt atgtactcat tcagtgaaca tttattggtg cctcctttag ccaggtacta
3361 tcataagagc tgaaaataga agcataatcc agtccttgat cttgaggaac atgctgtgtg
3421 tagcagataa cataataagt gcttatctag atgcatgcag tgttatgtga taagagtaat
3481 atgacagagg atacagatta ggcttcacag agaaggggga tttgagcagg aggtattgaa
3541 gggtgaatag aagctcacca atcattttgg gcagaggggc aaggacctgc aaaaccactg
3601 aagcatgaag gaaatggtga gtttagggaa aatgaagaga agatggctgt gactgaagca
3661 caggatttgg gattggagaa gggactggag gtgaggctga aaagaggcaa actcagaaaa
3721 gatgttgtgc tgggcagtct ggacattatc tttgaagccc accacatata agtcataggg
3781 ctactggagg ttttaagcta agagtgacta ttcaatttca acttaagaga agataggttg
3841 agagggaaca tggcttgaga tgagccatga gcaaaggaaa gactacaaca aagccaggag
3901 tgaggagtgt gtgaagcaag aaagtgacag ttgaaagcag tgcagagggg atgaatctga
3961 gaggcatcta tgaggtggaa ctcaaatgac atgataataa tacagggcat ttctctgtgt
4021 cagatgctgt cctaagtcct tactccattg atcttcacag caactcagca tagttaatat
4081 tttatgcata aagaaatcgg cacttgaagg agtaattggc cccagattac actgcctata
4141 aggattcaaa tccaggtttg tttggctcca aaaactggct cctaattttc agaaggagaa
4201 gcgacccagg gcaatgccca attttgcttc ttaggcaatg gaggaatcca caatcggaag
4261 gagttttcag cagtgcccca tttggggtgg gttgaatttg aggtccctgc atgataccca
4321 ctttgctcac ttcagtgcct aaaactgagt atggttcata gtaggtgttc aataagtgtt
4381 gatgcagtga atacatgcat ggggagatat gcatcaggca atgggaaatt caactctaag
4441 gcttagggga aagctggagc ttgaagacag agctttagaa aacagtagca tagaagggag
4501 taggaaccat gagtttagac aatacaattc aggaagaact ttgtagcaag gataaagagg
4561 caaaaaatta aagaggtgag agctaagtgt ggtgcctggg gaatcttaag gtgtgggcac
4621 ggggaggaga tgccagcaaa gaacatgaat aaaaagcggt agcacagccc ctcccatctg
4681 gaagccaaaa agaattgtaa atggaggaag ttagcagaag gatcaaatac ttgaagaggg
4741 tggaattgga ataaaaccag ggcatttgaa aaattgggtt gtcactgcaa tcttaacaag
4801 agaagttttg gcaggatgat ggaggcagaa agctgagaga atcatcagtt agaacgtttt
4861 tgacttcaga gaacagaaaa tgcagttcat aatggcttta aaacaggggc ttgtttttct
4921 cccagcaatt tgagaggcca aggcgggtgc atcaggaggt caagagaccg agaccatcct
4981 ggccaacatg gtgaatcccc atctctacta aaaatacaaa aattagcggg gcatggtggt
5041 gcacgcctat agtcccatct actcaggagg ctgaggcagg agaatcactt gaacccagga
5101 ggtggaggtt gcagtgagct gagatcatgg ccactgcact atagcctgga gacacagcga 5161 gactccgtct ccaaaaaaaa aaaaaaagaa ggcagaaggt gaatagttca agggtgggtt
5221 taggactcag tgataatagg attctgcctg gcttctcatg gttctctagg tcttccattc
5281 atggcaccat gccctcacta ggcatgctgc cagagcagga ggggcaggtg gagggttctc
5341 ttgtgtctgt cttatcaggg aagaagagct ttctcagaag cccccagcag actccctttt
5401 catattatgg tccagcaatg agtcacagac ctatgcacca cctgcaaagg agccagagaa
5461 aacaaacgcc cagcgctttt agcctgaaaa tgagaatctg gtttgctggg gaagataaag
5521 ggtgtcggaa aatggctgtt gggtaaatca ttgatgtctg ccactaggaa tgaaaggcaa
5581 atcaggaact ggcacacatg ctttcaggga gatggctgca agggagaggg caaagactgg
5641 gaagttgctt atgtggtgcc agactatttg gaagatcatg gattgcggtg tttgtgttgt
5701 gtggtcatca ttttgttctt tgtttacaga acagagaaag tggattgaac aaggacgcat
5761 ttccccagta catccacaac atgctgtcca catctcgttc tcggtttatc agaaatacca
5821 acgagagcgg tgaagaagtc accacctttt ttgattatga ttacggtgct ccctgtcata
5881 aatttgacgt gaagcaaatt ggggcccaac tcctgcctcc gctctactcg ctggtgttca
5941 tctttggttt tgtgggcaac atgctggtcg tcctcatctt aataaactgc aaaaagctga
6001 agtgcttgac tgacatttac ctgctcaacc tggccatctc tgatctgctt tttcttatta
6061 ctctcccatt gtgggctcac tctgctgcaa atgagtgggt ctttgggaat gcaatgtgca
6121 aattattcac aggcctgtat cacatcggtt attttggcgg aatcttcttc atcatcctcc
6181 tgacaatcga tagatacctg gctattgtcc atgctgtgtt tgctttaaaa gccaggacgg
6241 tcacctttgg ggtggtgaca agtgtgatca cctggttggt ggctgtgttt gcttctgtcc
6301 caggaatcat ctttactaaa tgccagaaag aagattctgt ttatgtctgt ggcccttatt
6361 ttccacgagg atggaataat ttccacacaa taatgaggaa cattttgggg ctggtcctgc
6421 cgctgctcat catggtcatc tgctactcgg gaatcctgaa aaccctgctt cggtgtcgaa
6481 acgagaagaa gaggcatagg gcagtgagag tcatcttcac catcatgatt gtttactttc
6541 tcttctggac tccctataat attgtcattc tcctgaacac cttccaggaa ttcttcggcc
6601 tgagtaactg tgaaagcacc agtcaactgg accaagccac gcaggtgaca gagactcttg
6661 ggatgactca ctgctgcatc aatcccatca tctatgcctt cgttggggag aagttcagaa
6721 ggtatctctc ggtgttcttc cgaaagcaca tcaccaagcg cttctgcaaa caatgtccag
6781 ttttctacag ggagacagtg gatggagtga cttcaacaaa cacgccttcc actggggagc
6841 aggaagtctc ggctggttta taaaacgagg agcagtttga ttgttgttta taaagggaga
6901 taacaatctg tatataacaa caaacttcaa gggtttgttg aacaatagaa acctgtaaag
6961 caggtgccca ggaacctcag ggctgtgtgt actaatacag actatgtcac ccaatgcata
7021 tccaacatgt gctcagggaa taatccagaa aaactgtggg tagagacttt gactctccag
7081 aaagctcatc tcagctcctg aaaaatgcct cattaccttg tgctaatcct ctttttctag
7141 tcttcataat ttcttcactc aatctctgat tctgtcaatg tcttgaaatc aagggccagc
7201 tggaggtgaa gaagagaatg tgacaggcac agatgaatgg gagtgaggga tagtggggtc
7261 agggctgaga ggagaaggag ggagacatga gcatggctga gcctggacaa agacaaaggt
7321 gagcaaaggg ctcacgcatt cagccaggag atgatactgg tccttagccc catctgccac
7381 gtgtatttaa ccttgaaggg ttcaccaggt cagggagagt ttgggaactg caataacctg
7441 ggagttttgg tggagtccga tgattctctt ttgcataagt gcatgacata tttttgcttt
7501 attacagttt atctatggca cccatgcacc ttacatttga aatctatgaa atatcatgct
7561 ccattgttca gatgcttctt aggccacatc cccctgtcta aaaattcaga aaatttttgt
7621 ttataaaaga tgcattatct atgatatgct aatatatgta tatgcaatat atataggctc
7681 ttgcttgatc tctccaggag gtagtgatta tgagaagggg gtggagaatg atgagttcct
7741 tcaccaggag caaaggacgg ggatcgtgtg gaaccactgc agaactattt ccgaaatcaa
7801 ctaagtggag agagccagga aggctgcatc agaacccagt aaagcttctt gtctggatct
7861 gagctggttt gttttgtgct tgcttttccc tgccttgcca ctcccctcac tcttctcttt
7921 tccccacagc ctttttcaca tagctcttgg ctgtaggatt gccccactcc aaaaaccagt
7981 gtgtggaggt ccaggagtga gaccaggaaa gaatgtgaaa gtgactacac aaggactcct
8041 cgatggtcgt ggaaaaggaa agtcaattgg cagagcccct gaagccagtc ttcaggacaa
8101 agaaggagcc tagagacaga aatgacagat ctctgctttg gaaatcacac gtctggcttc
8161 acagatgtgt gattcacagt gtgaatcttg gtgtctacgt taccaggcag gaaggctgag
8221 aggagagaga ctccagctgg gttggaaaac agtattttcc aaactacctt ccagttcctc
8281 atttttgaat acaggcatag agttcagact ttttttaaat agtaaaaata aaattaaagc
8341 tgaaaactgc aacttgtaaa tgtggtaaag agttagtttg agttactatc atgtcaaacg
8401 tgaaaatgct gtattagtca cagagataat tctagctttg agcttaagaa ttttgagcag
8461 gtggtatgtt tgggagactg ctgagtcaac ccaatagttg ttgattggca ggagttggaa
8521 gtgtgtgatc tgtgggcaca ttagcctatg tgcatgcagc atctaagtaa tgatgtcgtt

```
8581 tgaatcacag tatacgctcc atcgctgtca tctcagctgg atctccattc tctcaggctt
8641 gctgccaaaa gccttttgtg ttttgttttg tatcattatg aagtcatgcg tttaatcaca
8701 ttcgagtgtt tcagtgcttc gcagatgtcc ttgatgctca tattgttccc tattttgcca
8761 gtgggaactc ctaaatcaag ttggcttcta atcaaagctt ttaaacccta ttggtaaaga
8821 atggaaggtg gagaagctcc ctgaagtaag caaagacttt cctcttagtc gagccaagtt
8881 aagaatgttc ttatgttgcc cagtgtgttt ctgatctgat gcaagcaaga aacactgggc
8941 ttctagaacc aggcaacttg ggaactagac tcccaagctg gactatggct ctactttcag
9001 gccacatggc taaagaaggt ttcagaaaga agtggggaca gagcagaact ttcaccttca
9061 tatatttgta tgatcctaat gaatgcataa aatgttaagt tgatggtgat gaaatgtaaa
9121 tactgttttt aacaactatg atttggaaaa taaatcaatg ctataactat gttgataaaa
9181 gatttaaaaa caactggctg tttttttaca ctgtggtgtg gaagattgtg ttgtgttcac
9241 aacttttcac ttcttcccct gtgtgattac acacacctgc ccttgtggtg tgacttgcag
9301 tgcgccctac aggccacaca accccatgcc ctccaccact ggctctgctg ctggaatgtg
9361 agcagaagtg acatctgcct catccaagca gagcctcttg ctcagccaca ggaaggccca
9421 ttccagatca cacccgtcag cccgtgcgcc ctggtgaatg agaagacaca gggagctgca
9481 gccacatata acatgagcaa gaagtctgtg tttgctgtga taagccactg agttttaggg
9541 gttgtttgtt aagaagcaca aaaaccgatt aagacatgtg gtatatagtg acttcatata
9601 tagaatctgg aaaactatcc atttattttc aatcatggaa ttcaatatga caagcatccc
9661 ggagggtcta cctatgccag actgggttgg aaacagaaag acagatgtta atgccagtgt
9721 cctttacacc tccaagtcca gggccagctg tggagtggga ggggtagaga aggtcctgtg
9781 cacagtcaca gtgcgctgtg cagagcagga acagaggcat ctgtgaaaag tgctgagagc
9841 ctggaggaca gagtgactaa tgcaatgaca gtcttgcatc ataggaataa cagccacagc
9901 aggattttat tgctgccaaa gaaactgcca tttaaaaatt gccagccatc cgggaggctg
9961 aggcaggaga atggcatgaa tccaggaggc ggagcttgca gtgagccgag atcgggccac
10021 tgcactccag cctgggcaac agagccagac tccatctcaa aaaaaaaaaa aaa
```

Figure 8D

SEQ ID NO. 8: Human Ccr2 gene promoter:

```
   1 gcacacctgt aatcccagcc cttcaggagg ctgaggcagg cagattgcct gagcccagga
  61 gttcgagacc agcccgggca acatgacaaa accccatctc tacaaaaaat agtcaggcat
 121 ggtggcatgc acctgtagtc tcagctactt gggaggctga gatgagagga ttgcttgagg
 181 ttgagactgc actgaagcat gatcatgcca ccgcactcca gcctaggcaa cagagcaaga
 241 tcttgtcgca aaagaaagca aaaatacaac ataacacaac aacaacaaca acaacaacaa
 301 cagcaaaaaa gccaacttct tgaaatctgg aaaggacacc tccactgccc tcagcatttg
 361 attgttgttg gctctagcag tggatgcatc cttcaacctc tggcactctg caggggctca
 421 gactgttctg ttctgtttgt tacctgtgga gtgcctgcca gaccctgctc tagctgcttt
 481 aggtccattt accctcatag acccccagtc ttgttattca tatttcatat ttgggaaatg
 541 gaaacttaga aacttgccaa gtccacagca tgagatcctg cctccggtgt ctgctggatt
 601 ccagaaagtg ccagggggca acttagatga caccatgttc tctgcacaat cttaggaatg
 661 ctcctagtct gatgtcccca ttgcaaaatt tacattatct tttaacaaaa cgtctttcca
 721 aggaggggca tttaaaataa ctgaggttct tcttgctaag gacgttcctg acacaagaga
 781 taatttagca tttcctttc attaaaaagt ttgaaatcct gtaatttgtg ataatgtgga
 841 tgaacctaga ggatgttaag tgaaataagc cacacacaga tagacaaata ccacgtgatc
 901 tcactcttat gtggaatttt tttttaaata agttgcttag ccgggcatga tggcacacac
 961 ctgtaatcct agctactcag gaggctgagg tgggaggatg gcttgaactc agaaggtgga
1021 ggtagcagtg agctgagact gtgccagtgc actccggtct gggtgacaga atgaaaccca
1081 atttaaaaaa aaaaaaaaag ttgctatctt agaaaaagac agtagagcag tggttaccag
1141 agactgggga ggaaagagag gaggtgagaa tgggcagcag ttgatcaacg ggtacaaagt
1201 taccatgaga taggagaaac aagtgctggt gctctgctcc aagtagggtg acggtagtta
1261 ataatgaatt ctgtatatat aaatagctag aagagagggt tttcaatatc attattattt
1321 caaaagaaat gataaatgtt tcagaggatg gatatgtaat taccctgatt tgatcattgc
1381 acaatgtata catgtagcaa aacatcacat tgtgtcccat aaatatatac aattattatg
1441 tgaattaaat aaaaaaaaat tttaaagtct tatctaaatg aaatttctaa ccagattctg
1501 aatccatgat accactgaaa ccagcacaca tgatcgcagt aaaacctcat tatacttcct
1561 ccactatcac caataccctt tattctctgg aacatgaaac attctgttgt gctcatatca
```

```
1621 tgcaaattat cactagtagg agagcagaga gtggaaatgt tccaggtata aagacccaca
1681 agataaagaa gctcagagtc gttagaaaca ggagcagatg tacagggttt gcctgactca
1741 cactcaaggt tgcataagca agatttcaaa attaatccta ttctggagac ctcaacccaa
1801 tgtacaatgt tcctgactgg aaaagaagaa ctatattttt ctgatttttt ttttcaaatc
1861 tttaccatta gttgccctgt atctccgcct tcactttctg caggaaactt tatttcctac
1921 ttctgcatgc caagtttcta cctctagatc tgtttggttc agttgctgag aagcctgaca
1981 taccaggact gcctgagaca agccacaagc tggtgagttg taggcatttt ttccattact
2041 ttctgattca taggctcaac gcacctcaaa gctggaaatg cc
```

FIGURE 9
SEQ ID NO. 9: Human C5 receptor gene:

1 ctacctccaa ccatgggcct tttgggaata ctttgttttt taatcttcct ggggaaaacc
61 tggggacagg agcaaacata tgtcatttca gcaccaaaaa tattccgtgt tggagcatct
121 gaaaatattg tgattcaagt ttatggatac actgaagcat ttgatgcaac aatctctatt
181 aaaagttatc ctgataaaaa atttagttac tcctcaggcc atgttcattt atcctcagag
241 aataaattcc aaaactctgc aatcttaaca atacaaccaa aacaattgcc tggaggacaa
301 aacccagttt cttatgtgta tttggaagtt gtatcaaagc atttttcaaa atcaaaaaga
361 atgccaataa cctatgacaa tggatttctc ttcattcata cagacaaacc tgtttatact
421 ccagaccagt cagtaaaagt tagagtttat tcgttgaatg acgacttgaa gccagccaaa
481 agagaaactg tcttaacctt catagatcct gaaggatcag aagttgacat ggtagaagaa
541 attgatcata ttggaattat ctcttttcct gacttcaaga ttccgtctaa tcctagatat
601 ggtatgtgga cgatcaaggc taaatataaa gaggactttt caacaactgg aaccgcatat
661 tttgaagtta aagaatatgt cttgccacat ttttctgtct caatcgagcc agaatataat
721 ttcattggtt acaagaactt taagaatttt gaaattacta taaaagcaag atatttttat
781 aataaagtag tcactgaggc tgacgtttat atcacatttg gaataagaga agacttaaaa
841 gatgatcaaa aagaaatgat gcaaacagca atgcaaaaca caatgttgat aaatggaatt
901 gctcaagtca catttgattc tgaaacagca gtcaaagaac tgtcatacta cagtttagaa
961 gatttaaaca acaagtacct ttatattgct gtaacagtca tagagtctac aggtggattt
1021 tctgaagagg cagaaatacc tggcatcaaa tatgtcctct ctccctacaa actgaatttg
1081 gttgctactc ctcttttcct gaagcctggg attccatatc ccatcaaggt gcaggttaaa
1141 gattcgcttg accagttggt aggaggagtc ccagtaatac tgaatgcaca aacaattgat
1201 gtaaaccaag agacatctga cttggatcca agcaaaagtg taacacgtgt tgatgatgga
1261 gtagcttcct ttgtgcttaa tctcccatct ggagtgacgg tgctggagtt taatgtcaaa
1321 actgatgctc cagatcttcc agaagaaaat caggccaggg aaggttaccg agcaatagca
1381 tactcatctc tcagccaaag ttacctttat attgattgga ctgataacca taaggctttg
1441 ctagtgggag aacatctgaa tattattgtt acccccaaaa gcccatatat tgacaaaata
1501 actcactata attacttgat tttatccaag ggcaaaatta tccattttgg cacgagggag
1561 aaattttcag atgcatctta tcaaagtata aacattccag taacacagaa catggttcct
1621 tcatcccgac ttctggtcta ttatatcgtc acaggagaac agacagcaga attagtgtct
1681 gattcagtct ggttaaatat tgaagaaaaa tgtggcaacc agctccaggt tcatctgtct
1741 cctgatgcag atgcatattc tccaggccaa actgtgtctc ttaatatggc aactggaatg
1801 gattcctggg tggcattagc agcagtggac agtgctgtgt atggagtcca aagaggagcc
1861 aaaaagccct tggaaagagt atttcaattc ttagagaaga gtgatctggg ctgtggggca
1921 ggtggtggcc tcaacaatgc caatgtgttc cacctagctg gacttacctt cctcactaat
1981 gcaaatgcag atgactccca agaaaatgat gaaccttgta aagaaattct caggccaaga
2041 agaacgctgc aaaagaagat agaagaaata gctgctaaat ataaacattc agtagtgaag
2101 aaatgttgtt acgatggagc ctgcgttaat aatgatgaaa cctgtgagca gcgagctgca
2161 cggattagtt tagggccaag atgcatcaaa gctttcactg aatgttgtgt cgtcgcaagc
2221 cagctccgtg ctaatatctc tcataaagac atgcaattgg gaaggctaca catgaagacc
2281 ctgttaccag taagcaagcc agaaattcgg agttattttc cagaaagctg gttgtgggaa
2341 gttcatcttg ttcccagaag aaaacagttg cagtttgccc tacctgattc tctaaccacc
2401 tgggaaattc aaggcattgg catttcaaac actggtatat gtgttgctga tactgtcaag
2461 gcaaaggtgt tcaaagatgt cttcctggaa atgaatatac catattctgt tgtacgagga
2521 gaacagatcc aattgaaagg aactgtttac aactatagga cttctgggat gcagttctgt 2581 gttaaaatgt ctgctgtgga gggaatctgc acttcggaaa gcccagtcat tgatcatcag
2641 ggcacaaagt cctccaaatg tgtgcgccag aaagtagagg gctcctccag tcacttggtg
2701 acattcactg tgcttcctct ggaaattggc cttcacaaca tcaatttttc actggagact
2761 tggtttggaa aagaaatctt agtaaaaaca ttacgagtgg tgccagaagg tgtcaaaagg
2821 gaaagctatt ctggtgttac tttggatcct aggggtattt atggtaccat tagcagacga
2881 aaggagttcc catacaggat acccttagat ttggtcccca aaacagaaat caaaaggatt
2941 ttgagtgtaa aaggactgct tgtaggtgag atcttgtctg cagttctaag tcaggaaggc
3001 atcaatatcc taacccacct ccccaaaggg agtgcagagg cggagctgat gagcgttgtc
3061 ccagtattct atgtttttca ctacctggaa acaggaaatc attggaacat ttttcattct
3121 gacccattaa ttgaaaagca gaaactgaag aaaaaattaa aagaagggat gttgagcatt
3181 atgtcctaca gaaatgctga ctactcttac agtgtgtgga agggtggaag tgctagcact
3241 tggttaacag cttttgcttt aagagtactt ggacaagtaa ataaatacgt agagcagaac
3301 caaaattcaa tttgtaattc tttattgtgg ctagttgaga attatcaatt agataatgga
3361 tctttcaagg aaaattcaca gtatcaacca ataaaattac agggtacctt gcctgttgaa
3421 gcccgagaga acagcttata tcttacagcc tttactgtga ttggaattag aaaggctttc
3481 gatatatgcc ccctggtgaa aatcgacaca gctctaatta aagctgacaa ctttctgctt
3541 gaaaatacac tgccagccca gagcaccttt acattggcca tttctgcgta tgctctttcc
3601 ctgggagata aaactcaccc acagtttcgt tcaattgttt cagctttgaa gagagaagct
3661 ttggttaaag gtaatccacc catttatcgt ttttggaaag acaatcttca gcataaagac
3721 agctctgtac ctaacactgg tacggcacgt atggtagaaa caactgccta tgctttactc
3781 accagtctga acttgaaaga tataaattat gttaacccag tcatcaaatg gctatcagaa
3841 gagcagaggt atggaggtgg cttttattca acccaggaca ccatcaatgc cattgagggc
3901 ctgacggaat attcactcct ggttaaacaa ctccgcttga gtatggacat cgatgtttct
3961 tacaagcata aaggtgcctt acataattat aaaatgacag acaagaattt ccttgggagg
4021 ccagtagagg tgcttctcaa tgatgacctc attgtcagta caggatttgg cagtggcttg
4081 gctacagtac atgtaacaac tgtagttcac aaaaccagta cctctgagga agtttgcagc
4141 ttttatttga aaatcgatac tcaggatatt gaagcatccc actacagagg ctacggaaac
4201 tctgattaca aacgcatagt agcatgtgcc agctacaagc ccagcaggga agaatcatca
4261 tctggatcct ctcatgcggt gatggacatc tccttgccta ctggaatcag tgcaaatgaa
4321 gaagacttaa aagcccttgt ggaaggggtg gatcaactat tcactgatta ccaaatcaaa
4381 gatggacatg ttattctgca actgaattcg attccctcca gtgatttcct ttgtgtacga
4441 ttccggatat ttgaactctt tgaagttggg tttctcagtc ctgccacttt cacagtttac
4501 gaataccaca gaccagataa acagtgtacc atgttttata gcacttccaa tatcaaaatt
4561 cagaaagtct gtgaaggagc cgcgtgcaag tgtgtagaag ctgattgtgg gcaaatgcag
4621 gaagaattgg atctgacaat ctctgcagag acaagaaaac aaacagcatg taaaccagag
4681 attgcatatg cttataaagt tagcatcaca tccatcactg tagaaaatgt ttttgtcaag
4741 tacaaggcaa cccttctgga tatctacaaa actggggaag ctgttgctga gaaagactct
4801 gagattacct tcattaaaaa ggtaacctgt actaacgctg agctggtaaa aggaagacag
4861 tacttaatta tgggtaaaga agccctccag ataaaataca atttcagttt caggtacatc
4921 taccctttag attccttgac ctggattgaa tactggccta gagacacaac atgttcatcg
4981 tgtcaagcat ttttagctaa tttagatgaa tttgccgaag atatcttttt aaatggatgc
5041 taaaattcct gaagttcagc tgcatacagt ttgcacttat ggactcctgt tgttgaagtt
5101 cgtttttttg ttttcttctt tttttaaaca ttcatagctg gtcttatttg taaagctcac
5161 tttacttaga attagtggca cttgctttta ttagagaatg atttcaaatg ctgtaacttt
5221 ctgaaataac atggccttgg agggcatgaa gacagatact cctccaaggt tattggacac
5281 cggaaacaat aaattggaac acctcctcaa acctaccact caggaatgtt tgctggggcc 5341 gaaagaacag tccattgaaa gggagtatta caaaaacatg gcctttgctt gaaagaaaat
5401 accaaggaac aggaaactga tcattaaagc ctgagtttgc tttc

FIGURE 10

SEQ ID NO. 10: Human C5a receptor gene fragment

```
  1 ctacctccaa ccatgggcct tttgggaata ctttgttttt taatcttcct ggggaaaacc
 61 tggggacagg agcaaacata tgtcatttca gcaccaaaaa tattccgtgt tggagcatct
121 gaaaatattg tgattcaagt ttatggatac actgaagcat ttgatgcaac aatctctatt
181 aaaagttatc ctgataaaaa atttagttac tcctcaggcc at
```

Figure 10
SEQ ID NO. 10: Human C5a gene fragment:

1 ctacctccaa ccatgggcct tttgggaata ctttgttttt taatcttcct ggggaaaacc
61 tggggacagg agcaaacata tgtcatttca gcaccaaaaa tattccgtgt tggagcatct
121 gaaaatattg tgattcaagt ttatggatac actgaagcat ttgatgcaac aatctctatt
181 aaaagttatc ctgataaaaa atttagttac tcctcaggcc at

WDC99 826263-1.050229.0415

SEQUENCE LISTING

```
<160> NUMBER OF SEQ ID NOS: 10

<210> SEQ ID NO 1
<211> LENGTH: 757
<212> TYPE: DNA
<213> ORGANISM: Homo sapiens
```

-continued

<400> SEQUENCE: 1
ggaaccgaga ggctgagact aacccagaaa catccaattc tcaaactgaa gctcgcactc 60
tcgcctccag catgaaagtc tctgccgccc ttctgtgcct gctgctcata gcagccacct 120
tcattcccca agggctcgct cagccagatg caatcaatgc cccagtcacc tgctgttata 180
acttcaccaa taggaagatc tcagtgcaga ggctcgcgag ctatagaaga atcaccagca 240
gcaagtgtcc caaagaagct gtgatcttca agaccattgt ggccaaggag atctgtgctg 300
accccaagca gaagtgggtt caggattcca tggaccacct ggacaagcaa acccaaactc 360
cgaagacttg aacactcact ccacaaccca agaatctgca gctaacttat tttcccctag 420
ctttccccag acaccctgtt ttattttatt ataatgaatt ttgtttgttg atgtgaaaca 480
ttatgcctta agtaatgtta attcttattt aagttattga tgttttaagt ttatctttca 540
tggtactagt gtttttttaga tacagagact tggggaaatt gcttttcctc ttgaaccaca 600
gttctacccc tgggatgttt tgagggtctt tgcaagaatc attaatacaa agaatttttt 660
ttaacattcc aatgcattgc taaaatatta ttgtggaaat gaatattttg taactattac 720
accaaataaa tatatttttg tacaaaaaaa aaaaaaa 757

<210> SEQ ID NO 2
<211> LENGTH: 743
<212> TYPE: DNA
<213> ORGANISM: Homo sapiens

<400> SEQUENCE: 2
agactaaccc agaaacatcc aattctcaaa ctgaagctcg cactctcgcc tccagcatga 60
aagtctctgc cgcccttctg tgcctgctgc tcatagcagc caccttcatt ccccaagggc 120
tcgctcagcc agatgcaatc aatgccccag tcacctgctg ttataacttc accaatagga 180
agatctcagt gcagaggctc gcgagctata gaagaatcac cagcagcaag tgtcccaaag 240
aagctgtgat cttcaagacc attgtggcca aggagatctg tgctgacccc aagcagaagt 300
gggttcagga ttccatggac cacctggaca agcaaaccca aactccgaag acttgaacac 360
tcactccaca acccaagaat ctgcagctaa cttattttcc cctagctttc cccagacacc 420
ctgttttatt ttattataat gaattttgtt tgttgatgtg aaacattatg ccttaagtaa 480
tgttaattct tatttaagtt attgatgttt taagtttatc tttcatggta ctagtgtttt 540
ttagatacag agacttgggg aaattgcttt tcctcttgaa ccacagttct acccctggga 600
tgttttgagg gtctttgcaa gaatcattaa tacaaagaat tttttttaac attccaatgc 660
attgctaaaa tattattgtg gaaatgaata ttttgtaact attacaccaa ataaatatat 720
ttttgtacaa aaaaaaaaaa aaa 743

<210> SEQ ID NO 3
<211> LENGTH: 3221
<212> TYPE: DNA
<213> ORGANISM: Homo sapiens

<400> SEQUENCE: 3
ccgagatgtt cccagcacag ccccatgtga gagctccctg gctccgggcc cagtatctgg 60
aatgcaggct ccagccaaat gcattctctt ctacgggatc tgggaacttc caaagctgcc 120
tcctcagagt gggaatttcc actcacttct ctcacgccag cactgacctc ccagcggggg 180
agggcatctt ttcttgacag agcagaagtg ggaggcagac agctgtcact ttccagaaga 240

-continued

```
ctttcttttc tgattcatac ccttcacctt ccctgtgttt actgtctgat atatgcaaag    300
gccaagtcac tttccagaga tgacaactcc ttcctgaagt agagacatgc ttccaacact    360
cagaagccta tgtgaacact cagccagcaa agctgggaag tttttctctg tgaccatggg    420
ctaattggtc tccttctctg gattgtggct ttatcagata aaaacaagtg gtcatgccac    480
aggatgtcta taagcccatt gattctggga ttctatgagt gatgctgata tgactaagcc    540
aggagagact tatttaaaga tctcagcatc tttcagcttg ttaacctaga gaaaacccga    600
agcatgactg gattataaag ggaaattgaa tgcggtccac caagttcatg gtaaaggatg    660
cactaacaga ttagagagag gtttcccctg atatgaggaa aacttcttgg aagatgaggt    720
gagatggcct aggaagaaat tcctacacaa aattgcacag tctctagtcc tggaaacatt    780
ttattcattg gataagaatg gattgaggca tgagcagagg actgagacaa acacagagaa    840
gtttcaacac tggttgggga gaaaaggagt aactagtgag attcaggcag aacaagaata    900
aggctcctca agaggcacaa gcaaagcagg gctcgagttg atttgttctc tcttcatcct    960
gctttttgta attccaccag agtctgaaat gaccactcca tagagtctct gctctgggat   1020
tctccaggaa accaatatcc atcatgagac atcaagtcta gtcccaggaa gaagagattc   1080
tggaatggaa acatcctggg tgggagtctc agcacatcta ctattctgtc tgagttactg   1140
gacaaataac ttcagtttta acctaacgaa agctgggttg gttggaggac tgggcaggca   1200
gcgctggaaa gtatgtcagc accatacctg actccctgaa tgcactcaac aatgccatta   1260
ctgaccactt actagaaata aaacagtcat ttgttgaata caacccgttt ctttttacaa   1320
gtgtagtgaa aagtgttttc tttcaagaaa ccccatgcat ttatagacat tgcctcagtg   1380
accctttatg aaagaagtca ctagtctttg tatgcccatt gggcaagggc accgcaaggc   1440
tcagaaggag gaggcagtgg gctaggagaa tggagagatc agaattttaa actcagccca   1500
gccattaaca tgcctcaagt actcctatca tatttgtaag agacaacagt tcactgaaat   1560
gaattctaag gtctttgggt ttttatcagt gtgcttctgt agtttctgag gaaatctaag   1620
gcacaactga ggaatgaagt caggctttcc aattcccgaa atactcctcc actgcttact   1680
catgtccctt ggaaattaag aaggaagcca ggagaatagc tgccataacc agggatgaac   1740
ttcttgtcca ctgctgcctg ctatgctagc aacagcctcc taactcataa tgacttagcc   1800
atgaggaatg tttctagatt ctcctttagc tgtctgccca tttggaagat gctgaggaca   1860
gagagaggac ccaagcaggc aactagttgg aggacttgta cacgtttcct tccagcagta   1920
tgtcagagag gtgagcagcc cactggggac agggctgcct gggttctgtg ctcgagggga   1980
ccttgagcag gctatttaac ccttctgtgc ctcagttgcc tgatctataa catgaaaatt   2040
agcaatccct actagataaa gttggggaat ttacagagtt aatatttgta aaggtctgag   2100
aatattcctg gcagagtaag cactctgtga gtatgacact ggcatttctt ctgcagcact   2160
acatgctgtc tatgcctttg tccaagtctg aaaccctaga actcttagaa ttcagttcaa   2220
tgtttacaca atcctacagt tctgctaggc ttctatgatg ctactattct gcatttgaat   2280
gagcaaatgg atttaatgca ttgtcaggga gccggccaaa gcttgagagc tccttcctgg   2340
ctgggaggcc ccttggaatg tggcctgaag gtaagctggc agcgagcctg acatgctttc   2400
atctagtttc ctcgcttcct tccttttctg cagttttcgc ttcacagaaa gcagaatcct   2460
taaaaataac cctcttagtt cacatctgtg gtcagtctgg gcttaatggc accccatcct   2520
ccccatttgc tcatttggtc tcagcagtga atggaaaaag tgtctcgtcc tgaccccctg   2580
cttccctttc ctacttcctg gaaatccaca ggatgctgca tttgctcagc agatttaaca   2640
```

-continued

```
gcccacttat cactcatgga agatccctcc tcctgcttga ctccgccctc tctccctctg   2700

cccgctttca ataagaggca gagacagcag ccagaggaac cgagaggctg agactaaccc   2760

agaaacatcc aattctcaaa ctgaagctcg cactctcgcc tccagcatga aagtctctgc   2820

cgcccttctg tgcctgctgc tcatagcagc caccttcatt ccccaagggc tcgctcagcc   2880

aggtaaggcc ccctcttctt ctccttgaac cacattgtct tctctctgag ttatcatgga   2940

ccatccaagc agacgtggta cccacagtct tgctttaacg ctacttttcc aagataaggt   3000

gactcagaaa aggacaaggg gtgagcccaa ccacacagct gctgctcggc agagcctgaa   3060

ctagaattcc agctgtgaac cccaaatcca gctccttcca ggattccagc tctgggaaca   3120

cactcagcgc agttactccc ccagctgctt ccagcagagt ttggggatca gggtaatcaa   3180

agagagggtg ggtgtgtagg ctgtttccag acacgctgga g                       3221
```

<210> SEQ ID NO 4
<211> LENGTH: 11793
<212> TYPE: DNA
<213> ORGANISM: Homo sapiens

<400> SEQUENCE: 4

```
ggtacctcct ccagccttgg ccacagtgtc atccttgggc cccctaggtt tcagcctctt     60

gagtttgcac ttgcaggttt ggctgttgct ctcaaagcag gactattgca tcaacatggc    120

aggtgcagag gtcttcccgc ctcaatcgtc acccactgat ttctctgcca tggccttgaa    180

ctcaggcgac caatccagtt ggaacctccc cacactctcc gtggctaata attttggact    240

cagaagaaaa agcctcaatt tctctcctct caggaggtct cttggtcctt gagcaaatgt    300

atccatttct tctcctatct ccagtctttg ggcccccaaa ggtttttttc tccctttctc    360

caggacaatg agtgcctatt tacaagtgcc tgtttctact tgaataaggt ttctataaac    420

taagaagtgt tccttaggga cacaagtaac tggcactcct gttggaaaat gctaagatct    480

aggtcacgcg cacttccccc aacagacaca tacacacatt cacacacaca cacacacaca    540

cacacacaca cacacacaca cacacataca gcttgtctgc actctagcac tggcactgac    600

gctaacgcta taatcctggg caactttatt tccccatctt acattaagca gtggtgcagg    660

gattttcaac tctgggatct ctatcacacc tcccagctct gattgcttcc taatttacat    720

atttattgag catctgatgc taggtcctca tgctggtgat gcaggagtaa actagacaga    780

caaaagtccg tgccccacat tgtctgacac ctacacacct gctgttcgga ctccattaca    840

aacagctcca aggggaacag tgcacttgta aagtttctct cattaccatg gccacatccg    900

tgagcaataa ataagttgca tagttgaatt atttgataat gctttgtttt taactccctg    960

cacttaagtc agagatgtgt gtgctttgga aaactatttc tcctgactca ttagacaaat   1020

actatttgca tttttattca gcttccttcc tcagactcta atttacagta aaggcaagag   1080

gatttttgaa tggagccagt gctttgcaat gtggggctcc accagctagc cgactgaaat   1140

cattaataaa gaagcctttt taagtggctg aagtttcccc tttttggcat gcaacatttt   1200

gcaaccaagc ggaagaaaca tcatccgcaa agaagaatcc atgtggcccc tgaaaatcac   1260

tctctctgct acaggctccc cactccccag tgctcccctt agccctgcca ctatctctcc   1320

tccagatgga aaaagtgagg aactcaggga accaaaagtc ttgcttcttt actaatttcc   1380

ctgtctgaca ttaaatcatc ctacagttca gatatctggg ggaagtgact agagattctt   1440

gaactgttaa taattaattt aaatgatatt tgttaagaac ctacgacatg gaagatactg   1500
```

-continued

```
taccaggtgc tggggtccag catgggcaaa ggcctcaagg tggaatggag ctatggtgtg   1560
ttctggaagc agagagtggg gctgagggtg acatgaggtg aggagacagg agagggcctg   1620
gcagggtggg accttctggt gagagctggc tgctgtgtga ggagctgagg ccctggcttg   1680
attctggggt tacttctttg accttcagct ttttgtcatg ggcagacaga atggggatga   1740
aaaaaagctt aggaaatgga aacctcccta tgcattatat aataaaaatg gccaacacat   1800
tttcatagca agaaatcaca gcagaagctt gtactgggca tcaggactgt aggcatccaa   1860
tgcccagaaa ctggcatgtg ccctgggaca tcccctgaga aggcatgcca cgagccctca   1920
gactgacaca gctctttaca agttgcttac agagcactct tggtttatta attcatacaa   1980
gtctcatgac aatgtcagaa gcagctgtct tactaatccc ctttgacaga agaggcccag   2040
agaggtcaag ggacttgctc aaggccacac agctagaaag aggcagagcc aggcctttgg   2100
ccctggtgtt ctgacaccac ctggggctcc ttctgttatt ccatgctacc tcttctttct   2160
cttccgtatt cccttctcgt tcccttcctt cttgtgtctt gcttcttatc tgcctgtact   2220
tattcctgtt ggtgcctccc agctcagcca gcatagctct gtcttcaaat accccatgct   2280
tcattctggg gtcccataca cagtctgaca atcatctgag gggctgtgg gaggacatag   2340
aaaaaataca gctttacata gaaaaaaatg caaattgtag ccaggcgcag tggctcatgc   2400
ctgtaacccc agcactttgg gaggccgagg caggtggatc acctgaggtc aggagtctga   2460
gaccagcctg gccaatgtag taaaactcct tctctactaa aaatataaaa attagccagg   2520
cgtgatgtca tgtgcctgta gtcccagcta ctcgggaggc tgaggcagga gaacctcttg   2580
aatccaggag gcgcaggttg cagtgagcag agatagtgcc actgcactcc agcctgggtg   2640
acagagtgag actctgtctc aaaaaaataa aataaaataa aaaatgcaga ctgtgattca   2700
gcaggtctgg gttgaagccc agaactctct gataaattca atggcactta actacttgga   2760
ggtcatggat gcctttgcta atctaataga agctactgac cctctctcca gaaaaatgca   2820
caaaaacata aatgtggaag acaactcctg atggatctgg gagcctatcc aagggccaca   2880
gacaagagtc ctggtctgga caaaatgagc tgctcagtat tttcccacct ggccagcatt   2940
tcctatccaa agacaaatgt taaagttgtt ctagcagagc catgcaccag cagcagtatc   3000
atcacctggg aaccggttag caatgcagaa ccgcaggccc accccaaacc tacagtcaga   3060
atctctactt tagcaagatc ctaaggagat gggtaagcac attacaattt gcaacctttg   3120
taagtttgcc caaaatgtga cccctccttc acccaccgat cgccaaggtt caaaaatctg   3180
cccaaccctt gagcccatct taaatgtacc atcacgagcc ttccctgggc ccctcagctg   3240
ggactctcac cgctctgtat ctttctggtt aatgcaatta ttctgttccc ttagatgacc   3300
ccagcacagg tgctaaagga gtcaacaaaa ggctattgtc aaaaaagtgt ttctgtctcc   3360
actccatctg atctctgttt ccctaagacc tgcccatccc cctctcccag ttcggcacct   3420
tgaccccctc atcacactgc tcaggccacc ttgtacaatg caagccccaa atgaggaaag   3480
cattttctcc cccaatgtgt aacacgaaag tgctgtagag tggctcacgc tgcctttagc   3540
ctaagaattt atttaactct tacccccaac ccacatcagt ctcctccctc tagggctcag   3600
gtgctaatct gtgagggctg gctcagaaga caatctaaag aacaagcctc ttgcttcctc   3660
aggcatcact actcctcacc accatcaccc ccacccacca actcaggcca ctactctttc   3720
tgttctcata tgctatgccc atcgccaccc ctattcccat gctcaggagt attcttggct   3780
actgcatgca attagacctg gggcagatcc aatccagaaa gcaagaaatc ttagatgctg   3840
gaagcttggg gtaagtactg atcagattta ttcctaaatt cagtcctact ttccatggat   3900
```

-continued

```
tcttacttta gcatctcttc tgaaaaggaa gcatcatgtc taattcactt ctccctccct   3960
gtgcagtcct ctacctggtg ctctgcacag ggtatgtgct aattgtatga atgttataat   4020
aaagagatag tgcagtagat gacaaagggc actacattga gagcccagaa ataagcaaac   4080
cagcacaaat gtagccattc gtcttctatc tcaccttgag cctgtcacta acctgttcat   4140
ggcctcagtc tccccatcag agaaacaggt agatggtctc taaggtctcg ttcattttct   4200
gacattctgt gaaaaattaa ggaaagattt tcatccttga caggaaaggg attgcagagt   4260
agcggccctg ggaaaatggg ctctattcta cctggagcta gcctggagga gaggccttga   4320
gtgggggttg tctagaaagg acatggtgag tgcagagcta cggtgcatct ctcttgaagg   4380
ctgagtgaag ggagcaccag caagggagcc tgcactaggt ggggagggac aagtgaaccg   4440
cagaagttgg tgggagccca ggcagtggct tcagatcttt ccagagagct cacttttact   4500
tcctcttttt ttcacccctg acactgagtg ggagtctgca gcgatgacca aggttcatgc   4560
agaggatctt agtggtgggg tcagaccccg ggaggaatga agaaagcatt attcaccaag   4620
aggagctttt ccattcttta tctatgagtt gatagagagg aggccccggg gtaactgagg   4680
attctggaca gcatcagagc attgaccctc attttcccca tagcccctct gggggccttt   4740
cccttgtgtg tccccaagcg agagtccaac caaggtttgt gccagagcct aacccaggct   4800
tgtgccgaga tgttcccagc acagccccat gtgagagctc cctggctccg ggcccagtat   4860
ctggaatgca ggctccagcc aaatgcattc tcttctacgg gatctgggaa cttccaaagc   4920
tgcctcctca gagtgggaat ttccactcac ttctctcacg ccagcactga cctcccagcg   4980
ggggagggca tcttttcttg acagagcaga agtgggaggc agacagctgt cactttccag   5040
aagactttct tttctgattc atacccttca ccttccctgt gtttactgtc tgatatatgc   5100
aaaggccaag tcactttcca gagatgacaa ctccttcctg aagtagagac atgcttccaa   5160
cactcagaag cctatgtgaa cactcagcca gcaaagctgg gaagtttttc tctgtgacca   5220
tgggctaatt ggtctccttc tctggattgt ggctttatca gataaaaaca agtggtcatg   5280
ccacaggatg tctataagcc cattgattct gggattctat gagtgatgct gatatgacta   5340
agccaggaga gacttattta aagatctcag catctttcag cttgttaacc tagagaaaac   5400
ccgaagcatg actggattat aaagggaaat tgaatgcggt ccaccaagtt catggtaaag   5460
gatgcactaa cagattagag agaggtttcc cctgatatga ggaaaacttc ttggaagatg   5520
aggtgagatg gcctaggaag aaattcctac acaaagttgc acagtctcta gtcctggaaa   5580
cattttattc attggataag aatggattga ggcatgagca gaggactgag acaaacacag   5640
agaagtttca acactggttg gggagaaaag gagtaactag tgagattcag gcagaacaag   5700
aataaggctc ctcaagaggc acaagcaaag cagggctcga gttgatttgt tctctcttca   5760
tcctgctttt tgtaattcca ccagagtctg aaatggccac tccatagagt ctctgctctg   5820
ggattctcca ggaaaccaat atccatcatg agacatcaag tctagtccca ggaagaagag   5880
attctggaat ggaaacatcc tgggtgggag tctcagcaca tctactattc tgtctgagtt   5940
actggacaaa taacttcagt tttaacctaa cgaaagctgg gttggttgga ggactgggca   6000
ggcagcgctg gaaagtatgt cagcaccata cctgactccc tgaatgcact caacaatgcc   6060
attactgacc acttactaga aataaaacag tcatttgttg aatacaaccc gtttcttttt   6120
acaagtgtag tgaaaagtgt tttctttcaa gaaaccccat gcatttatag acattgcctc   6180
agtgaccctt tatgaaagaa gtcactagtc tttgtatgcc cattgggcaa gggcaccgca   6240
```

-continued

```
aggctcagaa ggaggaggca gtgggctagg agaatcgaga gatcagaatt ttaaactcag   6300
cccagccatt aacatgcctc aagtactcct atcatatttg taagagacaa cagttcactg   6360
aaatgaattc taaggtcttt gggtttttat cagtgtgctt ctgtagtttc tgaggaaatc   6420
taaggcacaa ctgaggaatg aagtcaggct ttccaattcc cgaaatactc ctccactgct   6480
tactcatgtc ccatggaaat taagaaggaa gccaggagaa tagctgccat aaccagggat   6540
gaacttcttg tccactgctg cctgctatgc tagcaacagc ctcctaactc ataatgactt   6600
agccatgagg aatgtttcta gattctcctt tagctgtctg cccatttgga agatgctgag   6660
gacagagaga ggacccaagc aggcaactag ttggaggact tgtacacgtt tccttccagc   6720
agtatgtcag agaggtggca gcccactggg gacagggctg cctgggttct gtgctcgagg   6780
ggaccttgag caggctattt aacccttctg tgcctcagtt gcctgatcta taacatgaaa   6840
attagcaatc cctactagat aaagttgggg aatttacaga gttaatattt gtaaaggtct   6900
gagaatattc ctggcagagt aagcactctg tgagtatgac actggcattt cttctgcagc   6960
actacatgct gtctatgcct ttgtccaagt ctgaaaccct agaactctta gaattcagtt   7020
caatgtttac acaatcctac agttctgcta ggcttctatg atgctactat tctgcatttg   7080
aatgagcaaa tggatttaat gcattgtcag ggagccggcc aaagcttgag agctccttcc   7140
tggctgggag gccccttgga atgtggcctg aaggtaagct ggcagcgagc ctgacatgct   7200
ttcatctagt ttcctcgctt ccttcctttt ctgcagtttt cgcttcacag aaagcagaat   7260
ccttaaaaat aaccctctta gttcacatct gtggtcagtc tgggcttaat ggcaccccat   7320
cctccccatt tgctcatttg gtctcagcag tgaatggaaa aagtgtctcg tcctgacccc   7380
ctgcttccct ttcctacttc ctggaaatcc acaggatgct gcatttgctc agcagattta   7440
acagcccact tatcactcat ggaagatccc tcctcctgct tgactccgcc ctctctccct   7500
ctgcccgctt tcaataagag gcagagacag cagccagagg aaccgagagg ctgagactaa   7560
cccagaaaca tccaattctc aaactgaagc tcgcactctc gcctccagca tgaaagtctc   7620
tgccgccctt ctgtgcctgc tgctcatagc agccaccttc attccccaag ggctcgctca   7680
gccaggtaag gccccctctt cttctccttg aaccacattg tcttctctct gagttatcat   7740
ggaccatcca agcagacgtg gtacccacag tcttgcttta acgctacttt tccaagataa   7800
ggtgactcag aaaaggacaa ggggtgagcc caaccacaca gctgctgctc ggcagagcct   7860
gaactagaat tccagctgtg aaccccaaat ccagctcctt ccaggattcc agctctggga   7920
acacactcag cgcagttact cccccagctg cttccagcag agtttgggga tcagggtaat   7980
caaagagagg gtgggtgtgt aggctgtttc cagacacgct ggagacccag aatctggtct   8040
gtgcttcatt caccttagct tccagagacg gtgactctgc agaggtaatg agtatcaggg   8100
aaactcatga ccaggcatag cctattcaga gtctaaaagg aggctcatag tggggctccc   8160
cagctgatct tccctggtgc tgatcatctg gattattggt ccgtcttaat gacacttgta   8220
ggcattatct agctttaact ctgtccatta tcaatgttat atacccattt tacagcatag   8280
gaaactgagt cattgggtca aagatcacat tctagctctg aggtataggc agaagcactg   8340
ggatttaatg agctctttct cttctcctgc ctgccttttg ctttttcctc atgactcttt   8400
tctgctctta agatcagaat aatccagttc atcctaaaat gctttttctt tgtggtttat   8460
tttccagatg caatcaatgc cccagtcacc tgctgctata acttcaccaa taggaagatc   8520
tcagtgcaga ggctcgcgag ctatagaaga atcaccagca gcaagtgtcc caaagaagct   8580
gtgatgtgag ttcagcacac caaccttccc tggcctgaag ttcttccttg tggagcaagg   8640
```

-continued

```
gacaagcctc ataaacctag agtcagagag tgcactattt aacttaatgt acaaaggttc   8700
ccaatgggaa aactgaggca ccaagggaaa aagtgaaccc caacatcact ctccacctgg   8760
gtgcctattc agaacacccc aatttcttta gcttgaagtc aggatggctc cacctggaca   8820
cctataggag cagtttgccc tgggttccct ccttccacct gcgttcctcc tctagctccc   8880
atggcagccc tttggtgcag aatgggctgc acttctagac caaaactgca aaggaacttc   8940
atctaactct gtcctccctc cccacagctt caagaccatt gtggccaagg agatctgtgc   9000
tgaccccaag cagaagtggg ttcaggattc catggaccac ctggacaagc aaacccaaac   9060
tccgaagact tgaacactca ctccacaacc caagaatctg cagctaactt attttcccct   9120
agctttcccc agacaccttg ttttatttta ttataatgaa ttttgtttgt tgatgtgaaa   9180
cattatgcct taagtaatgt taattcttat ttaagttatt gatgttttaa gtttatcttt   9240
catggtacta gtgtttttta gatacagaga cttggggaaa ttgcttttcc tcttgaacca   9300
cagttctacc cctgggatgt tttgagggtc tttgcaagaa tcattaatac aaagaatttt   9360
ttttaacatt ccaatgcatt gctaaaatat tattgtggaa atgaatattt tgtaactatt   9420
acaccaaata aatatatttt tgtacaaaac ctgacttcca gtgttttctt gaaggaaatt   9480
acaaagctga gagtatgagc ttggtggtga caaaggaaca tgatttcaga gggtggggct   9540
tacattttga aggaatggga aagtggattg gccccggtct tctccactgg gtggtctcct   9600
ctgagtctcc gtagaagaat ctttatggca ggccagttag gcattaaagc accacccttc   9660
cagtcttcaa cataagcagc ccagagtcca atgaccctgg tcacccattt agcaagagcc   9720
caaccccat tccttttctc acagaccctg acccctgcat gcaattcttc ccttaacata   9780
ttgcaactgc cccctaactg ggctacccac cccccaatct gtacctctcc aattaatacc   9840
ccaacctgga gtaatacaga cactgccagt attaggaaat aaggaaagag ttaatcacca   9900
tagataagat gattagattg aagtttcata gagatgatga gacctgaact tattatttat   9960
gaatgaagaa ggcttttcta ggaaaattat aggatcatta agaaaggaga aggaagagtg  10020
ggagcaaata cctggaggta gaaatggtga tgatgtgtac atcaagcagg gagaaaacca  10080
atgaaccaga tgcgaattcg ggcccacacc aatgtcaagg gatgacaatt agaaaggaag  10140
gttgagtcaa gggatttgaa tgttagggtg aaaagttact actcaactct gtaggttaaa  10200
aggaaacgtt gagaatcttc agtccaatga ggagggatgt gccatgttta gagattcaga  10260
gataagtttc aggaaatgta acttatagat tttatacata cacagagaaa tacggactag  10320
tgagaagcta ttgccatggt ccaagcaaga gatgatgaag gcctaaatat ggagccaaag  10380
aggcagcaat gaagaatgag ccatgcaggg tgaaatgctg catgttgtaa atggaggaga  10440
aagacctgtg acttcagata tgaaaacctc atcttcaacc cacattttaa gggggcagct  10500
tccctgaaac cagaatgtgt ttccctccat tactataccc ccatcccaat ctcaggcacc  10560
tggaatcatc catttaaaca gatgagcctt ctattcctaa atagccacct gaagtgtgta  10620
ttcctttgca tgatatttgt cccacctaaa gcattcgacc tgcctgggca cccacaccac  10680
gccaacactc aggaaagcag atgtcttgct ctgttgaata aactgcatgg ttcttaactt  10740
cccagtctgg tggggaaatg accactgtgt caacctagag caggcagtgc ttttggcagc  10800
atgaggtgct ggggacaact ttgactggca agaagcacac tcaggttctc accccgcatc  10860
cagcgctgac tcgctttgtc agtcaagaca ggtcagatat tctgagccta catcgatcat  10920
acaggtatga taatgtgtta caaataggaa cccagaggaa aggttccctt tcggatctgg  10980
```

-continued

```
gagcacatct gttggaaaac ttccatttct actaactgga gttgcagagg gagagaaggg  11040

attctgcttc tacattcctg agccagtcca gggtccctga atcagactac cgaatccctt  11100

caaagctcca agtaccctga tatatcagtc agcagacaat ttattgacag ctatttagaa  11160

aactcactga ccctcactcc aggtcaagca gcgtcccctg cctctcctct acccctacat  11220

tccctggcct tgatcaccag tcaggagtga aatctcaaat tgcagtagat gccaagaggc  11280

aaaaagagaa tagaatgcaa acaaatgaga cctcatcata tggcttccga gcagcaacct  11340

tttgacgcca ggcagatttg aggcagacag tctgggagga gaggaggcag agaaaggggg  11400

gatccacatg ctcaaacccc aaattaatct gcttacattc cccttgcagg ccacatctct  11460

tcattttcag gaagtcttga ctccatactg ttttccaccc aagcatggaa ttcctttcat  11520

gatgaaactg aacacagggc attggcagtg gtgagactct gttttagaag aaagtgccaa  11580

gtgcaatgca ttcatttcct gttgctgcca acaatcagtt ccaggaaatc taggcttttt  11640

atgtcatgct caaaattctt ccagcctatg ctcattattc aaatccaaag ccacatccac  11700

atctgtaggt gttagttaca gaagcaccat atttccaggt accaaaatct gtattagttt  11760

cttattgtta ctgtaacaaa ttcccataag ctt                               11793


<210> SEQ ID NO 5
<211> LENGTH: 2273
<212> TYPE: DNA
<213> ORGANISM: Homo sapiens

<400> SEQUENCE: 5

caggactgcc tgagacaagc cacaagctga acagagaaag tggattgaac aaggacgcat     60

ttccccagta catccacaac atgctgtcca catctcgttc tcggtttatc agaaatacca    120

acgagagcgg tgaagaagtc accacctttt ttgattatga ttacggtgct ccctgtcata    180

aatttgacgt gaagcaaatt ggggcccaac tcctgcctcc gctctactcg ctggtgttca    240

tctttggttt tgtgggcaac atgctggtcg tcctcatctt aataaactgc aaaaagctga    300

agtgcttgac tgacatttac ctgctcaacc tggccatctc tgatctgctt tttcttatta    360

ctctcccatt gtgggctcac tctgctgcaa atgagtgggt ctttgggaat gcaatgtgca    420

aattattcac agggctgtat cacatcggtt attttggcgg aatcttcttc atcatcctcc    480

tgacaatcga tagatacctg gctattgtcc atgctgtgtt tgctttaaaa gccaggacgg    540

tcacctttgg ggtggtgaca agtgtgatca cctggttggt ggctgtgttt gcttctgtcc    600

caggaatcat ctttactaaa tgccagaaag aagattctgt ttatgtctgt ggcccttatt    660

ttccacgagg atggaataat ttccacacaa taatgaggaa cattttgggg ctggtcctgc    720

cgctgctcat catggtcatc tgctactcgg gaatcctgaa aaccctgctt cggtgtcgaa    780

acgagaagaa gaggcatagg gcagtgagag tcatcttcac catcatgatt gtttactttc    840

tcttctggac tccctataac attgtcattc tcctgaacac cttccaggaa ttcttcggcc    900

tgagtaactg tgaaagcacc agtcaactgg accaagccac gcaggtgaca gagactcttg    960

ggatgactca ctgctgcatc aatcccatca tctatgcctt cgttggggag aagttcagaa   1020

gcctttttca catagctctt ggctgtagga ttgccccact ccaaaaacca gtgtgtggag   1080

gtccaggagt gagaccagga aagaatgtga aagtgactac acaaggactc ctcgatggtc   1140

gtggaaaagg aaagtcaatt ggcagagccc ctgaagccag tcttcaggac aaagaaggag   1200

cctagagaca gaaatgacag atctctgctt tggaaatcac acgtctggct tcacagatgt   1260

gtgattcaca gtgtgaatct tggtgtctac gttaccaggc aggaaggctg agaggagaga   1320
```

-continued gactccagct gggttggaaa acagtatttt ccaaactacc ttccagttcc tcatttttga 1380
atacaggcat agagttcaga ctttttttaa atagtaaaaa taaaattaaa gctgaaaact 1440
gcaacttgta aatgtggtaa agagttagtt tgagttgcta tcatgtcaaa cgtgaaaatg 1500
ctgtattagt cacagagata attctagctt tgagcttaag aattttgagc aggtggtatg 1560
tttgggagac tgctgagtca acccaatagt tgttgattgg caggagttgg aagtgtgtga 1620
tctgtgggca cattagccta tgtgcatgca gcatctaagt aatgatgtcg tttgaatcac 1680
agtatacgct ccatcgctgt catctcagct ggatctccat tctctcaggc ttgctgccaa 1740
aagccttttg tgttttgttt tgtatcatta tgaagtcatg cgtttaatca cattcgagtg 1800
tttcagtgct tcgcagatgt ccttgatgct catattgttc cctaatttgc cagtgggaac 1860
tcctaaatca aattggcttc taatcaaagc ttttaaaccc tattggtaaa gaatggaagg 1920
tggagaagct ccctgaagta agcaaagact ttcctcttag tcgagccaag ttaagaatgt 1980
tcttatgttg cccagtgtgt ttctgatctg atgcaagcaa gaaacactgg gcttctagaa 2040
ccaggcaact tgggaactag actcccaagc tggactatgg ctctactttc aggccacatg 2100
gctaaagaag gtttcagaaa gaagtgggga cagagcagaa ctttcacctt catatatttg 2160
tatgatccta atgaatgcat aaaatgttaa gttgatggtg atgaaatgta aatactgttt 2220
ttaacaacta tgatttggaa aataaatcaa tgctataact atgttgataa aag 2273

<210> SEQ ID NO 6
<211> LENGTH: 1979
<212> TYPE: DNA
<213> ORGANISM: Homo sapiens

<400> SEQUENCE: 6
caggactgcc tgagacaagc cacaagctga acagagaaag tggattgaac aaggacgcat 60
ttccccagta catccacaac atgctgtcca catctcgttc tcggtttatc agaaatacca 120
acgagagcgg tgaagaagtc accacctttt ttgattatga ttacggtgct ccctgtcata 180
aatttgacgt gaagcaaatt ggggcccaac tcctgcctcc gctctactcg ctggtgttca 240
tctttggttt tgtgggcaac atgctggtcg tcctcatctt aataaactgc aaaaagctga 300
agtgcttgac tgacatttac ctgctcaacc tggccatctc tgatctgctt tttcttatta 360
ctctcccatt gtgggctcac tctgctgcaa atgagtgggt ctttgggaat gcaatgtgca 420
aattattcac agggctgtat cacatcggtt attttggcgg aatcttcttc atcatcctcc 480
tgacaatcga tagatacctg gctattgtcc atgctgtgtt tgctttaaaa gccaggacgg 540
tcacctttgg ggtggtgaca agtgtgatca cctggttggt ggctgtgttt gcttctgtcc 600
caggaatcat ctttactaaa tgccagaaag aagattctgt ttatgtctgt ggcccttatt 660
ttccacgagg atggaataat ttccacacaa taatgaggaa cattttgggg ctggtcctgc 720
cgctgctcat catggtcatc tgctactcgg gaatcctgaa aaccctgctt cggtgtcgaa 780
acgagaagaa gaggcatagg gcagtgagag tcatcttcac catcatgatt gtttactttc 840
tcttctggac tccctataac attgtcattc tcctgaacac cttccaggaa ttcttcggcc 900
tgagtaactg tgaaagcacc agtcaactgg accaagccac gcaggtgaca gagactcttg 960
ggatgactca ctgctgcatc aatcccatca tctatgcctt cgttggggag aagttcagaa 1020
ggtatctctc ggtgttcttc cgaaagcaca tcaccaagcg cttctgcaaa caatgtccag 1080
ttttctacag ggagacagtg gatggagtga cttcaacaaa cacgccttcc actggggagc 1140

-continued

```
aggaagtctc ggctggttta taaaacgagg agcagtttga ttgttgttta taaagggaga   1200

taacaatctg tatataacaa caaacttcaa gggtttgttg aacaatagaa acctgtaaag   1260

caggtgccca ggaacctcag ggctgtgtgt actaatacag actatgtcac ccaatgcata   1320

tccaacatgt gctcagggaa taatccagaa aaactgtggg tagagacttt gactctccag   1380

aaagctcatc tcagctcctg aaaaaatgcct cattaccttg tgctaatcct ctttttctag   1440

tcttcataat ttcttcactc aatctctgat tctgtcaatg tcttgaaatc aagggccagc   1500

tggaggtgaa gaagagaatg tgacaggcac agatgaatgg gagtgaggga tagtggggtc   1560

agggctgaga ggagaaggag ggagacatga gcatggctga gcctggacaa agacaaaggt   1620

gagcaaaggg ctcacgcatt cagccaggag atgatactgg tccttagccc catctgccac   1680

gtgtatttaa ccttgaaggg ttcaccaggt cagggagagt ttgggaactg caataacctg   1740

ggagttttgg tggagtccga tgattctctt ttgcataagt gcatgacata tttttgcttt   1800

attacagttt atctatggca cccatgcacc ttacatttga aatctatgaa atatcatgct   1860

ccattgttca gatgcttctt aggccacatc cccctgtcta aaaattcaga aaatttttgt   1920

ttataaaaga tgcattatct atgatatgct aatatatgta tatgcaatat aaaatttag    1979
```

<210> SEQ ID NO 7
<211> LENGTH: 10073
<212> TYPE: DNA
<213> ORGANISM: Homo sapiens

<400> SEQUENCE: 7

```
gtttatgaaa ttacagggct ggagacaaag atcacaatgt gaagacaaaa ttggagagcg     60

gtcctaatca gccagagcaa aatttctggc tcttgctctt ccccatcctg ggttgaatca    120

taggaacagg tggcaagatg ccagggtcag gagattccag aagtggcagc aagctcagtg    180

ttaccaggtc agggatgacc tgtcttatta ttgaaatctc agagatatgc tccaattccg    240

gcccagagac acattgagag acaactgggg aacttgctat gttcctgaac aggcaatgag    300

ctgtcttcca agaaaaaacc tgagaccctt caagtctcag gtcttactta gcacatatac    360

caggtcttac acaggacaca tggttacaac tgactgaaat ctgggctggg tgtaggagct    420

cacacctgta atcccagccc ttcaggaggc tgaggcaggc agattgcctg agcccaggag    480

ttcgagacca gcccgggcaa catgacaaaa ccccatctct acaaaaaata gtcaggcatg    540

gtggcatgca cctgtagtct cagctacttg ggaggctgag atgagaggat tgcttgaggt    600

tgagactgca gtgaagcatg atcatgccac cgcactccag cctaggcaac agagcaagat    660

cttgtcgcaa aagaaagcaa aaacacaaca taacacaaca acaacaacaa caacaacaac    720

agcaaaaaag ccaacttctt gaaatctgga aaggacacct ggactgccct gagcatttga    780

ttgttgttgg ctctagcagt ggatgcatcc ttcaacctct ggcactctgc agggctcaga    840

ctgttctgtt ctgtttgtta cctgtggagt gcctgccaga ccctgctcta gctgctttag    900

gtccatttac cctcatagac ccccagtctt gttattcata tttcatattt gggaaatgga    960

aacttagaaa cttgccaagt ccacagcatg agatcctgcc tccggtgtct gctggattcc   1020

agaaagtgcc aggggccaac ttagatgaca ccatgttctc tgcacaatct taggaatgct   1080

cctagtctga tgtccccatt gcaaaattta cattatcttt taacaaaacg tctttccaag   1140

gaggggcatt taaaataact gaggttcttc ttgctaagga agttcctgac acaagagata   1200

atttagcatt tccttttcat taaaaagttt gaaatcctgt aatttgtgat aatgtggatg   1260

aacctagagg atgttaagtg aaataagcca cacacagata gacaaatacc acgtgatctc   1320
```

-continued

```
actcttatgt ggaatttttt tttaaataag ttgcttagcc gggcatgatg gcacacacct   1380
gtaatcctag ctactcagga ggctgaggtg ggaggatggc ttgaactcag aaggtggagg   1440
ttgcagtgag ctgagactgt gccagtgcac tccggtctgg gtgacagaat gaaacccaat   1500
ttaaaaaaaa aaaaaaagtt gctatcttag aaaaagacag tagagcagtg gttaccagag   1560
actggggagg aaagagagga ggtgagaatg ggcagcagtt gatcaacggg tacaaagtta   1620
ccatgagata ggagaaacaa gtgctggtgc tctgctccaa gtagggtgac ggtagttaat   1680
aatgaattct gtatatataa atagctagaa gagagggttt tcaatatcat tattatttca   1740
aaagaaatga taaatgtttc agaggatgga tatgtaatta ccctgatttg atcattgcac   1800
aatgtataca tgtagcaaaa catcacattg tgtcccataa atatatacaa ttattatgtg   1860
aattaaataa aaaaaaattt taaagtctta tctaaatgaa atttctaacc agattctgaa   1920
tccatgatac cactgaaacc agcacacatg atcgcagtaa aacctcatta tacttcctcc   1980
actatcacca ataccctta ttctctggaa catgaaacat tctgttgtgc tcatatcatg    2040
caaattatca ctagtaggag agcagagagt ggaaatgttc caggtataaa gacccacaag   2100
ataaagaagc tcagagtcgt tagaaacagg agcagatgta cagggtttgc ctgactcaca   2160
ctcaaggttg cataagcaag atttcaaaat taatcctatt ctggagacct caacccaatg   2220
tacaatgttc ctgactggaa aagaagaact atatttttct gatttttttt tttcaaatct   2280
ttaccattag ttgccctgta tctccgcctt cactttctgc aggaaacttt atttcctact   2340
tctgcatacc aagtttctac ctctagatct gtttggttca gttgctgaga agcctgacat   2400
accaggactg cctgagacaa gccacaagct ggtgagttgt aggcattttt tccattactt   2460
tctgattcat aggctcaacg cacctcaaag ctggaaatgc cgggtctggg tacaccctgg   2520
ggaactgcaa agcctgcaca cttgggggga atgatcaaga tgagaggcag gggtggggat   2580
ggcatgtgca ccaggagatg ttagagaaac cctgaggaag agcagcgtgc agcaggtgat   2640
gggggagagt gggcagcaag cgaggccagg acagccactc tgctcagtca ccagtccaca   2700
cacccagggg ctcactctgc ccctctgagc acccaaggac gttaaagagc tggaactgtt   2760
agtctaaata taggaccatc caagctctga accaaaatgt gtcccttgcc tcaactcagg   2820
agatccacag aggcagaagt aaggaattta ttttctgaaa gatagatttc tatcagttct   2880
gggtgacatg ttctgacact tgaaatgaca cctaggacag cacatttcag gcatcttgct   2940
cattgttcac tgtagtagaa gctacatgct agccagttgt aaaaatgaaa ttaagtaatg   3000
tgtgcacagc atttaacata gcatctgagc ttcaggagca ctcaattaat gaccacagtt   3060
gtgattcttt aggcagatgc atttttttcc aactttgatc agaggtctta tttagcttct   3120
ccagatttca agaatctggc tcagtgatat gaaatacaag acttgtgaaa agtgtcaatt   3180
gcaagagaaa tggaaggata aagtatacag gtgggtggaa aagaaattca cagtcactgc   3240
cagaaaaaaa attcttgaga atcaagtcct gatgatgtta gggcttatag ttcttattat   3300
aaagagtttt atgtactcat tcagtgaaca tttattggtg cctcctttag ccaggtacta   3360
tcataagagc tgaaaataga agcataatcc agtccttgat cttgaggaac atgctgtgtg   3420
tagcagataa cataataagt gcttatctag atgcatgcag tgttatgtga taagagtaat   3480
atgacagagg atacagatta ggcttcacag agaaggggga tttgagcagg aggtattgaa   3540
gggtgaatag aagctcacca atcattttgg gcagaggggc aaggacctgc aaaaccactg   3600
aagcatgaag gaaatggtga gtttagggaa aatgaagaga agatggctgt gactgaagca   3660
```

-continued

```
caggatttgg gattggagaa gggactggag gtgaggctga aaagaggcaa actcagaaaa   3720

gatgttgtgc tgggcagtct ggacattatc tttgaagccc accacatata agtcataggg   3780

ctactggagg ttttaagcta agagtgacta ttcaatttca acttaagaga agataggttg   3840

agagggaaca tggcttgaga tgagccatga gcaaaggaaa gactacaaca aagccaggag   3900

tgaggagtgt gtgaagcaag aaagtgacag ttgaaagcag tgcagagggg atgaatctga   3960

gaggcatcta tgaggtggaa ctcaaatgac atgataataa tacagggcat ttctctgtgt   4020

cagatgctgt cctaagtcct tactccattg atcttcacag caactcagca tagttaatat   4080

tttatgcata aagaaatcgg cacttgaagg agtaattggc cccagattac actgcctata   4140

aggattcaaa tccaggtttg tttggctcca aaaactggct cctaattttc agaaggagaa   4200

gcgacccagg gcaatgccca attttgcttc ttaggcaatg gaggaatcca caatcggaag   4260

gagttttcag cagtgcccca tttggggtgg gttgaatttg aggtccctgc atgataccca   4320

ctttgctcac ttcagtgcct aaaactgagt atggttcata gtaggtgttc aataagtgtt   4380

gatgcagtga atacatgcat ggggagatat gcatcaggca atgggaaatt caactctaag   4440

gcttagggga aagctggagc ttgaagacag agctttagaa aacagtagca tagaagggag   4500

taggaaccat gagtttagac aatacaattc aggaagaact ttgtagcaag gataaagagg   4560

caaaaaatta aagaggtgag agctaagtgt ggtgcctggg gaatcttaag gtgtgggcac   4620

ggggaggaga tgccagcaaa gaacatgaat aaaaagcggt agcacagccc ctcccatctg   4680

gaagccaaaa agaattgtaa atggaggaag ttagcagaag gatcaaatac ttgaagaggg   4740

tggaattgga ataaaaccag ggcatttgaa aaattgggtt gtcactgcaa tcttaacaag   4800

agaagttttg gcaggatgat ggaggcagaa agctgagaga atcatcagtt agaacgtttt   4860

tgacttcaga gaacagaaaa tgcagttcat aatggcttta aaacaggggc ttgtttttct   4920

cccagcaatt tgagaggcca aggcgggtgc atcaggaggt caagagaccg agaccatcct   4980

ggccaacatg gtgaatcccc atctctacta aaaatacaaa aattagcggg gcatggtggt   5040

gcacgcctat agtcccatct actcaggagg ctgaggcagg agaatcactt gaacccagga   5100

ggtggaggtt gcagtgagct gagatcatgg ccactgcact atagcctgga gacacagcga   5160

gactccgtct ccaaaaaaaa aaaaaaagaa ggcagaaggt gaatagttca agggtgggtt   5220

taggactcag tgataatagg attctgcctg gcttctcatg gttctctagg tcttccattc   5280

atggcaccat gccctcacta ggcatgctgc cagagcagga ggggcaggtg gagggttctc   5340

ttgtgtctgt cttatcaggg aagaagagct ttctcagaag cccccagcag actccctttt   5400

catattatgg tccagcaatg agtcacagac ctatgcacca cctgcaaagg agccagagaa   5460

aacaaacgcc cagcgctttt agcctgaaaa tgagaatctg gtttgctggg gaagataaag   5520

ggtgtcggaa aatggctgtt gggtaaatca ttgatgtctg ccactaggaa tgaaaggcaa   5580

atcaggaact ggcacacatg ctttcaggga gatggctgca agggagaggg caaagactgg   5640

gaagttgctt atgtggtgcc agactatttg gaagatcatg gattgcggtg tttgtgttgt   5700

gtggtcatca ttttgttctt tgtttacaga acagagaaag tggattgaac aaggacgcat   5760

ttccccagta catccacaac atgctgtcca catctcgttc tcggtttatc agaaatacca   5820

acgagagcgg tgaagaagtc accacctttt ttgattatga ttacggtgct ccctgtcata   5880

aatttgacgt gaagcaaatt ggggcccaac tcctgcctcc gctctactcg ctggtgttca   5940

tctttggttt tgtgggcaac atgctggtcg tcctcatctt aataaactgc aaaaagctga   6000

agtgcttgac tgacatttac ctgctcaacc tggccatctc tgatctgctt tttcttatta   6060
```

-continued

```
ctctcccatt gtgggctcac tctgctgcaa atgagtgggt ctttgggaat gcaatgtgca   6120
aattattcac agggctgtat cacatcggtt attttggcgg aatcttcttc atcatcctcc   6180
tgacaatcga tagatacctg gctattgtcc atgctgtgtt tgctttaaaa gccaggacgg   6240
tcacctttgg ggtggtgaca agtgtgatca cctggttggt ggctgtgttt gcttctgtcc   6300
caggaatcat ctttactaaa tgccagaaag aagattctgt ttatgtctgt ggcccttatt   6360
ttccacgagg atggaataat ttccacacaa taatgaggaa cattttgggg ctggtcctgc   6420
cgctgctcat catggtcatc tgctactcgg gaatcctgaa aaccctgctt cggtgtcgaa   6480
acgagaagaa gaggcatagg gcagtgagag tcatcttcac catcatgatt gtttactttc   6540
tcttctggac tccctataat attgtcattc tcctgaacac cttccaggaa ttcttcggcc   6600
tgagtaactg tgaaagcacc agtcaactgg accaagccac gcaggtgaca gagactcttg   6660
ggatgactca ctgctgcatc aatcccatca tctatgcctt cgttggggag aagttcagaa   6720
ggtatctctc ggtgttcttc cgaaagcaca tcaccaagcg cttctgcaaa caatgtccag   6780
ttttctacag ggagacagtg gatggagtga cttcaacaaa cacgccttcc actggggagc   6840
aggaagtctc ggctggttta taaaacgagg agcagtttga ttgttgttta taaagggaga   6900
taacaatctg tatataacaa caaacttcaa gggtttgttg aacaatagaa acctgtaaag   6960
caggtgccca ggaacctcag ggctgtgtgt actaatacag actatgtcac ccaatgcata   7020
tccaacatgt gctcagggaa taatccagaa aaactgtggg tagagacttt gactctccag   7080
aaagctcatc tcagctcctg aaaaatgcct cattaccttg tgctaatcct ctttttctag   7140
tcttcataat ttcttcactc aatctctgat tctgtcaatg tcttgaaatc aagggccagc   7200
tggaggtgaa gaagagaatg tgacaggcac agatgaatgg gagtgaggga tagtggggtc   7260
agggctgaga ggagaaggag ggagacatga gcatggctga gcctggacaa agacaaaggt   7320
gagcaaaggg ctcacgcatt cagccaggag atgatactgg tccttagccc catctgccac   7380
gtgtatttaa ccttgaaggg ttcaccaggt cagggagagt ttgggaactg caataacctg   7440
ggagttttgg tggagtccga tgattctctt ttgcataagt gcatgacata tttttgcttt   7500
attacagttt atctatggca cccatgcacc ttacatttga aatctatgaa atatcatgct   7560
ccattgttca gatgcttctt aggccacatc cccctgtcta aaaattcaga aaatttttgt   7620
ttataaaaga tgcattatct atgatatgct aatatatgta tatgcaatat atataggctc   7680
ttgcttgatc tctccaggag gtagtgatta tgagaagggg gtggagaatg atgagttcct   7740
tcaccaggag caaaggacgg ggatcgtgtg gaaccactgc agaactattt ccgaaatcaa   7800
ctaagtggag agagccagga aggctgcatc agaacccagt aaagcttctt gtctggatct   7860
gagctggttt gttttgtgct tgcttttccc tgccttgcca ctcccctcac tcttctcttt   7920
tccccacagc ctttttcaca tagctcttgg ctgtaggatt gccccactcc aaaaaccagt   7980
gtgtggaggt ccaggagtga gaccaggaaa gaatgtgaaa gtgactacac aaggactcct   8040
cgatggtcgt ggaaaaggaa agtcaattgg cagagcccct gaagccagtc ttcaggacaa   8100
agaaggagcc tagagacaga aatgacagat ctctgctttg gaaatcacac gtctggcttc   8160
acagatgtgt gattcacagt gtgaatcttg gtgtctacgt taccaggcag gaaggctgag   8220
aggagagaga ctccagctgg gttggaaaac agtattttcc aaactacctt ccagttcctc   8280
atttttgaat acaggcatag agttcagact ttttttaaat agtaaaaata aaattaaagc   8340
tgaaaactgc aacttgtaaa tgtggtaaag agttagtttg agttactatc atgtcaaacg   8400
```

-continued

```
tgaaaatgct gtattagtca cagagataat tctagctttg agcttaagaa ttttgagcag   8460

gtggtatgtt tgggagactg ctgagtcaac ccaatagttg ttgattggca ggagttggaa   8520

gtgtgtgatc tgtgggcaca ttagcctatg tgcatgcagc atctaagtaa tgatgtcgtt   8580

tgaatcacag tatacgctcc atcgctgtca tctcagctgg atctccattc tctcaggctt   8640

gctgccaaaa gccttttgtg ttttgttttg tatcattatg aagtcatgcg tttaatcaca   8700

ttcgagtgtt tcagtgcttc gcagatgtcc ttgatgctca tattgttccc tattttgcca   8760

gtgggaactc ctaaatcaag ttggcttcta atcaaagctt ttaaacccta ttggtaaaga   8820

atggaaggtg gagaagctcc ctgaagtaag caaagacttt cctcttagtc gagccaagtt   8880

aagaatgttc ttatgttgcc cagtgtgttt ctgatctgat gcaagcaaga aacactgggc   8940

ttctagaacc aggcaacttg ggaactagac tcccaagctg gactatggct ctactttcag   9000

gccacatggc taaagaaggt ttcagaaaga agtggggaca gagcagaact ttcaccttca   9060

tatatttgta tgatcctaat gaatgcataa aatgttaagt tgatggtgat gaaatgtaaa   9120

tactgttttt aacaactatg atttggaaaa taaatcaatg ctataactat gttgataaaa   9180

gatttaaaaa caactggctg tttttttaca ctgtggtgtg gaagattgtg ttgtgttcac   9240

aacttttcac ttcttcccct gtgtgattac acacacctgc ccttgtggtg tgacttgcag   9300

tgcgccctac aggccacaca accccatgcc ctccaccact ggctctgctg ctggaatgtg   9360

agcagaagtg acatctgcct catccaagca gagcctcttg ctcagccaca ggaaggccca   9420

ttccagatca cacccgtcag cccgtgcgcc ctggtgaatg agaagacaca gggagctgca   9480

gccacatata acatgagcaa gaagtctgtg tttgctgtga taagccactg agttttaggg   9540

gttgtttgtt aagaagcaca aaaaccgatt aagacatgtg gtatatagtg acttcatata   9600

tagaatctgg aaaactatcc atttattttc aatcatggaa ttcaatatga caagcatccc   9660

ggagggtcta cctatgccag actgggttgg aaacagaaag acagatgtta atgccagtgt   9720

cctttacacc tccaagtcca gggccagctg tggagtggga ggggtagaga aggtcctgtg   9780

cacagtcaca gtgcgctgtg cagagcagga acagaggcat ctgtgaaaag tgctgagagc   9840

ctggaggaca gagtgactaa tgcaatgaca gtcttgcatc ataggaataa cagccacagc   9900

aggattttat tgctgccaaa gaaactgcca tttaaaaatt gccagccatc cgggaggctg   9960

aggcaggaga atggcatgaa tccaggaggc ggagcttgca gtgagccgag atcgggccac  10020

tgcactccag cctgggcaac agagccagac tccatctcaa aaaaaaaaaa aaa         10073
```

<210> SEQ ID NO 8
<211> LENGTH: 2082
<212> TYPE: DNA
<213> ORGANISM: Homo sapiens

<400> SEQUENCE: 8

```
gcacacctgt aatcccagcc cttcaggagg ctgaggcagg cagattgcct gagcccagga     60

gttcgagacc agcccgggca acatgacaaa accccatctc tacaaaaaat agtcaggcat    120

ggtggcatgc acctgtagtc tcagctactt gggaggctga gatgagagga ttgcttgagg    180

ttgagactgc actgaagcat gatcatgcca ccgcactcca gcctaggcaa cagagcaaga    240

tcttgtcgca aaagaaagca aaaatacaac ataacacaac aacaacaaca acaacaacaa    300

cagcaaaaaa gccaacttct tgaaatctgg aaaggacacc tccactgccc tcagcatttg    360

attgttgttg gctctagcag tggatgcatc cttcaacctc tggcactctg caggggctca    420

gactgttctg ttctgtttgt tacctgtgga gtgcctgcca gaccctgctc tagctgcttt    480
```

-continued

```
aggtccattt accctcatag acccccagtc ttgttattca tatttcatat ttgggaaatg    540
gaaacttaga aacttgccaa gtccacagca tgagatcctg cctccggtgt ctgctggatt    600
ccagaaagtg ccaggggcca acttagatga caccatgttc tctgcacaat cttaggaatg    660
ctcctagtct gatgtcccca ttgcaaaatt tacattatct tttaacaaaa cgtctttcca    720
aggaggggca tttaaaataa ctgaggttct tcttgctaag gacgttcctg acacaagaga    780
taatttagca tttccttttc attaaaaagt ttgaaatcct gtaatttgtg ataatgtgga    840
tgaacctaga ggatgttaag tgaaataagc cacacacaga tagacaaata ccacgtgatc    900
tcactcttat gtggaatttt tttttaaata agttgcttag ccgggcatga tggcacacac    960
ctgtaatcct agctactcag gaggctgagg tgggaggatg gcttgaactc agaaggtgga   1020
ggtagcagtg agctgagact gtgccagtgc actccggtct gggtgacaga atgaaaccca   1080
atttaaaaaa aaaaaaaaag ttgctatctt agaaaaagac agtagagcag tggttaccag   1140
agactgggga ggaaagagag gaggtgagaa tgggcagcag ttgatcaacg ggtacaaagt   1200
taccatgaga taggagaaac aagtgctggt gctctgctcc aagtagggtg acggtagtta   1260
ataatgaatt ctgtatatat aaatagctag aagagagggt tttcaatatc attattattt   1320
caaaagaaat gataaatgtt tcagaggatg gatatgtaat taccctgatt tgatcattgc   1380
acaatgtata catgtagcaa aacatcacat tgtgtcccat aaatatatac aattattatg   1440
tgaattaaat aaaaaaaaat tttaaagtct tatctaaatg aaatttctaa ccagattctg   1500
aatccatgat accactgaaa ccagcacaca tgatcgcagt aaaacctcat tatacttcct   1560
ccactatcac caataccctt tattctctgg aacatgaaac attctgttgt gctcatatca   1620
tgcaaattat cactagtagg agagcagaga gtggaaatgt tccaggtata aagacccaca   1680
agataaagaa gctcagagtc gttagaaaca ggagcagatg tacagggttt gcctgactca   1740
cactcaaggt tgcataagca agatttcaaa attaatccta ttctggagac ctcaacccaa   1800
tgtacaatgt tcctgactgg aaaagaagaa ctatattttt ctgatttttt ttttcaaatc   1860
tttaccatta gttgccctgt atctccgcct tcactttctg caggaaactt tatttcctac   1920
ttctgcatgc caagtttcta cctctagatc tgtttggttc agttgctgag aagcctgaca   1980
taccaggact gcctgagaca agccacaagc tggtgagttg taggcatttt ttccattact   2040
ttctgattca taggctcaac gcacctcaaa gctggaaatg cc                      2082
```

<210> SEQ ID NO 9
<211> LENGTH: 5444
<212> TYPE: DNA
<213> ORGANISM: Homo sapiens

<400> SEQUENCE: 9

```
ctacctccaa ccatgggcct tttgggaata ctttgttttt taatcttcct ggggaaaacc     60
tggggacagg agcaaacata tgtcatttca gcaccaaaaa tattccgtgt tggagcatct    120
gaaaatattg tgattcaagt ttatggatac actgaagcat ttgatgcaac aatctctatt    180
aaaagttatc ctgataaaaa atttagttac tcctcaggcc atgttcattt atcctcagag    240
aataaattcc aaaactctgc aatcttaaca atacaaccaa aacaattgcc tggaggacaa    300
aacccagttt cttatgtgta tttggaagtt gtatcaaagc atttttcaaa atcaaaaaga    360
atgccaataa cctatgacaa tggatttctc ttcattcata cagacaaacc tgtttatact    420
ccagaccagt cagtaaaagt tagagtttat tcgttgaatg acgacttgaa gccagccaaa    480
```

-continued

```
agagaaactg tcttaacctt catagatcct gaaggatcag aagttgacat ggtagaagaa    540
attgatcata ttggaattat ctcttttcct gacttcaaga ttccgtctaa tcctagatat    600
ggtatgtgga cgatcaaggc taaatataaa gaggactttt caacaactgg aaccgcatat    660
tttgaagtta aagaatatgt cttgccacat tttctgtct caatcgagcc agaatataat    720
ttcattggtt acaagaactt taagaatttt gaaattacta taaaagcaag atatttttat    780
aataaagtag tcactgaggc tgacgtttat atcacatttg gaataagaga agacttaaaa    840
gatgatcaaa aagaaatgat gcaaacagca atgcaaaaca caatgttgat aaatggaatt    900
gctcaagtca catttgattc tgaaacagca gtcaaagaac tgtcatacta cagtttagaa    960
gatttaaaca acaagtacct ttatattgct gtaacagtca tagagtctac aggtggattt   1020
tctgaagagg cagaaatacc tggcatcaaa tatgtcctct ctccctacaa actgaatttg   1080
gttgctactc ctcttttcct gaagcctggg attccatatc ccatcaaggt gcaggttaaa   1140
gattcgcttg accagttggt aggaggagtc ccagtaatac tgaatgcaca aacaattgat   1200
gtaaaccaag agacatctga cttggatcca agcaaaagtg taacacgtgt tgatgatgga   1260
gtagcttcct ttgtgcttaa tctcccatct ggagtgacgg tgctggagtt taatgtcaaa   1320
actgatgctc cagatcttcc agaagaaaat caggccaggg aaggttaccg agcaatagca   1380
tactcatctc tcagccaaag ttacctttat attgattgga ctgataacca taaggctttg   1440
ctagtgggag aacatctgaa tattattgtt acccccaaaa gcccatatat tgacaaaata   1500
actcactata attacttgat tttatccaag ggcaaaatta tccattttgg cacgagggag   1560
aaattttcag atgcatctta tcaaagtata aacattccag taacacagaa catggttcct   1620
tcatcccgac ttctggtcta ttatatcgtc acaggagaac agacagcaga attagtgtct   1680
gattcagtct ggttaaatat tgaagaaaaa tgtggcaacc agctccaggt tcatctgtct   1740
cctgatgcag atgcatattc tccaggccaa actgtgtctc ttaatatggc aactggaatg   1800
gattcctggg tggcattagc agcagtggac agtgctgtgt atggagtcca aagaggagcc   1860
aaaaagccct tggaaagagt atttcaattc ttagagaaga gtgatctggg ctgtggggca   1920
ggtggtggcc tcaacaatgc caatgtgttc cacctagctg gacttacctt cctcactaat   1980
gcaaatgcag atgactccca agaaaatgat gaaccttgta aagaaattct caggccaaga   2040
agaacgctgc aaaagaagat agaagaaata gctgctaaat ataaacattc agtagtgaag   2100
aaatgttgtt acgatggagc ctgcgttaat aatgatgaaa cctgtgagca gcgagctgca   2160
cggattagtt tagggccaag atgcatcaaa gctttcactg aatgttgtgt cgtcgcaagc   2220
cagctccgtg ctaatatctc tcataaagac atgcaattgg gaaggctaca catgaagacc   2280
ctgttaccag taagcaagcc agaaattcgg agttattttc cagaaagctg gttgtgggaa   2340
gttcatcttg ttcccagaag aaaacagttg cagtttgccc tacctgattc tctaaccacc   2400
tgggaaattc aaggcattgg catttcaaac actggtatat gtgttgctga tactgtcaag   2460
gcaaaggtgt tcaaagatgt cttcctggaa atgaatatac catattctgt tgtacgagga   2520
gaacagatcc aattgaaagg aactgtttac aactatagga cttctgggat gcagttctgt   2580
gttaaaatgt ctgctgtgga gggaatctgc acttcggaaa gcccagtcat tgatcatcag   2640
ggcacaaagt cctccaaatg tgtgcgccag aaagtagagg gctcctccag tcacttggtg   2700
acattcactg tgcttcctct ggaaattggc cttcacaaca tcaatttttc actggagact   2760
tggtttggaa aagaaatctt agtaaaaaca ttacgagtgg tgccagaagg tgtcaaaagg   2820
gaaagctatt ctggtgttac tttggatcct aggggtattt atggtaccat tagcagacga   2880
```

-continued

```
aaggagttcc catacaggat acccttagat ttggtcccca aaacagaaat caaaaggatt   2940
ttgagtgtaa aaggactgct tgtaggtgag atcttgtctg cagttctaag tcaggaaggc   3000
atcaatatcc taacccacct ccccaaaggg agtgcagagg cggagctgat gagcgttgtc   3060
ccagtattct atgtttttca ctacctggaa acaggaaatc attggaacat tttcattct   3120
gacccattaa ttgaaaagca gaaactgaag aaaaaattaa aagaagggat gttgagcatt   3180
atgtcctaca gaaatgctga ctactcttac agtgtgtgga agggtggaag tgctagcact   3240
tggttaacag cttttgcttt aagagtactt ggacaagtaa ataaatacgt agagcagaac   3300
caaaattcaa tttgtaattc tttattgtgg ctagttgaga attatcaatt agataatgga   3360
tctttcaagg aaaattcaca gtatcaacca ataaaattac agggtacctt gcctgttgaa   3420
gcccgagaga acagcttata tcttacagcc tttactgtga ttggaattag aaaggctttc   3480
gatatatgcc ccctggtgaa aatcgacaca gctctaatta aagctgacaa ctttctgctt   3540
gaaaatacac tgccagccca gagcaccttt acattggcca tttctgcgta tgctctttcc   3600
ctgggagata aaactcaccc acagtttcgt tcaattgttt cagctttgaa gagagaagct   3660
ttggttaaag gtaatccacc catttatcgt ttttggaaag acaatcttca gcataaagac   3720
agctctgtac ctaacactgg tacggcacgt atggtagaaa caactgccta tgctttactc   3780
accagtctga acttgaaaga tataaattat gttaacccag tcatcaaatg gctatcagaa   3840
gagcagaggt atggaggtgg cttttattca acccaggaca ccatcaatgc cattgagggc   3900
ctgacggaat attcactcct ggttaaacaa ctccgcttga gtatggacat cgatgtttct   3960
tacaagcata aaggtgcctt acataattat aaaatgacag acaagaattt ccttgggagg   4020
ccagtagagg tgcttctcaa tgatgacctc attgtcagta caggatttgg cagtggcttg   4080
gctacagtac atgtaacaac tgtagttcac aaaaccagta cctctgagga agtttgcagc   4140
ttttatttga aaatcgatac tcaggatatt gaagcatccc actacagagg ctacggaaac   4200
tctgattaca aacgcatagt agcatgtgcc agctacaagc ccagcaggga agaatcatca   4260
tctggatcct ctcatgcggt gatggacatc tccttgccta ctggaatcag tgcaaatgaa   4320
gaagacttaa aagcccttgt ggaaggggtg gatcaactat tcactgatta ccaaatcaaa   4380
gatggacatg ttattctgca actgaattcg attccctcca gtgatttcct ttgtgtacga   4440
ttccggatat ttgaactctt tgaagttggg tttctcagtc ctgccacttt cacagtttac   4500
gaataccaca gaccagataa acagtgtacc atgttttata gcacttccaa tatcaaaatt   4560
cagaaagtct gtgaaggagc cgcgtgcaag tgtgtagaag ctgattgtgg gcaaatgcag   4620
gaagaattgg atctgacaat ctctgcagag acaagaaaac aaacagcatg taaaccagag   4680
attgcatatg cttataaagt tagcatcaca tccatcactg tagaaaatgt ttttgtcaag   4740
tacaaggcaa cccttctgga tatctacaaa actggggaag ctgttgctga gaaagactct   4800
gagattacct tcattaaaaa ggtaacctgt actaacgctg agctggtaaa aggaagacag   4860
tacttaatta tgggtaaaga agccctccag ataaaataca atttcagttt caggtacatc   4920
taccctttag attccttgac ctggattgaa tactggccta gagacacaac atgttcatcg   4980
tgtcaagcat ttttagctaa tttagatgaa tttgccgaag atatcttttt aaatggatgc   5040
taaaattcct gaagttcagc tgcatacagt ttgcacttat ggactcctgt tgttgaagtt   5100
cgttttttttg ttttcttctt tttttaaaca ttcatagctg gtcttatttg taaagctcac   5160
tttacttaga attagtggca cttgctttta ttagagaatg atttcaaatg ctgtaacttt   5220
```

-continued

```
ctgaaataac atggccttgg agggcatgaa gacagatact cctccaaggt tattggacac   5280

cggaaacaat aaattggaac acctcctcaa acctaccact caggaatgtt tgctggggcc   5340

gaaagaacag tccattgaaa gggagtatta caaaaacatg gcctttgctt gaaagaaaat   5400

accaaggaac aggaaactga tcattaaagc ctgagtttgc tttc                    5444


<210> SEQ ID NO 10
<211> LENGTH: 222
<212> TYPE: DNA
<213> ORGANISM: Homo sapiens

<400> SEQUENCE: 10

ctacctccaa ccatgggcct tttgggaata ctttgttttt taatcttcct ggggaaaacc     60

tggggacagg agcaaacata tgtcatttca gcaccaaaaa tattccgtgt tggagcatct    120

gaaaatattg tgattcaagt ttatggatac actgaagcat ttgatgcaac aatctctatt    180

aaaagttatc ctgataaaaa atttagttac tcctcaggcc at                       222
```

METHODS AND ANIMAL MODEL FOR ANALYZING AGE-RELATED MACULAR DEGENERATION

This application claims priority to U.S. provisional application Ser. No. 60/422,096, filed Oct. 30, 2002, incorporated herein in its entirety.

FIELD OF THE INVENTION

The invention relates to methods of determining the pathology of age-related macular degeneration and methods of testing treatment protocols and candidate drugs for age-related macular degeneration. More particularly, the invention relates to use of Ccl2-deficient, Ccr2-deficient, or both Ccl2 and Ccr2-deficient mice to analyze the pathology and treatment of age-related macular degeneration and test candidate drugs for treatment of age-related macular edema.

BACKGROUND OF THE INVENTION

Age-related macular degeneration (AMD) is the principal cause of legal blindness in the United States and Western Europe. It affects over 11 million people in this country alone, and with the aging population will exact an even greater toll. The earliest visible abnormality in AMD is the accumulation of drusen (Gass, J. D. (1972) *Trans Am Ophthalmol Soc* 70, 409-36.), lipoproteinaceous deposits between the retinal pigment epithelium (RPE) and Bruch's membrane, the extracellular matrix between the RPE and the underlying choroid. Drusen are a significant risk factor for progression to choroidal neovascularization (CNV), the principal cause of vision loss in AMD (Macular Photocoagulation Study Group (1997) *Arch Ophthalmol* 115, 741-7). There is no animal model of drusen resembling that of patients with AMD. Drusen-like deposits in elderly primates (Hope, et al., (1992) *Br J Ophthalmol* 76, 11-6.) are dissimilar to human drusen both in ultrastructural morphology and biochemical composition (Hirata, A. & Feeney-Burns, L. (1992) *Invest Ophthalmol Vis Sci* 33, 2079-90; Mullins, R. F. & Hageman, G. S. (1997) in *Degenerative Retinal Diseases*, ed. LaVail, M. (Plenum Press, New York), pp. 1-10.). Attempts to create a murine model of drusen by high fat diet, disrupting the apolipoprotein E gene, inducing protoporphyria (Gottsch et al., (1993) *Arch Ophthalmol* 111, 126-9.), accelerating senescence (Majji, et al., (2000) *Invest Ophthalmol Vis Sci* 41, 3936-42), or combinations of the above (Dithmar et al., (2001) *Arch Ophthalmol* 119, 1643-9) have not succeeded in creating drusen.

The biogenesis of drusen involves RPE dysfunction, impaired digestion of photoreceptor outer segments, and subsequent debris accumulation (Hageman, et al.,. (2001) *Prog Retin Eye Res* 20, 705-32). The presence of complement C5, immunoglobulins, apolipoprotein E, vitronectin, and clusterin in human drusen (Loffler, et al., (1986) *Graefes Arch Clin Exp Ophthalmol* 224, 493-501; Hageman, G. S., et al., (1999) *FASEB J* 13, 477-84; Hageman, G. S. & Mullins, R. F. (1999) *Mol Vis* 5, 28; Johnson, et al., (2000) *Exp Eye Res* 70, 441-9; Mullins et al., (2000) *FASEB J* 14, 835-46; and Anderson, et al., (2001) *Am J Ophthalmol* 131, 767-81) suggests that focal concentration of these materials may produce a powerful chemotactic stimulus for leukocytes, possibly acting via a complement cascade (Killingsworth, et al., (2001) *Exp Eye Res* 73, 887-96). Consistent with this, macrophages appear to preferentially engulf the wide-banded collagen of basal deposits in patients with AMD, suggesting a role in drusen clearance (Loffler, K. U. & Lee, W. R. (1986) *Graefes Arch Clin Exp Ophthalmol* 224, 493-501; Killingsworth, et al., (1990) *Eye* 4, 613-21; Penfold, P. L., et al., (1985) *Graefes Arch Clin Exp Ophthalmol* 223, 69-76; and van der Schaft, et al., (1993) *Br J Ophthalmol* 77, 657-61). Laser photocoagulation induced regression of drusen in humans (Ho, et al., (1999) *Ophthalmology* 106, 1367-73; and Olk, et al., (1999) *Ophthalmology* 106, 2082-90) is believed to result from recruitment of macrophages that resorb these deposits (Duvall, J. & Tso, M. O. (1985) *Arch Ophthalmol* 103, 694-703).

The lack of a faithful animal model of AMD has hampered both the study and treatment of age-related macular degeneration. Thus, there is a need for a faithful animal model of drusen development and accumulation to provide mechanistic insights into the development of AMD and assist in evaluating candidate drugs for the treatment of age-related macular degeneration.

SUMMARY OF THE INVENTION

In one aspect of the invention there is provided a method for testing a candidate drug for treatment or prevention of age-related macular degeneration comprising administering the candidate drug to a Ccl2-deficient, Ccr2-deficient- or a Ccl2-deficient and -Ccr2-deficient mouse and analyzing the eye of the mouse for development or regression of drusen and/or lipofuscin accumulation therein, for affect of the candidate drug on Bruch's membrane and/or choroidal neovascularization of the eyes of the mouse.

There is also provided a method of screening a test compound for potential utility for treatment of age-related macular degeneration, comprising: (a) providing a mouse comprising a disrupted Ccl2 and/or CCR2 gene, wherein the mouse is homozygous for the disrupted gene or genes, and wherein the mouse exhibits drusen and/or lipofuscin deposits, retinal degeneration, and/or choroidal neovascularization in at least one eye at about nine to twenty-four months of age compared to a wild-type mouse that does not have the disrupted gene; (b) administering the test compound to the mouse; (c) determining the effect of the test compound on drusen, lipofuscin deposition, retinal degeneration, or choroidal neovascularization in at least one eye of the mouse; and (d) correlating the effect of the test compound on drusen, lipofuscin accumulation, retinal degeneration, and/or choroidal neovascularization with a potential utility to treat age-related macular degeneration.

In another aspect of the invention there is provided a method of monitoring the effects of expression of a Ccl2 gene in at least one eye of a Ccl2−/− mouse comprising (1) introducing a plurality of stem cells obtained from a wild type mouse into the Ccl2−/− mouse to obtain a transplanted mouse, wherein said stem cells express wild type Ccl2; and (2) observing at least one eye of the transplanted mouse for the effect of the wild type Ccr2 gene expression on drusen or lipofuscin deposition, retinal degeneration, or choroidal neovascularization in at least one eye of the transplanted mouse. There is also provided a method of a method of monitoring the expression of a Ccr2 gene in at least one eye of a Ccr2−/− mouse comprising (1) introducing a plurality of stem cells obtained from a wild type mouse into the Ccr2−/− mouse to obtain a transplanted mouse, wherein said stem cells express wild type Ccr2; and (2) observing at least one eye of the transplanted mouse for the effect of the wild type Ccr2 gene expression on drusen or lipofuscin deposition, retinal degeneration, or choroidal neovascularization in at least one eye of the transplanted mouse. There is also provided a method of monitoring the effects of expression of a Ccl2 gene, Ccr2 gene or both in at least one eye of a Ccl2 deficient, Ccr2 deficient mouse comprising (1) introducing a plurality of stem cells obtained from a wild type mouse into the Ccl2 deficient, Ccr2 deficient mouse to obtain a transplanted mouse, wherein said stem cells express wild type Ccl2 and Ccr2; and (2) observing at least one eye of the transplanted mouse for the effect of the wild type Ccl2 and/or Ccr2 gene expression on drusen or lipofuscin deposition, retinal degeneration, or choroidal neovascularization in at least one eye of the transplanted mouse.

In a further aspect of the invention there is provided a Ccl2-deficient/CCR2-deficient dual knockout mouse.

The present invention also provides a method of identifying mutations in the Ccl2 gene, Ccr2 gene or both comprising (1) obtaining an AMD DNA library or genomic DNA from a blood sample of an AMD patient; (2) screening the AMD DNA library or genomic DNA for sequences that hybridize under high stringency conditions to a wild type Ccl2 gene, Ccr2 gene, or both; and (3) sequencing the sequences that hybridize to determine the identity of any mutations contained therein.

In a further aspect of the invention there are provided expression vectors comprising SEQ ID NO. 9 and/or SEQ ID NO. 10.

In yet a further aspect of the invention there is provided a method of screening for mutations that potentially cause or affect the development of AMD in a human comprising (1) obtaining an AMD DNA library or genomic DNA from a blood sample of an AMD patient; (2) screening the AMD DNA library or genomic DNA for sequences that hybridize under high stringency conditions to a wild type C5 receptor gene or C5a receptor gene; (3) sequencing the sequences that hybridize to determine the identity of any mutations contained therein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7A-D is the nucleotide sequence of the human Ccl2 gene (variants, promoter, and enhancer regions) (SEQ ID NO. 1-4).

FIG. 8A-D is the nucleotide sequence of the human Ccr2 gene (variants, isoforms, promoter region) (SEQ ID NO. 5-8)

FIG. 9 is the nucleotide sequence of the human C5 receptor gene (SEQ ID NO. 9).

FIG. 10 is the nucleotide sequence of the human C5a receptor gene (SEQ ID NO. 10).

DETAILED DESCRIPTION OF THE INVENTION

The inventors have discovered two strains of genetically modified mice that develop many features of AMD as they age. Elderly mice (9-24 months) deficient in the gene for monocyte chemoattractant protein-1 (Ccl2, formerly referred to as MCP-1) (Lu, B et al., (1998) *J Exp Med* 187, 601-8) or its cognate receptor CC chemokine receptor-2 (Ccr2) (Kuziel, et al., (1997) *Proc Natl Acad Sci USA* 94, 12053-8.) develop drusen, lipofuscin, and thickened Bruch's membrane (the extracellular matrix between the RPE and choroid), the earliest manifestations of AMD in humans, as well as intrachoroidal neovascularization. They also develop degeneration of the outer neural retina, which is seen in many patients with AMD (Green, W. R. & Enger, C. (1993) *Ophthalmology* 100, 1519-35). These pathologies are absent in age-matched wild-type mice and several other knockout strains of mice.

The present inventors have discovered that the development of drusen is more pronounced in the Ccl2 mice in comparison to the Ccr2 mice. Also, the accumulation of drusen occurs earlier in the Ccl2 mice. However, Ccr2−/− mice also display evidence of drusen on fundus examination (FIG. 1). Just as Ccl2 deficient mice, Ccr2-deficient mice also exhibit phenotypic variation: some have the discrete hard drusen, while others have confluent drusen.

Figure 2A:
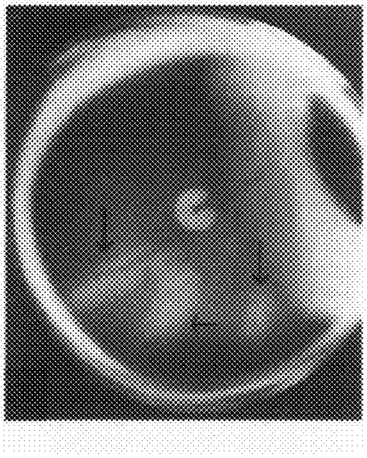
FIG. 2. $Ccl2^{-/-}$ and $Ccr2^{-/-}$ mice develop retinal degeneration. a, Fundus of an 18-month-old $Ccr2^{-/-}$ mouse shows geographic atrophy (arrows). b,c, Electron micrographs show healthy photoreceptor cell bodies in 14-month-old wild-type mouse (b) and attenuated photoreceptors with pyknotic nuclei (arrows) in 16-month-old $Ccl2^{-/-}$ mouse (c). d,e, Orderly arrays of photoreceptor outer segments in 14-month-old wild-type mouse (d) and marked degeneration and segments (asterisk) with pigment-laden RPE cells (arrows) amidst disorganized tissue in 16-month-old $Ccl2^{-/-}$ mouse (e). f, RPE of 16-month-old $Ccl2^{-/-}$ mouse shows marked vacuolization (black arrows), degenerated nucleus (black asterisk), and few pigment granules (white arrow). Choroid is filled with abundant melanocytes (white asterisks) but no choriocapillaris vessels. g,h, Retina in $Ccl2^{-/-}$ mouse outside these atrophic areas contains normal photoreceptor cell bodies (g) and outer segments (h). Scale bar 10 μm (b,c,f,g) and 5 μm (d,e,h).
Figure 2B:
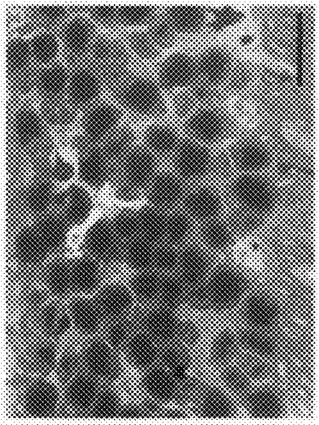
Figure 2C:
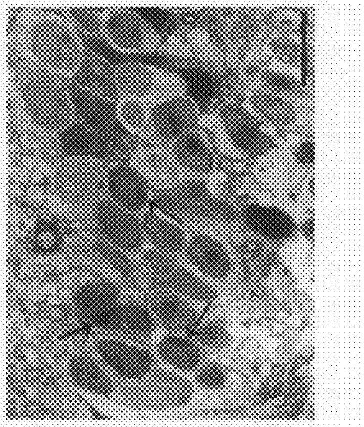
Figure 2D:
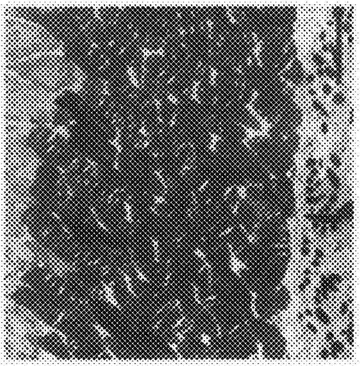
Figure 2E:
Figure 2F:
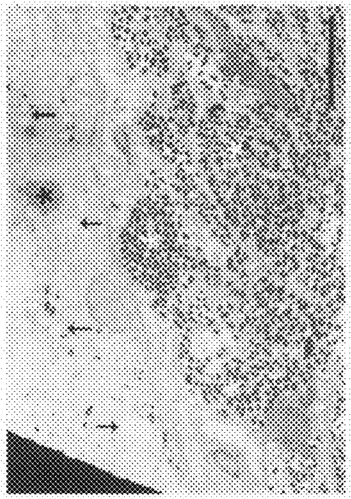
Figure 2G:
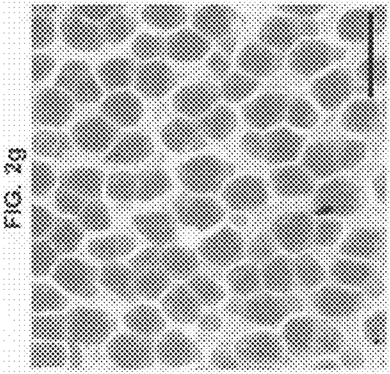
Figure 2H:
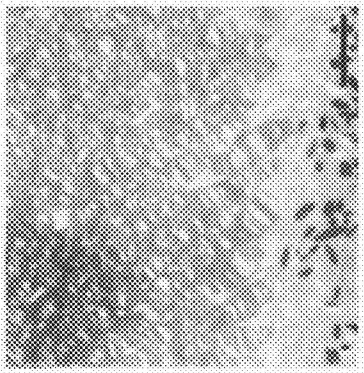
Figures 3A, 3B, 3C, 3D, 3E, 3F, 3G, 3H, 3I, 3J, 3K, 3L, 3M, 3N:
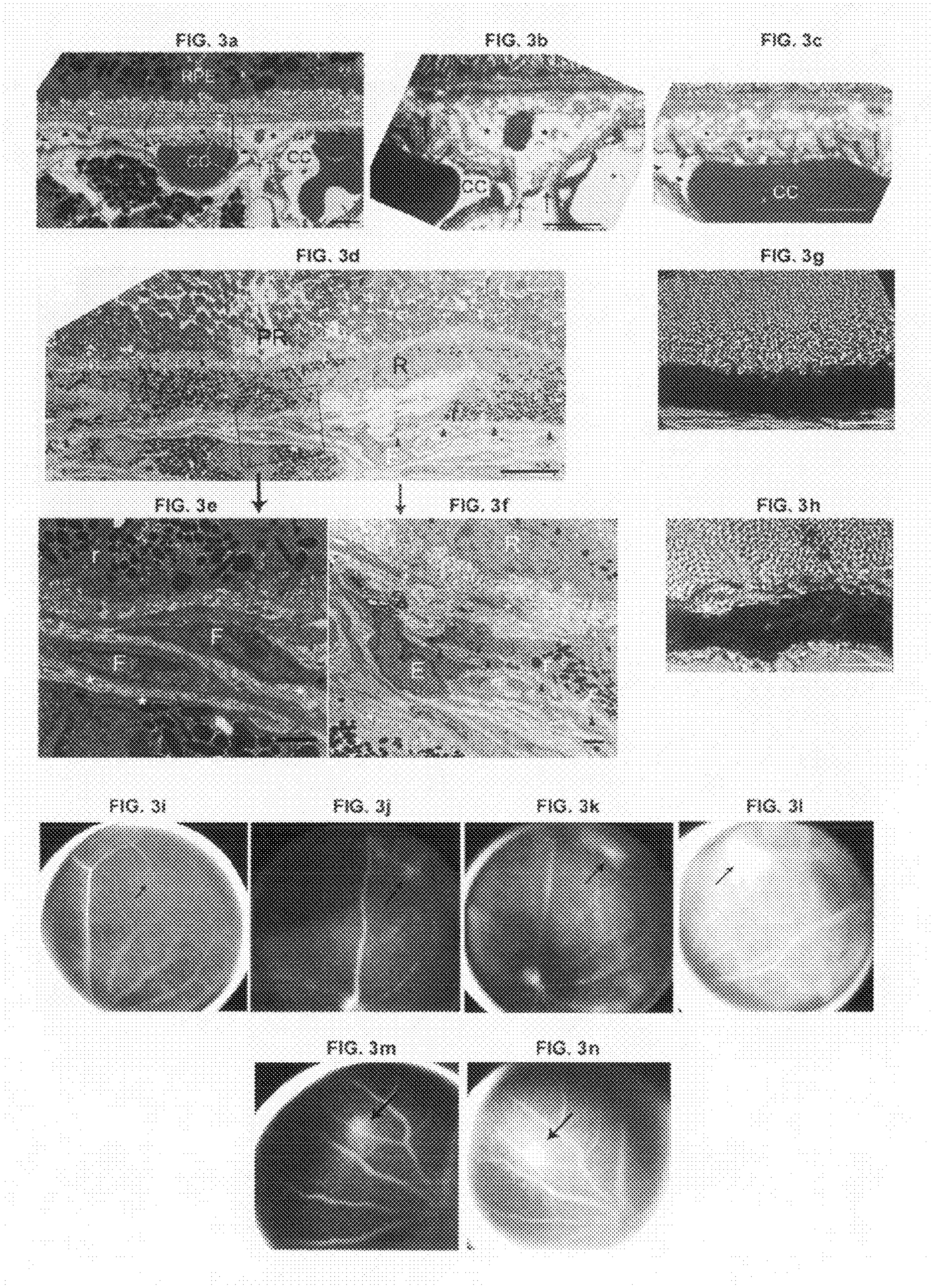
FIG. 3. $Ccl2^{-/-}$ and $Ccr2^{-/-}$ mice develop neovascular AMD and overexpress VEGF in RPE. a-c, Electron micrograph in 20-month-old $Ccl2^{-/-}$ mouse shows dilated choriocapillaries (CC) inserting processes (blue arrows) into Bruch's membrane (BM), with fragmented collagen and elastin layers (asterisks) of BM in a 20-month-old $Ccl2^{-/-}$ mouse. Inner BM (white arrowheads) is intact whereas outer BM (black arrowheads) is breached by choriocapillary processes (blue arrows) and fractures (red arrows). Higher magnification of insets (white area-b and black area-c) shows breaks (red arrows) in outer BM and endothelial processes (blue arrows) inserted into BM, disrupting outer collagenous (black asterisk) and elastin and inner collagenous layers (white asterisks), and large fenestrae (arrowheads) (c). d-f, CNV in 24-month-old $Ccr2^{-/-}$ mouse where an endothelial cell (E) and fibrocytes (asterisks) invade sub-RPE space through a defect in BM (arrowheads), disrupting overlying photoreceptors (PR). Higher magnification of insets shows (e) fibrocytes (F) invading BM and disrupting overlying RPE (r) extracellular matrix, and (f) an endothelial cell (E) and fibrocyte processes (asterisks) that have broken through a discontinuity in BM (arrowheads) to displace an RPE cell (R) from its intact monolayer (r). VEGF staining (blue) is minimally present in RPE of 18-month-old wild-type (g) but markedly expressed in RPE and choroid of 18-month-old $Ccl2^{-/-}$ mouse (h). Scale bars 2 μm (a,e,f), 1 μm (b,c), 10 μm (d), and 100 μm (g,h). i-l, Intrachoroidal neovascularization leaks indocyanine green but not fluorescein. i, Late phase (12 min) fluorescein angiogram corresponding to area in a-c shows no leakage (arrow) in the region whereas j-l , indocyanine green angiography reveals a focal area (arrow) of hyperfluorescence that increases over time (j-3 min, k-6 min, 1-10 min). m,n, Choroidal neovascularization leaks fluorescein. m, Fluorescein angiography shows focal early (2 min) hyperfluorescence (m) that increases both in intensity and area in the late (9 min) frame (n) corresponding to region in d-f.

The subretinal deposits observed in the Ccl2 and Ccr2 mice have ophthalmoscopic and angiographic (FIG. 1) characteristics similar to drusen in AMD. Some deposits are discrete while others are confluent like hard or soft drusen, respectively, in patients with AMD (FIG. 1). The deposits are histologically similar to the human counterpart and absent in wild-type mice (FIG. 1). Bruch's membrane is visibly thickened in the knockout mice as in AMD. The choroid is markedly hypervascular and thickened, resembling the histologic appearance of intrachoroidal neovascularization (FIG. 3*a-c*). The outer nuclear layer of the neural retina is markedly attenuated, and photoreceptor inner & outer segments are nearly absent in many regions of the retina (FIG. 2), as seen in human AMD in regions of RPE cells compromised by drusen.

Figures 1A, 1B, 1C, 1D, 1E, 1F, 1G, 1H:
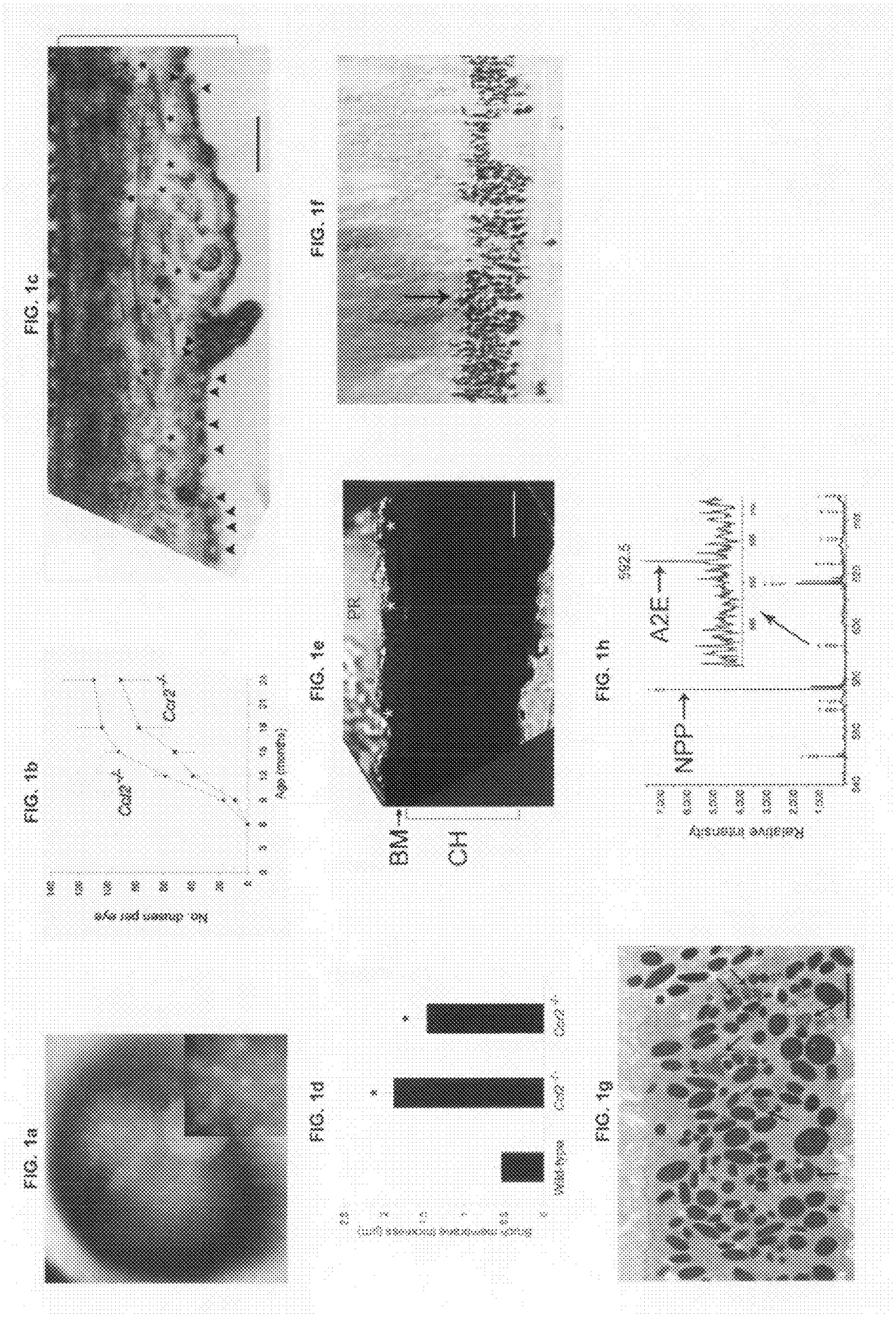
FIG. 1. $Ccl2^{-/-}$ and $Ccr2^{-/-}$ mice develop early AMD. (a) Fundus photo of 15-month-old $Ccl2^{-/-}$ mouse. Inset shows higher magnification. (b) Drusen deposits in knockout mice increase with age (n=4). (c) Collagen and elastin fibers (asterisks) of thickened Bruch membrane (indicated by bracket) in 9-month-old $Ccl2^{-/-}$ mouse are disrupted, and choriocapillaries are highly fenestrated (arrowheads). (d) Bruch membrane is thickened in 10- to 12-month-old knockout mice (n=5). Asterisk $P<0.05$. (e) TIMP-3 (red) immunoreactivity in RPE and Bruch membrane (BM) of 14-month-old $Ccl2^{-/-}$ mouse. There was no staining in photoreceptors (PR) or choroid (CH). (f) Lipofuscin autofluorescence (red) in light micrograph of RPE (arrow) of 15-month-old $Ccl2^{-/-}$ mouse. (g) Lipofuscin granules (arrows) in electron micrograph of 15-month-old $Ccl2^{-/-}$ mouse. (h) MALDI spectrum of RPE of 12-month-old $Ccl2^{-/-}$ mouse, showing A2E signal. NPP, N-perfluoroalkyl pyridine. Scale bar=0.5 μm (c), 50 μm (e), 10 μm (f), or 2 μm (g).
Figures 4A, 4B, 4C, 4D, 4E, 4F, 4G, 4H, 4I:
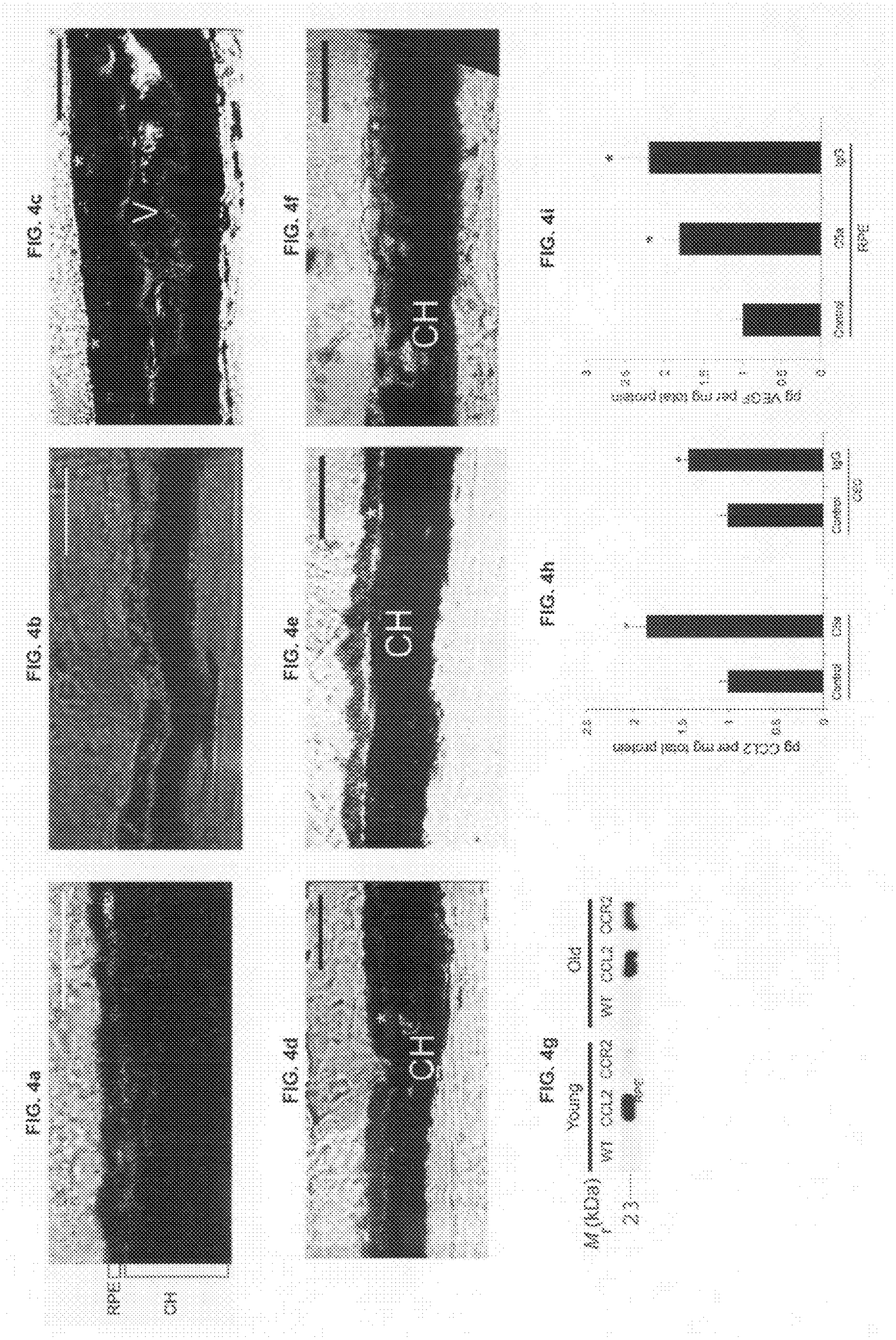
FIG. 4. Complement proteins and IgG deposition in $Ccl2^{-/-}$ and $Ccr2^{-/-}$ mice, and C5a and IgG stimulate Ccl2 and VEGF secretion in RPE cells and CEC. a, Complement C5 (blue) staining in RPE and choroid (CH) of 18-month-old $Ccr2^{-/-}$ mouse. b, IgG staining (blue) in choroid and RPE in 14-month-old $Ccl2^{-/-}$ mouse. c, Colocalization of complement C3c (red) and IgG (green) around choroidal vessel (V) wall and in RPE of 14-month $Ccl2^{-/-}$ mouse. Merged picture shows yellow costaining. d, Vitronectin immunoreactivity in RPE and choroid of 18-month-old $Ccr2^{-/-}$ mouse. e, CD46 staining in RPE of 14-month-old $Ccl2^{-/-}$ mouse. f, Serum amyloid P component staining in RPE and choroid of 14-month $Ccl2^{-/-}$ mouse. RPE, asterisks. Choroid, CH. Scale bar 100 μm (a,b), 25 μm (c), 50 μm (d-f). g, Western blot. RPE and choroid lysates from 6-month-old wild-type (Young WT), 18-month-old wild-type (Old WT), 6-month-old $Ccl2^{-/-}$ (Young CCL2), 16-month-old $Ccl2^{-/-}$ (Old CCL2), 6-month-old $Ccr2^{-/-}$ (Young CCR2), and 18-month-old $Ccr2^{-/-}$ (Old CCR2) mice were analyzed by antibody against mouse IgG. A 23 kD reactive fragment corresponding to IgG light chain was identified. h, Ccl2 release at 24 h from C5a-stimulated RPE cells and IgG-stimulated choroidal endothelial cells (CEC). i, C5a and IgG upregulate RPE secretion of VEGF at 8 h. Asterisks P<0.05.

RPE cells of the knockout mice are engorged with lipofuscin (FIG. 1*g*), autofluorescent lysosomal storage bodies abundant in patients with AMD. Basal membranogranular deposits, the earliest pathological changes in AMD (Green et al., (1993) *Ophthalmology* 100, 1519-35; and Green, et al., (1977) *Trans Am Ophthalmol Soc* 75, 180-254), are seen in Ccl2−/− mice (FIG. 1). Bruch's membrane was markedly thickened and internally fragmented in these mice, with disruption of the collagen and elastin layers (FIG. 4*d*). The average thickness of Bruch's membrane in nine month-old knockout mice (1.8 μm) is significantly higher than in wild-type mice at the same age (0.45 μm). By comparison, in humans with AMD, the average thickness of Bruch's membrane is approximately 3 μm (Ramrattan, et al., (1994) *Invest Ophthalmol Vis Sci* 35, 2857-64). Lipofusin granules, autofluorescent lysosomal residual bodies that accumulate with age in RPE cells of human, have been implicated in AMD development (Delori et al., 2000) and are found in Ccl-2−/− mice in an age dependent fashion, as is A2E, the principal fluorophore of lipofuscin (FIG. 1*h*).

Choroidal neovascularization (CNV) is observed in Ccl2 mice. FIG. 3 shows leakage due to CNV as captured by indocyanine angiography. FIG. 3*a-c* are transmission electron micrographs of CNV that depicts breaks in Bruch's membrane with choroidal endothelium injecting processes through these breaks. This pathology, which is identical to the earliest event in the development of CNV in human patients with AMD, has not previously been described in a spontaneous model.

Examination of human drusen revealed the presence of C5a within the deposits. It was also found that recombinant complement 5a up-regulates the secretion of Ccl2 in human RPE cells (FIG. 4*h*). This may explain the presence of subretinal deposits in Ccl2 and Ccr2 deficient mice, which cannot recruit macrophages, which are thought to aid drusen clearance (Duvall and Tso, 1985). This provides a mechanistic link between drusen and macrophage recruitment, and suggests a causal link between the gene defects and the presence of drusen in these knockout mice.

The totality of the data suggests that macrophages play a critical role in drusen resorption, which is impaired in the absence of Ccl2 or its receptor Ccr2. The presence of both drusen and CNV (the respective key findings of both types (non-exudative and exudative) of macular degeneration) in these mice at an age similar to human (adjusted for species longevity) makes this an attractive model for investigating AMD and the role of senescence. This model not only provides evidence for a macrophage role in drusen clearance, but also provides a powerful platform to study the molecular etiology of AMD and the effect of candidate drugs or treatments on the development or progression of AMD.

Current animal models of CNV (the neovascular form of AMD that accounts for over 80% of visual loss in patients with AMD) relying on laser injury to fracture Bruch's membrane or viral transfection of VEGF into RPE cells, although useful for experimental study, are poor facsimiles of the human condition. Thus, particularly remarkable was the identification of CNV with frank evidence of angiographic leakage in 4 of 15 Ccl2−/− and 3 of 13 Ccr2−/− mice older than 18 months, and in none of 16 age-matched wild-type mice. This frequency of conversion to the neovascular stage is comparable to the rate of progression from drusen to CNV in humans with AMD1. At earlier stages (15-19 months), CNV had breached the outer, but not inner, aspect of Bruch's membrane (intrachoroidal neovascularization), showing angiographic leakage of indocyanine green but not fluorescein (FIG. 3*a-c, i-l*). This nascent angiogenesis later (18-27 months) completely breached Bruch's membrane, causing RPE and photoreceptor disruption due to the accumulation of subretinal fluid leakage from these immature vessels, which was visible on fluorescein angiography (FIG. 3*d-f, m, n*). It is shown in FIG. 3 that VEGF was overexpressed in the RPE in senescent Ccl2 or Ccr2 deficient, but not age-matched wild-type, mice (FIG. 3*g,h*), consistent with its putative role as the angiogen driving CNV.

Recent evidence suggests that complement activation and immune complex deposition occur in eyes of humans with AMD. (Mullins, et al., FASEB J 14, 835-846 (2000); Johnson, et al., Exp Eye Res 70, 441-449 (2000); and Anderson et al., Am J Ophthalmol 134, 411-431 (2002). The deposition of many of these proteins in aging Ccl2−/− and Ccr2−/− mice was observed in the present studies. Complement component C5 (FIG. 4*a*), immunoglobulin G (IgG) (FIG. 4*b,c,g*), the complement regulatory proteins vitronectin (Vn) and CD46 (membrane cofactor protein) (FIG. 4*d,e*), serum amyloid P component (SAP), a potential activator of the complement cascade (FIG. 4*f*), and advanced glycation endproducts (AGE) (data not shown) were present in RPE or choroid of both strains of knockout mice, but not age-matched wild-types, similar to their distribution in eyes with AMD. Colocalization of IgG and C3c in choroidal vessel walls (FIG. 4*c*) not only suggests the presence of immune complexes, but also reflects ongoing immune deposit formation because C3c, a split-product of surface bound C3b, is cleared within hours. The joint presence of CD46, a membrane-bound regulator that facilitates inactivation of the activated complement components C3b/C4b, and vitronectin, a fluid-phase regulator that binds to the terminal complement complex to regulate complement-mediated lysis, along with localization of complement intermediates suggests that complement activation occurs to completion. These deposits were identified in 6 of 7 Ccl2−/− and 4 of 6 Ccr2−/− mice as young as 6 months of age, predating the changes visible on fundus examination, consistent with a potential causal role. Such deposits were not identified in wild-type mice.

In other immune complex deposition disorders, it has been postulated that these proteins serve as an inflammatory nidus by inciting macrophage recruitment through Fc and complement receptor binding, triggering humoral activation and phagocytosis. Consistent with this hypothesis, it is shown herein that Ccl2 secretion by human RPE and choroidal endothelial cells (CEC) was upregulated by C5a (the activated form of C5) and IgG, respectively (FIG. 4*h*). AGE also stimulates human RPE cell secretion of Ccl2 (ref. 27).

Figure 5A:
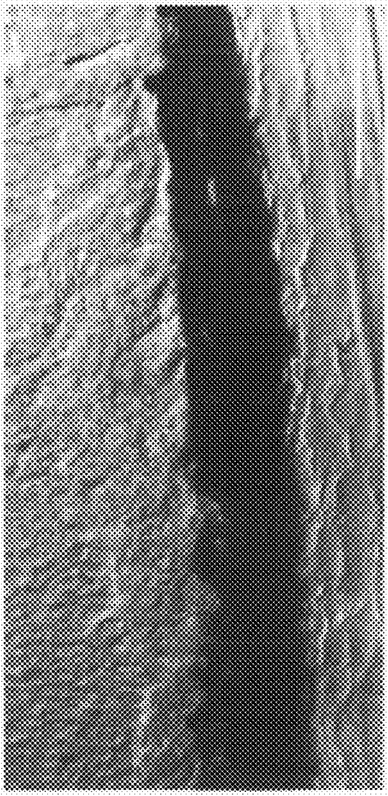
FIG. 5. Ccl2 overexpression and macrophage infiltration in aged wild-type mice. Ccl2 fluorescence (blue) is not observed in 4-month-old wild-type (a) but marked immunoreactivity is present in RPE and choroid of 12-month-old wild-type mouse (b). Cluster of F4/80 positive (blue) macrophages in choroid of 12-month-old wild-type (c) but not in 16-month-old $Ccl2^{-/-}$ mouse (d). Scale bar 150 μm (a,b) and 15 μm (c,d). e, Percentage of choroidal cells expressing F4/80 (macrophages) in young (3-month-old; white bars) and old (12-month-old; black bars) wild-type and knockout mice. n=4. Asterisk P<0.01. f, Western blot. RPE and choroid lysates from 6-month-old wild-type (Young WT), 18-month-old wild-type (Old WT), 6-month-old $Ccl2^{-/-}$ (Young CCL2), 16-month-old $Ccl2^{-/-}$ (Old CCL2), 6-month-old $Ccr2^{-/-}$ (Young CCR2), and 18-month-old $Ccr2^{-/-}$ (Old CCR2) mice were analyzed by antibody against mouse C5aR. A 50 kD reactive fragment corresponding to a reduced C5a receptor fragment was identified.
Figure 5B:
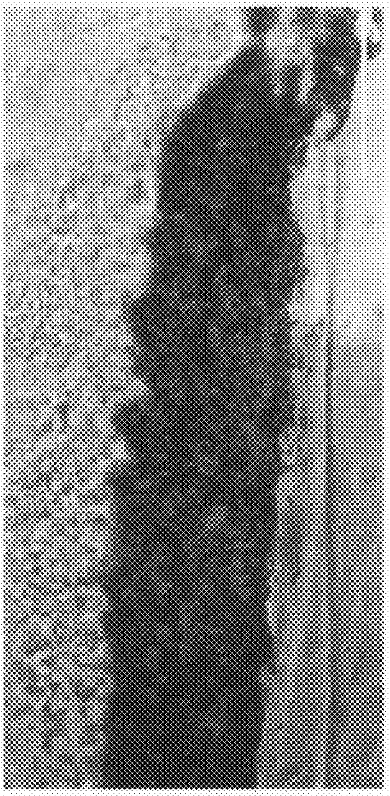
Figure 5C:
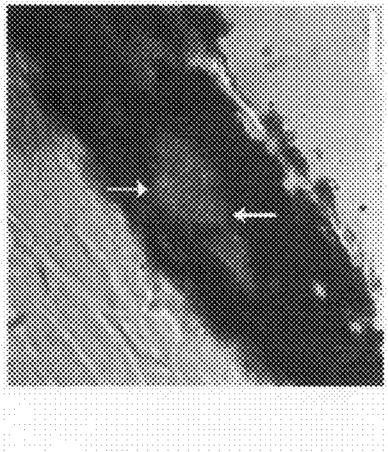
Figure 5D:
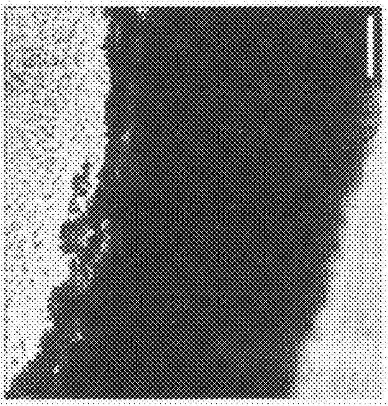
Figure 5E:
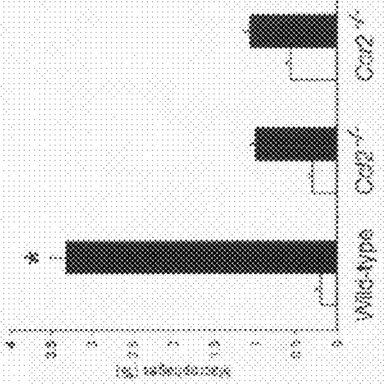
Figure 5F:
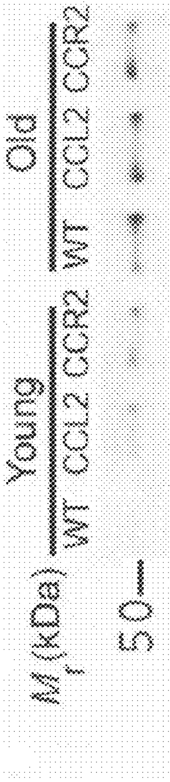

These data may explain the presence of subretinal deposits in Ccl2 and Ccr2 deficient mice which are impaired in recruiting macrophages requisite for clearance and degradation of drusen and other debris. Consistent with this hypothesis, there was an age-dependent increase in the expression of Ccl2 in the RPE (FIG. 5*a,b*), and in macrophage infiltration in the choroid of wild-type mice (FIG. 5*c-e*). Using flow cytometry, we found that aging was associated with a marked increase (15-fold) in the number of macrophages in the choroid of wild-types compared with only a modest (2-3 fold) increase in knockout mice (FIG. 5*e*). These data suggest that macrophage recruitment in aged wild-type mice is principally directed along the Ccl2-Ccr2 axis. Along with overexpression of C5 in the RPE and choroid of Ccl2−/− and Ccr2−/− mice, marked upregulation of the C5a receptor (C5aR) in both strains of knockout mice starting at an early age, and in wild-type mice at a later age was observed (FIG. 5*f*). These findings suggest that in the wild-type animal ongoing stimulation by C5a, which upregulates C5aR expression, leads to Ccl2 production and subsequent clearance of C5 and molecules tagged by this opsonin. The inability to summon sufficient numbers of or appropriately stimulated macrophages in knockout mice however, would lead to continued C5 deposition.

Both C5a and IgG stimulated human RPE cells to increase their secretion of the potent angiogenic cytokine vascular endothelial growth factor (VEGF) (FIG. 4*i*), which is consistent with RPE overexpression of VEGF in senescent Ccl2 or Ccr2 deficient mice (FIG. 3*h*). AGE also upregulates human RPE and CEC secretion of VEGF. Together these processes may underlie the development of CNV and highly fenestrated choroidal capillaries (FIG. 1*c*, 3*c*), both of which can be induced by VEGF in these mice.

Figures 6A, 6B, 6C, 6D, 6E, 6F, 6G:
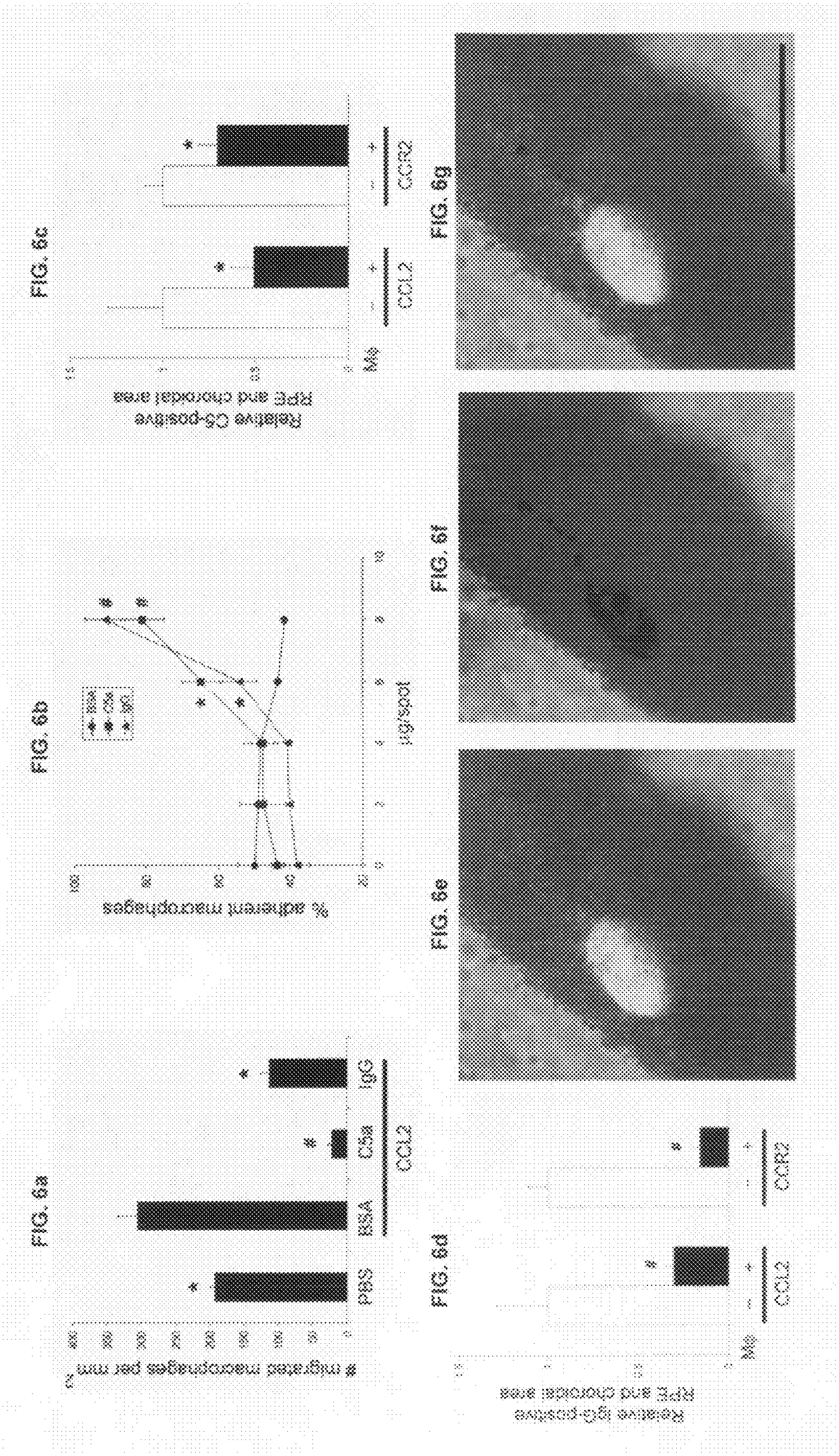
FIG. 6. Macrophages are immobilized by, adhere to, and degrade C5 and IgG. a, Migration of wild-type peritoneal macrophages, toward Ccl2, across membranes coated with CIV and BSA, C5a, or IgG. * P<0.05, # P<0.01 compared with BSA. n=3. b, Adhesion of wild-type peritoneal macrophages to slides coated with CIV and C5a or IgG. * P<0.05, # P<0.01 compared to BSA. n=3. c,d, Choroidal macrophages of 12-month-old wild-type mice clear C5 and IgG in situ. Quantitation shows significantly less C5 (c) and IgG (d) immunoreactivity in sections from 12-14-month-old knockout mice incubated with macrophages (Mϕ) compared with sections without macrophages. * P<0.05, # P<0.01. n=4-7. e-g, Confocal images from 12-month-old $Ccr2^{-/-}$ mouse eye section incubated with wild-type choroidal macrophages for 2 h. An F4/80 positive (blue) macrophage adheres to the section (e). IgG-immunoreactive material (red) (f) seems closely associated with and engulfed by macrophage in the merged image (g). Scale bar 15 μm.

Cell culture inserts were used to examine the migration of macrophages across a porous membrane coated with collagen IV (CIV, an abundant constituent of Bruch's membrane) in response to Ccl2. The migration of macrophages across this CIV-coated membrane when simultaneously coated with C5a or IgG was then tested to determine whether macrophages recruited to these protein-deposition sites by locally secreted Ccl2 are immobilized when they contact these proteins in the extracellular matrix. It was found that Ccl2-induced macrophage chemotaxis was inhibited both by C5a and IgG (FIG. 6*a*). Such immobilization indicates that macrophages adhere to C5a or IgG coated surfaces. Using CIV-coated multi-spot slides coated with C5a or IgG, it was shown that macrophages adhere to these proteins in a dose-dependent fashion (FIG. 6*b*). Collectively these data suggest that macrophages recruited by Ccl2 become immobilized when they contact C5a or IgG and associate with them in the extracellular matrix.

Because macrophages were immobilized by and adhered to C5 and IgG in vitro, and aging was associated with macrophage infiltration into the choroid of wild-type mice, it is possible that these cells scavenge immune complexes identified in the eyes of Ccl2−/− or Ccr2−/− mice. To test this hypothesis, macrophages were purified from aged wild-type choroids by magnetic cell sorting and plated on unfixed eye sections from Ccl2−/− or Ccr2−/− mice which were rich in C5 and IgG deposits in their RPE and choroids. Incubation with wild-type macrophages for 24 hours markedly reduced the total RPE/choroidal area occupied by C5 or IgG, compared with untreated sections (FIGS. 6*c,d*). Within 2 hours, macrophages were spread out over the tissue and intimately associated with protein deposits (FIG. 6*e-g*). These results indicate that macrophages clear C5 and IgG deposits in situ and assign a pivotal role for macrophage deficiency in the accumulation of complement components and immunoglobulins in Ccl2−/− or Ccr2−/− mice.

The present invention provides the first animal model of AMD that recapitulates the key elements of the human condition in senescent mice lacking the macrophage chemoattractant Ccl2 or its cognate receptor Ccr2. The presence of similar pathology in two ligand/receptor strains that are defective in induced macrophage trafficking strengthens the hypothesis that macrophage dysfunction plays a role in its pathogenesis. The accumulation of several complement components, complement regulatory proteins, and IgG in these mutant mice, as in humans with AMD, suggests that impaired macrophage recruitment allows accretion of proteins associated with complement activation and immune complex deposition. Inability to summon macrophages is thus associated with senescence-associated development of features strongly reminiscent of human AMD, corroborated by several lines of evidence. In particular the present inventors have shown that Ccl2-driven macrophages are immobilized by and adhere to C5a and IgG in vitro, and that macrophages degrade these proteins in situ. Combined with the observation of a marked deficiency of macrophages in the choroids of aged knockout mice, these data suggest that impaired macrophage mobilization in vivo leads to non-clearing of these proteins since these cells are known to scavenge immune complexes via complement opsonization in vivo.

Since deposition of complement-related proteins and IgG precedes the development of drusen and lipofuscin, it is likely that AMD-like pathology is due, at least in part, to complement activation and immune complex deposition rather than the converse. Because RPE cells in eyes with AMD that are immunoreactive for complement-related proteins and IgG exhibit anatomic prelethal signs it has been suggested that accumulation of these proteins compromises RPE function The presence of IgG along with complement C3 and C5 intermediates is strongly suggestive of the presence of immune complexes, and is consistent with the presence of circulating retinal auto-antibodies in patients with AMD. Furthermore, patients with membranoproliferative glomerulonephritis, in which complement activation and immune complex deposition cause glomerular injury, develop drusen resembling AMD-associated drusen in ultrastructure and composition, including C5 and IgG deposition, as well as CNV. Collectively these findings support the concept that complement activation and immune complex deposition may injure the RPE in AMD. RPE injury, which may be manifested by secondary photoreceptor degradation, also can be triggered by excessive accumulation of lipofuscin. SAP and TIMP-3 also may impair drusen clearance by functioning as protease inhibitors. RPE overexpression of VEGF stimulated by complement components and IgG combined with fragmentation of Bruch's membrane provides an environment permissive for CNV.

The presence of both atrophic and neovascular pathologies in Ccl2−/− or Ccr2−/− mice at an age corresponding to human senescence makes these mice attractive models for investigating both early and late AMD. Because mouse retina does not contain a specialized macula, this model is not an exact replica of the human condition. However, the pathology in human AMD, while pronounced in the macular area, is not confined to this central region, and the findings observed in aged Ccl2−/− or Ccr2−/− mice closely resemble those of the clinical condition in anatomical appearance, biochemical composition, and functional disruption. More importantly, they define a system for molecular dissection of the determinants of AMD pathogenesis, and provide a platform to develop and validate novel therapeutic strategies and test compounds Ccl2−/−, Ccr2 −/− mice and dual knockout mice, Ccl2−/−/Ccr2−/− mice may be used to characterize the temporal development of AMD, preferably from ages of about 9 to about 24 months by ophthalmoscopy, angiography, and histopathology, for example, as compared to wild-type age-matched mice. In characterizing the development of AMD the eyes of these mice are systematically examined at various ages, such as for example, at 1, 3, 6, 9, 12, 18, and 24 months to characterize the temporal development of the retinal and subretinal pathology. For example, the eyes of the mice may be examined by:

1. Clinical Retinal Evaluation—examination & fundus photography through dilated pupil, e.g., 50 degree fundus photography to quantify yellow spots (drusen);
2. Fluorescein angiography—Staining or leakage within the eye may be identified;
3. Histology—Paraffin embedded and frozen sections of affected eyes may be studied for morphology and biochemical composition (lipid, cholesterol, lipofuscin);
4. Immunohistochemistry—Drusen (C5a, C5b-9, ApoE, vitronectin, clusterin staining for human correlation); Proliferating cell nuclear antigen (PCNA)+CD31 (proliferating choroidal endothelium); and/or
5. Electron Microscopy—Morphology and morphometry of various structures, e.g., photoreceptors, RPE, Bruch's membrane (integrity and thickness), choroidal vasculature may be examined.

In one aspect of the invention, the Ccl2, Ccr2 and/or Ccl2/Ccr2 (dual knockout) knockout mice may be used to test candidate drugs for treatment of AMD. Dual knockout mice are created by a series of genetic backcrosses using the cross-backcross-intercross scheme, which is well known in the art. Ccr2−/− mice are mated with Ccl2−/− mice to yield heterozygous F1 offspring. The F1 mice are intercrossed and the progeny screened by PCR, for example, for Ccr2 and Ccl2. B1 progeny, heterozygous for Ccr2 and Ccl2 are intercrossed, and mice homozygous for both disrupted genes are selected for example, by PCR typing for continued backcrossing. Mice are genotyped by any method, such as by analyzing tail DNA samples using Southern blot strategies or by PCR analysis with multiprimer sets that amplify in the disrupted gene, transgene insert or neomycin resistance gene insert.

Candidate drugs include pharmaceutical compounds, small molecules, peptides, antibodies, antibody fragments and nucleic acids, including oligonucleotides and polynucleotides in sense or antisense orientation and aptamers. In this aspect of the invention the candidate drug is administered to the mouse orally, systemically, e.g., intravenously, intraperitoneally, intravitreously (e.g., by injection or sustained delivery implant), transsclerally or topically, and preferably by topical application to at least one eye of a test group of Ccl2 mice, Ccr2 mice, dual knockout mice or all three types of mutant mice, and the eye(s) of the treated mice are periodically examined to determine the effect of the candidate drug on drusen accumulation, lipofuscin accumulation, Bruch's membrane or any other symptomatic marker of AMD. A decrease in drusen or lipofuscin accumulation or thinning of Bruch's membrane, an affect on retinal degeneration or choroidal neovascularization, for example, is an indication of the ability of the candidate drug to effectively treat AMD.

In one embodiment of the invention, the genetic defect is treated by introducing a wild-type gene Ccl2 or Ccr2 gene into the mouse. Chemotactic deficiency in Ccl2−/− mice may be reversed by delivering a recombinant vector, such as for example an adeno-associated virus (rAAV) vector expressing the cDNA for Ccl2. Although Ccl2 can be delivered via an osmotic pump, rAAV vector administration is not only as effective as systemic administration, but also confines production and secretion of Ccl2, and is likely to restrict chemotactic activity to the eye. Reconstituting Ccl2 function via AAV transduction is also superior to systemic delivery as the former permits intra-animal inter-eye comparisons, thus providing greater statistical and biological fidelity to the hypothesis testing. Also rAAV vectors have demonstrated long-term, sustained high-level expression in the retina for two years, eliminating the need for pump replacement.

Similarly, the Ccr2 defect may be treated by administering a vector encoding wild-type Ccr2 gene to determine whether rescue of Ccr2 function prevents or causes regression of AMD in Ccr2 mice or dual knockout mice. Alternatively the Ccr2 defect may be corrected by stem cell transplantation of cells from Ccr2+/+ animals, either by adoptive transfer or following bone marrow ablation. Similarly, the Ccl2 defect may be corrected by stem cell transplantation of cells from Ccl2+/+ animals, either by adoptive transfer or following bone marrow ablation, for example.

The rAAV-vector cassette preferably includes a promoter, such as for example a chicken β-actin (CBA) promoter, which preferably is composed of an enhancer element or elements, such as a cytomegalovirus (CMV) immediate-early enhancer (381 bp) and a CBA promoter-exonl-intronl element (1,352 bp) upstream of a simian virus 40 early splice donor/splice-acceptor site, the Ccl2, gene, or both and a polyadenylation sequence, preferably the simian virus 40 polyadenylation sequence. The entire expression cassette containing the Ccl2 cDNA or Ccr2 cDNA is preferably flanked by AAV2 terminal repeats required for viral packaging. Viral vectors are packaged and purified as described (Raisler, B. J., Berns, K. I., Grant, M. B., Beliaev, D. & Hauswirth, W. W. (2002) *Proc Natl Acad Sci USA* 99, 8909-14). The CBA promoter is preferably used as it supports expression well in both RPE cells and photoreceptors (Acland et al. (2001) *Nat Genet* 28, 92-5).

Efficacy of transduction by the rAAV-CBA-Ccl2, -Ccr2 or vector encoding both Ccl2 and Ccr2 may be confirmed by any method including any combination of the following:

1. In vitro expression: RPE cells harvested and cultured from eyes of wild-type and Ccl2−/− mice may be probed by PCR amplification for the presence or absence of the wild-type Ccl2 transgene or Ccr2 transgene, respectively. Wild-type RPE cells and mutant RPE cells transfected with rAAV-CBP-Ccl2, -Ccr2 or vector encoding both Ccl2 and CCR2 may be subjected to PCR amplification, and optionally ELISA of the supernatant for expression of Ccl2, which is constitutively secreted (Elner, et al., (1997) *Exp Eye Res* 65, 781-9).
2. In vivo expression: The amount of ocular protein in mice expressed from the vector construct may be assayed after subretinal vector inoculation by ELISA about six weeks after injection. Approximately $10^{10}$ particles ($2\times10^{8}$ infectious units) in a volume of 1 μl of therapeutic vector is injected into one eye and the same volume of null vector in the fellow eye.
3. AAV-CBA-Ccl2, -Ccr2 or both Ccl2 and Ccr2 is injected into eyes of Ccl2 deficient mice, preferably about eight-week-old Ccl2 deficient, Ccr2-deficient mice, or dual knockout mice, and the temporal development of retinal and subretinal lesions is compared to fellow eyes injected with null vector over 24 months with interval measurements. In addition a vector such as AAV-CBA-Ccl2, AAV-CBA-Ccr2 or both or a single vector encoding both Ccl2 and Ccr2 may be injected into eyes of one-year-old Ccl2 deficient mice, one year old Ccr2 deficient mice or dual knockout mice, and the stabilization or regression of ocular lesions evaluated in comparison to fellow eyes.

In addition Ccl2 and Ccr2 function can be reconstituted by bone marrow transplantation from Ccl2+/+ or Ccr2+/+ mice.

In another aspect of the invention, there is provided a double knockout mouse which has both the Ccl2 and Ccr2 deletions. The mouse may be generated as described above, or by any method known to the skilled practitioner. The mouse is useful for determining the pathology of age-related macular degeneration and testing candidate drugs for treatment of age-related macular degeneration.

It is also contemplated that the genes, vectors and expression vectors of the invention may be used for stem cell transplantation to restore Ccr2 function. For example, stem cells obtained from a normal mouse, i.e., containing a wild type Ccr2 gene, may be introduced either by adoptive transfer or following bone marrow ablation. For example, the normal stem cells may be introduced by intravenous injection into a Ccr2−/− mouse or other animal. The eyes of the animal receiving the stem cell transplant are then observed to determine the effect of the transplantation. Alternatively, a Ccr2−/− mouse or other animal can be subjected to bone marrow irradiation to deplete stem cells. Following ablation of the endogenous stem cells, stem cells obtained from a wild type mouse are administered to the irradiated Ccr2−/− mouse, preferably by intravenous injection. The eyes of the transplanted mouse are then observed to determine the effect of the transplantation. Similar procedures can be employed to restore Ccl2 function in a Ccl2−/− mouse or other animal.

It is also contemplated that AMD can be treated or prevented in mammals, including humans, by administering to a patient in need, a wild type Ccr2 gene, wild type Ccl2 gene or both to compensate for a defective Ccr2 gene or Ccl2 gene or both. The wild type gene can be administered by any method known in the art, such as by administering the gene(s) via an expression vector, such as a replication defective adenovirus vector, directly into the eye, via an implant or via intravenous injection. Alternatively, the wild type gene can be introduced into the eye via stem cell transplantation as described above.

It is further contemplated that wild type Ccl2 and/or Ccr2 genes or small molecules that promote the finction of Ccl2 and/or Ccr2 are used for the manufacture of a medicament for the treatment or prevention of AMD in a mammal.

It is further contemplated that the genes, vectors and expression vectors, including the promoter/enhancer regions of the genes for Ccl2 and/or Ccr2 may be used in identifying mutations or polymorphisms that place people at increased or decreased risk for developing AMD. The human Ccl2 gene, its promoter and enhancer (SEQ ID NO. 1-4) and human Ccr2 gene and its promoter (SEQ ID NO. 5-8) are shown in FIGS. 7A-D and 8A-D, respectively. These sequences can be used to isolate the Ccr2 and/or Ccl2 gene from genomic DNA obtained from patients suspected of having or believed to be at risk of developing age-related macular degeneration. Also, the wild type Ccl2 and/or Ccr2 sequences or fragments thereof can be used directly or oligonucleotides based on these sequences can be generated and used to screen genomic or cDNA AMD libraries using any method known in the art. Generally, high stringency conditions are used in the screening process. Methods for screening genomic DNA and gene libraries and selection of stringency conditions are well known to those of skill in the art. See, e.g., Maniatis et al., Molecular Cloning A Laboratory Manual. The isolated genes or gene fragments can then be sequenced to determine the presence of mutations in the isolated DNA. Once specific AMD mutations or polymorphisms are identified, these mutations can be used to screen patients for the presence of the mutation.

Applicants' studies have shown that C5 and C5a accumulate in the eyes of the Ccl2−/− and Ccr2−/− mice with aging, and that the inability of macrophages to clear these deposits leads to macular degeneration-like changes in the mice. Thus, defects in the C5 receptor and C5a receptor genes may promote macular degeneration. Therefore, an analysis of the C5 receptor gene and C5a receptor genes in AMD patients for the presence or absence of mutations or polymorphisms will confirm the role of these genes in the development of AMD. The sequence of each of the human C5 receptor and C5a receptor genes is shown in SEQ ID NO. 9 and 10, respectively. As discussed above for the Ccl2 and Ccr2 genes, the wild type C5 receptor and C5a receptor genes may be used to screen AMD libraries or genomic DNA obtained from AMD patients for the C5 receptor and C5a receptor genes therein and the genes so isolated can be characterized, by nucleotide sequencing to determine the presence or absence of mutations or polymorphisms, for example. Also, the C5 receptor and C5a receptor genes may be cloned into an appropriate expression vector or expression vector and further characterized.

EXAMPLES

Animals: Wild-type C57BL/6 mice (Jackson Laboratories), and Ccl2−/− and Ccr2−/− strains, generated as described previously (Lu, et al., J Exp Med 187, 601-608 (1998); Kuziel, et al, Proc Natl Acad Sci USA 94, 12053-12058 (1997)) (incorporated herein by reference) and backcrossed 10 times to C57BL/6, were anesthetized by intramuscular injection of ketamine (50 mg/kg) and xylazine (10 mg/kg).

Fundus photography and angiography: Photographs and angiograms performed after intraperitoneal injection of fluorescein sodium (Akorn; 60 mg/kg) or indocyanine green (Sigma-Aldrich; 6 mg/kg) were captured with a TRC-50IA camera (Topcon) and evaluated by two masked readers.

Immunohistochemistry and electron microscopy: Frozen sections fixed in Histochoice MB (Amresco) and blocked with 5% donkey serum (Jackson Immunoresearch) were stained with rabbit anti-mouse C3c (1:1000; gift of J. D. Lambris, University of Pennsylvania, Philadelphia, Pa.), mouse anti-mouse C5 (1:1000; gift of J. D. Lambris), rabbit anti-human CD46 (1:500; Santa Cruz Biotechnologies), goat anti-mouse MCP-1 (15 micro g/ml; R&D Systems), goat anti-human SAP (1:500; Santa Cruz), rabbit anti-mouse TIMP-3 (1:2500; gift of B. H. F. Weber, University of Wuerzburg, Wuerzburg, Germany), goat anti-mouse VEGF (15 micro g/ml; R&D Systems), rabbit polyclonal anti-AGE antibodies (1:1000, gift of A. Gugliucci, Touro University, Vallejo, Calif.), or goat anti-human vitronectin (1:500; Santa Cruz). Bound antibodies were detected with Cy3-conjugated goat secondaries or CyS-conjugated donkey secondaries (1:100; Jackson Immunoresearch). Alternatively sections were stained directly with FITC-conjugated goat anti-mouse IgG (1:100; BD Pharmingen), Cy5-conjugated donkey anti-mouse IgG (1:100; Jackson lmmunoresearch) or Cy5-conjugated F4/80 (5 micro g/ml; Serotec). A "mouse-on-mouse" kit (Vector Laboratories) was used for C5 staining. Lipofuscin autofluorescence was detected through the Cy3 channel. Transmission electron microscopic studies were performed on uranyl acetate/lead citrate-stained ultrathin sections. Bruch's membrane thicknesses were measured 150 micro m from the optic nerve by averaging thinnest and thickest parts.

Western blotting: Equal amounts of total protein from RPE/choroid were resolved in SDS 4-20% polyacrylamide gradient gel and transferred to nitrocellulose membranes for western blotting with antibodies against mouse C5aR (gift of J. D. Lambris) or mouse IgG (Transduction Laboratories).

Flow cytometry: Single cell suspensions of RPE/choroids were incubated in Fc block (0.5 mg/ml; BD Pharmingen) for 15 min on ice, stained with Cy5-F4/80 antibody (1:30), and live cells were detected by gating on forward versus side scatter, followed by analysis of F4/80 in the fluorescence channel (FACScalibur, BD Biosciences).

Migration: Wild-type peritoneal macrophage migration (10,000 cells/well) toward 30 nM of mouse Ccl2 (R&D Systems) was assayed using 24-well transwell chambers (Corning) separated by a 5 micrometer polycarbonate filter coated with 50 micro g/ml collagen IV (CIV; Fluka), with or without overlay of human C5a (50 nM; Calbiochem), mouse IgG (50 micro g/well; Jackson Immunoresearch), or bovine serum albumin (BSA; 50 micro g/well; Sigma-Aldrich), by counting numbers of migrated cells after 3 hours incubation at 37 degrees C.

Adherence: Adherence of wild-type peritoneal macrophages (105 cells/spot) plated on multispot glass slides (Shandon) coated with 50 micro g/ml CIV overlaid with human C5a, mouse IgG, or BSA (0-8 micro g/spot). was quantitated using CyQuantGR (Molecular Probes) after incubation at 37 degrees C. for 1 h.

Degradation: Frozen unfixed eye sections from knockout mice were transferred to 24-well culture plates and incubated with or without wild-type (12-month-old) choroidal macrophages (10,000 cells/well), purified via magnetic cell sorting using MicroBeads conjugated with CD11b antibody (clone M1/70.15.11.5; Miltenyi Biotec), for up to 24 h at 37 degrees C. Sections were fixed with Histochoice MB, stained for C5, IgG, or F4/80, and imaged by scanning confocal microscopy. Relative areas of C5 or IgG immunoreactivity were measured for 4-7 sections using image-analysis software (Photoshop, ver. 6.0; Adobe Systems).

Cell stimulation: Serum starved human CEC (gift of D. R. Hinton, University of Southern California, Los Angeles, Calif.) and human RPE cells were stimulated with human C5a (50 ng/ml) or immobilized human IgG (50 micro g/well; Sigma-Aldrich) after attaining 80% confluence. Ccl2 and VEGF levels measured by ELISA (R&D Systems) at 8 and 24 h after stimulation were normalized to total protein.

MALDI-TOF mass spectrometry: RPE extracts and standards of synthetic N-retinylidene -N-retinylethanolamine (A2E; gifts of E. Rodriguez-Boulan, New York University, New York, N.Y. and G. H. Travis, University of California, Los Angeles, Calif.) were dissolved in 50% methanol/50% water (Fisher Scientific), transferred to C18 PrepSep solid phase extraction columns (Fisher), and eluted with 1 ml methanol containing 0.1 % trifluoroacetic acid (TFA; Fisher). N-perfluoroalkyl pyridine (NPP; gift of S. Rankin, University of Kentucky, Lexington, Ky.; 250 ng) was added to samples as an external standard. The MALDI target was prepared by adding 0.5 micro 1 sample to deposited 0.5 micro 1 matrix (alpha-cyano-4-hydroxycinnamic acid; Sigma-Aldrich). Positive ion spectra were acquired on a Bruker Autoflex MALDI-TOF mass spectrometer (Bruker Daltonic). The A2E response (m/z 592.5) was normalized to the NPP response (m/z 576.1).

Statistics: Data are represented as the mean ±s.e.m. of at least 3 independent experiments and were compared using a two-tailed Student's t-test. The null hypothesis was rejected at $P<0.05$.

Example 1

Eyes of greater than 60 Ccl2−/− and Ccr2−/− mice and 40 age-matched wild-type mice ranging from 3 to 27 months were subjected to fundus examination. Of these, eyes from 25 Ccl2−/−, 21 Ccr2−/−, and 18 age-matched wild-type (<12 months: 6; 12-24 months: 7; >24 months: 5) mice were extensively examined histopathologically. Before 9 months of age, the fundi of Ccl2−/− and Ccr2−/− mice were indistinguishable from wild-type mice. Thereafter subretinal deposits with ophthalmoscopic and pathologic features of drusen in patients with AMD were observed in all mice of both knockout strains and increased in number with age as in humans (FIG. 1*a, b*). In contrast, no such changes were visible in wild-type mice even at 24 months of age (n=5). Bruch's membrane (the extracellular matrix between the RPE and choroid) was markedly thickened in senescent Ccl2 or Ccr2 deficient mice compared with age-matched wild-types and that its collagen and elastin layers were severely disrupted with internal fragmentation (FIG. 1*c*), features observed in AMD. As in patients with AMD, intense immunostaining of tissue inhibitor of metalloproteinases (TIMP)-3, produced by the RPE and thought to contribute to thickening of Bruch's membrane, was observed in aged knockout mice (FIG. 1*e*). As Ccl2−/− and Ccr2−/− mice aged, increasing amounts of lipofuscin granules (autofluorescent lysosomal residual bodies which accumulate with age in RPE cells of humans and have been implicated in AMD development) were observed in swollen and vacuolated RPE cells (FIG. 1*f, g*) at 9 months and thereafter. Ultrastructural analysis of these RPE cells showed significant intracellular accumulation of dense bodies (FIG. 1*h*) including large ellipsoid and spherical structures of high electron density, presumably representing melanosomes and melanolipofuscin fusion particles, respectively, and numerous smaller structures of variable density representing lipofuscin granules. RPE extracts were tested for the presence of N-retinylidene-N-retinylethanolamine (A2E), the principal lipofuscin fluorophore by matrix-assisted laser desorption/ionization-time-of-flight (MALDI-TOF) mass spectrometry. RPE extracts from 12-month-old knockouts contained 25 pmol of A2E per eye (FIG. 1*i*). No A2E was detected in RPE of age-matched wild-type mice. Lipofuscin accumulation is thought to promote RPE dysfunction in AMD.

Example 2

Retinal Degeneration and Choroidal Neovascularization in Ccl2−/− and Ccr2−/− Mice As Ccl2−/− and Ccr2−/− mice aged, they exhibited several of the late findings seen in human AMD, including progressive outer retinal degeneration and CNV, similar to that seen in patients with late AMD. Despite evidence of RPE and choroidal pathology, differences in neural retinal morphology between knockout strains and wild-types were not observed before 16 months of age. At 16 months of age and thereafter, both knockout strains exhibited confluent areas of visible atrophy similar to "geographic atrophy" seen in advanced AMD (FIG. 2*a*). These areas were characterized by cell loss in the outer nuclear layer of the retina and atrophy of photoreceptor segments (FIG. 2*b-e*), as well as attenuation of the RPE and choriocapillaris (FIG. 2*f*) as in late AMD. In these regions the RPE was hypopigmented along with prominent vacuolization and degeneration of most intracellular organelles, and was devoid of basal infoldings. The choriocapillaris was nearly obliterated with few or no patent inner choroidal vessels observed in the areas corresponding to fundus atrophy. Regions outside these areas did not display such atrophy (FIG. 2*g,h*).

Example 3

CCR2 rescue of the ocular abnormalities in Ccr2 deficient mice is accomplished by creating chimeric mice using bone marrow transplantation (BMT). In vitro AAV transduction results in loss of stem cell activity during infection, while in vivo transduction results in non-specific and low-level target expression (only 1 per 15,000 bone marrow cells are stem cells); neither approach will guarantee sustained expression in vivo. Ccr2 −/− mice are irradiated and repopulated with bone marrow stem cells from wildtype Ccr2 +/+ mice. Ccr2 −/− mice are maintained on antibiotic-containing water for one week before irradiation. These mice are irradiated with 900 cGy from a cesium source (delivered in two equal doses of 450 cGy 3-4 hours apart), and donor bone marrow cells ($1\times10^7$) are injected into a tail vein. Mice are maintained on antibiotic-containing water for four weeks after transplantation. Engraftment is verified by PCR detection of the Ccr2 gene in the bone marrow of all irradiated mice. Eyes of eight-week-old chimeric mice are compared to ungrafted Ccr2−/− mice over 24 months with interval measurements. In addition, eyes of Ccr2−/− mice repopulated with bone marrow at one year of age are compared to ungrafted mice over the following year.

Example 4

A candidate drug for the treatment of AMD is applied to one or both eyes of a Ccl2 mouse, which was previously confirmed to have developed AMD symptoms, e.g., drusen and/or lipofuscin deposits in the eye, thickening of Bruch's membrane. Treatment is repeated at least once daily for one to several weeks. Examination of the treated eye(s) by visual and/or fundus examination through dilated pupil is carried out periodically during treatment and the effect of treatment is compared to placebo treated wild-type eyes.

What is claimed is:

1. A method for testing a candidate drug for treatment of age-related macular degeneration (AMD) comprising (i) administering the candidate drug to at least one eye of a Ccl2−/− knockout mouse and/or a Ccr2−/− knockout mouse, wherein the at least one eye exhibits at least one symptom comprising drusen accumulation, lipofuscin accumulation, thickening of Bruch's membrane, retinal degeneration, choroidal neovascularization, or a combination thereof, (ii) determining the effect of the candidate drug on the at least one symptom, and (iii) correlating the effect of the candidate drug on the at least one symptom with a potential utility to treat AMD.

2. The method of claim 1 wherein the candidate drug is nucleic acid.

3. The method of claim 1 wherein the candidate drug comprises a viral vector encoding wild-type Ccl2.

4. The method of claim 1 wherein the candidate drug comprises a viral vector encoding wild type Ccr2.

5. The method of claim 1, wherein determining the effect of the candidate drug on the at least one symptom comprises determining amount and type of drusen or lipofuscin, extent of retinal degeneration, or neovascularization developed therein or a combination thereof.

6. The method according to claim 1 wherein the at least one eye is analyzed by ophthalmoscopy, angiography, histopathology or a combination thereof.

7. The method of claim 1 wherein the candidate drug is administered to the mouse orally, intravenously, intraperitoneally, intravitreously, transsclerally or topically.

8. The method of claim 7 wherein the candidate drug is administered topically to at least one eye of the mouse.

9. The method of claim 1 wherein the candidate drug is a pharmaceutical compound, small molecule, peptide, antibody, antibody fragment, aptamer or nucleic acid.

10. The method of claim 9 wherein the nucleic acid is an oligonucleotide or polynucleotide in either the sense or antisense orientation or an aptamer.

11. A method of screening a candidate drug for potential utility for treatment of age-related macular degeneration, comprising:

(a) providing a Ccl2−/− and/or CCR2−/− knockout mouse which exhibits drusen accumulation, lipofuscin accumulation, thickening of Bruch's membrane, retinal degeneration, choroidal neovascularization, or a combination thereof in at least one eye, (b) administering the candidate drug to the knockout mouse;

(c) determining the effect of the candidate drug on drusen, lipofuscin deposition, retinal degeneration, and/or choroidal neovascularization in at least one eye of the knockout mouse; and (d) correlating the effect of the candidate drug on drusen, lipofuscin accumulation, retinal degeneration, and/or choroidal neovascularization with a potential utility to treat age-related macular degeneration.

12. The method of claim 11 wherein the candidate drug is nucleic acid.

13. The method of claim 11 wherein the candidate drug comprises a viral vector encoding wild-type Ccl2.

14. The method of claim 11 wherein the candidate drug comprises a viral vector encoding wild type Ccr2.

15. The method of claim 11 wherein analyzing the at least one eye comprises determining amount and type of drusen or lipofuscin, retinal degeneration, neovascularization developed therein or a combination thereof.

16. The method according to claim 11 wherein the at least one eye is analyzed by ophthalmoscopy, angiography, histopathology, mass spectometry or a combination thereof.

17. The method of claim 11 wherein the candidate drug is administered to the mouse orally, intravenously, intraperitoneally, intravitreously, transsclerally or topically.

18. The method of claim 11 wherein the candidate drug is a pharmaceutical compound, small molecule, peptide, antibody, antibody fragment, aptamer or nucleic acid.

19. The method of claim 12 wherein the nucleic acid is an oligonucleotide or polynucleotide in either the sense or antisense orientation or an aptamer.

20. The method of claim 7 wherein the candidate drug is administered intravitreously by injection or by sustained delivery implant, to at least one eye of the mouse.

21. The method of claim 7 wherein the candidate drug is administered transsclerally to at least one eye of the mouse.

22. The method of claim 11 wherein candidate drug is administered intravitreously by injection or by sustained delivery implant, to at least one eye of the mouse.

23. The method of claim 11 wherein the candidate drug is administered transsclerally to at least one eye of the mouse.

24. The method of claim 17 wherein the candidate drug is administered intravitreously by injection or by sustained delivery implant to at least one eye of the mouse.

25. The method of claim 17 wherein the candidate drug is administered transsclerally to at least one eye of the mouse.

26. The method of claim 1 wherein the candidate drug comprises stem cells obtained from a wild-type mouse and intravitreously injected into the Ccl2−/− and/or Ccr2−/− knockout mouse.

27. The method of claim 11 wherein the candidate drug comprises stem cells obtained from a wild-type mouse and injected intravitreously into the Ccl2−/− and/or CCR2−/− knockout mouse.

* * * * *